(12) United States Patent
Zhou et al.

(10) Patent No.: US 11,174,314 B2
(45) Date of Patent: Nov. 16, 2021

(54) ANTI-KRAS BINDING PROTEINS

(71) Applicant: Sorrento Therapeutics, Inc., San Diego, CA (US)

(72) Inventors: Heyue Zhou, San Diego, CA (US); Min Soo Kim, San Diego, CA (US)

(73) Assignee: Sorrento Therapeutics, San Diego, CA (US)

( * ) Notice: Subject to any disclaimer, the term of this patent is extended or adjusted under 35 U.S.C. 154(b) by 0 days.

(21) Appl. No.: 16/380,121

(22) Filed: Apr. 10, 2019

(65) Prior Publication Data

US 2019/0284275 A1    Sep. 19, 2019

Related U.S. Application Data

(63) Continuation of application No. PCT/IB2017/056334, filed on Oct. 12, 2017.

(60) Provisional application No. 62/407,982, filed on Oct. 13, 2016, provisional application No. 62/414,196, filed on Oct. 28, 2016, provisional application No. 62/416,913, filed on Nov. 3, 2016.

(51) Int. Cl.

| | |
|---|---|
| *A61K 39/00* | (2006.01) |
| *C07K 16/28* | (2006.01) |
| *A61P 31/00* | (2006.01) |
| *A61P 35/00* | (2006.01) |
| *A61K 39/395* | (2006.01) |
| *C12N 5/12* | (2006.01) |
| *A61K 47/68* | (2017.01) |
| *C07K 16/32* | (2006.01) |
| *C07K 16/30* | (2006.01) |

(52) U.S. Cl.
CPC .. *C07K 16/2803* (2013.01); *A61K 39/001139* (2018.08); *A61K 39/395* (2013.01); *A61K 47/6807* (2017.08); *A61K 47/6851* (2017.08); *A61K 47/6859* (2017.08); *A61P 31/00* (2018.01); *A61P 35/00* (2018.01); *C07K 16/303* (2013.01); *C07K 16/32* (2013.01); *C12N 5/12* (2013.01); *A61K 2039/505* (2013.01); *A61K 2039/55511* (2013.01); *C07K 2317/21* (2013.01); *C07K 2317/73* (2013.01); *C07K 2317/77* (2013.01); *C07K 2317/92* (2013.01)

(58) Field of Classification Search
CPC ............ A61K 47/6851; A61K 47/6807; A61K 47/6859; C07K 16/32; C07K 2317/92; A61P 35/00
See application file for complete search history.

(56) References Cited

U.S. PATENT DOCUMENTS

| | | |
|---|---|---|
| 5,977,322 A | 11/1999 | Marks et al. |
| 7,498,414 B2 | 3/2009 | Zhu |
| 7,507,797 B2 | 3/2009 | Knackmuss et al. |
| 8,329,178 B2 | 12/2012 | Marasco et al. |
| 2005/0215770 A1 | 9/2005 | Bell et al. |

FOREIGN PATENT DOCUMENTS

WO    WO 2016/085904 A1    6/2016

OTHER PUBLICATIONS

Strome et al., The Oncologist, 2007; 12:1084-95 (Year: 2007).*
Brand et al., Anticancer Res. 2006; 26:463-70 (Year: 2006).*
UniProtKB Accession No. A0A0G2K3A6, Jul. 22, 2015 [online]. Retrieved from the Internet: https://www.uniprot.org/uniprot/A0A0G2K3A6.txt?version=1 amino acids 26-35.
UniProtKB Accession No. G6B0U4, Jan. 25, 2012 [online]. Retrieved from the internet: https://www.uniprot.org/uniprot/G8B0U4.txt?version=1 amino acids 367-374.
UniProtKB Accession No. A2N2W8, Feb. 20, 2007 [online]. Retrieved from the internet: https://www.uniprot.org/uniprot/A2N2W8.txt?version=1 amino acids 39-45.
Shin et al., "Antibody Targeting Intracellular Oncogenic Ras Mutants Exerts Anti-Tumour Effects After Systemic Administration", Nature Communications 8:15090 (May 10, 2017), pp. 1-14.
International Search Report corresponding to International Patent Application No. PCT/IB2017/056334, dated May 31, 2018, 5 pages.

* cited by examiner

*Primary Examiner* — Sheela J. Huff
(74) *Attorney, Agent, or Firm* — McNeill Baur PLLC

(57) ABSTRACT

The present disclosure provides anti-KRAS antibodies, and antigen-binding fragments thereof. In certain embodiments, the anti-KRAS antibodies or fragments thereof, are used for the treatment of cancer.

20 Claims, 11 Drawing Sheets

Specification includes a Sequence Listing.

ANTI-KRAS BINDING PROTEINS

CROSS REFERENCE TO RELATED APPLICATIONS

This patent application is a continuation of International Application No. PCT/IB2017/056334, filed Oct. 12, 2017, which claims the benefit of U.S. provisional application No. 62/407,982, filed Oct. 13, 2016, U.S. provisional application No. 62/414,196, filed Oct. 28, 2016, and U.S. provisional application No. 62/416,913, filed Nov. 3, 2016, all of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Mar. 30, 2019, is named 2019-03-30_01223-0016-00US_SequenceListing.txt and is 145 kilobytes in size.

TECHNICAL FIELD

The present disclosure provides human antibodies that bind KRAS, KRAS-binding fragments and derivatives of such antibodies, KRAS-binding polypeptides comprising such fragments, and conjugates thereof.

BACKGROUND OF THE INVENTION

The KRAS gene (also known as V-Ki-ras2 Kirsten rat sarcoma viral oncogene homolog), encodes a 2.1-kDa small protein that is activated transiently in response to extracellular stimuli or signals such as growth factors, cytokines, and hormones via cell surface receptors. The RAS proteins are guanine nucleotide binding molecules that play key roles in signal transduction as molecular switches, mediated through two switch regions displaying conformational differences between active (GTP bound) and inactive (GDP bound) states. Most of the RAS effectors bind to these RAS switch regions.

The protein product of the KRAS gene performs an essential function in normal tissue signaling, where the mutation of a KRAS gene is an essential step in the development of many cancers. The RAS oncogenes (1-IRAS, NRAS and KRAS) comprise the most frequently mutated class of oncogenes in human cancers (33%), stimulating intensive effort in developing anti-RAS inhibitors for cancer treatment. RAS is an important target in cell transformation, being involved in cell proliferation and differentiation and cell survival through activation of PI3K. Aside from a few rare exceptions, mutationally activated Ras proteins found in human cancers result predominantly from one of three single point mutations at residues G12, G13, or Q61. Oncogenic substitution of G12 or G13 leads to constitutive activation of Ras by creating steric hindrance that prevents the formation of van der Waals interactions between Ras and RasGAPS (Scheffzek et al (1997) *Science* 277, 333-338).

RAS-based therapies have been challenging (see, for example, Cardinale et al. (2003) *Eur. J. Biochem.* 270:3389), especially given the intracellular nature of the target. Tanaka et al. (2007) *EMBO J.* 26:3250 describes a single antibody domain that targeted the interaction of signal transduction proteins with RAS, and was able to impact protein-protein interactions. There remains an unmet need for novel agents that block aberrant KRAS function for cancer treatments, particularly therapies directed to intracellular targets such as KRAS.

SUMMARY OF THE INVENTION

The invention provides antibodies that specifically bind to KRAS, including human KRAS.

In one aspect, the invention features an isolated anti-KRAS antibody, or an antigen-binding fragment thereof, comprising a heavy chain variable domain comprising a heavy chain CDR set (CDR1, CDR2, and CDR3) of amino acid sequences selected from the group consisting of SEQ ID Nos. 75, 76 and 77; SEQ ID Nos. 81, 82 and 83; SEQ ID Nos. 87, 88 and 89; SEQ ID Nos. 93, 94 and 95; SEQ ID Nos. 99, 100 and 101; SEQ ID Nos. 105, 106 and 107; SEQ ID Nos. 111, 112 and 113; SEQ ID Nos. 117, 118 and 119; SEQ ID Nos. 123, 124 and 125; SEQ ID Nos. 129, 130 and 131; SEQ ID Nos. 135, 136 and 137; SEQ ID Nos. 141, 142 and 143; SEQ ID Nos. 147, 148 and 149; SEQ ID Nos. 153, 154 and 155; SEQ ID Nos. 159, 160, 161; SEQ ID Nos. 165, 166 and 167; SEQ ID Nos. 171, 172 and 173; SEQ ID Nos. 177, 178 and 179; SEQ ID Nos. 183, 184 and 185; SEQ ID Nos. 189, 190 and 191; SEQ ID Nos. 195, 196 and 197; SEQ ID Nos. 201, 202 and 203; SEQ ID Nos. 207, 208 and 209; SEQ ID Nos. 213, 214 and 215; SEQ ID Nos. 219, 220 and 221; SEQ ID Nos. 225, 226 and 227; SEQ ID Nos. 231, 232 and 233; SEQ ID Nos. 237, 238 and 239; SEQ ID Nos. 243, 244 and 245; SEQ ID Nos. 249, 250 and 251; SEQ ID Nos. 255, 256 and 257; SEQ ID Nos. 261, 262 and 263; SEQ ID Nos. 267, 268 and 269; SEQ ID Nos. 273, 274 and 275; SEQ ID Nos. 279, 280 and 281; SEQ ID Nos. 285, 286 and 287; SEQ ID Nos. 291, 292 and 293; and SEQ ID Nos. 299, 300 and 301; and a light chain variable domain comprising a light chain CDR set (CDR1, CDR2, and CDR3) of amino acid sequences selected from the group consisting of SEQ ID Nos. 78, 79 and 80; SEQ ID Nos. 84, 85 and 86; SEQ ID Nos. 90, 91 and 92; SEQ ID Nos. 96, 97 and 98; SEQ ID Nos. 102, 103 and 104; SEQ ID Nos. 108, 109 and 110; SEQ ID Nos. 114, 115 and 116; SEQ ID Nos. 120, 121 and 122; SEQ ID Nos. 126, 127 and 128; SEQ ID Nos. 132, 133 and 134; SEQ ID Nos. 138, 139 and 140; SEQ ID Nos. 144, 145 and 146; SEQ ID Nos. 150, 151 and 152; SEQ ID Nos. 156, 157 and 158; SEQ ID Nos. 162, 163 and 164; SEQ ID Nos. 168, 169 and 170; SEQ ID Nos. 174, 175 and 176; SEQ ID Nos. 180, 181 and 182; SEQ ID Nos. 186, 187 and 188; SEQ ID Nos. 192, 193 and 194; SEQ ID Nos. 198, 199 and 200; SEQ ID Nos. 204, 205 and 206; SEQ ID Nos. 210, 211 and 212; SEQ ID Nos. 216, 217 and 218; SEQ ID Nos. 222, 223 and 224; SEQ ID Nos. 228, 229 and 230; SEQ ID Nos. 234, 235 and 236; SEQ ID Nos. 240, 241 and 242; SEQ ID Nos. 246, 247 and 248; SEQ ID Nos. 252, 253 and 254; SEQ ID Nos. 258, 259 and 260; SEQ ID Nos. 264, 265 and 266; SEQ ID Nos. 270, 271 and 272; 276, 277 and 278; SEQ ID Nos. 282, 283 and 284; SEQ ID Nos. 288, 289 and 290; SEQ ID Nos. 294, 295 and 296 and SEQ ID Nos. 302, 303 and 304.

In one embodiment, the heavy chain variable domain is selected from the group consisting of a heavy chain variable domain comprising an amino acid sequence that is at least 95% identical to SEQ ID NO: 1 and comprising the heavy chain CDR set of SEQ ID Nos: 75, 76, and 77; a heavy chain variable domain comprising an amino acid sequence that is at least 95% identical to SEQ ID NO: 3 and comprising the heavy chain CDR set of SEQ ID Nos: 81, 82 and 83; a heavy chain variable domain comprising an amino acid sequence that is at least 95% identical to SEQ ID NO: 5 and comprising the heavy chain CDR set of SEQ ID Nos: 87, 88 and 89; a heavy chain variable domain comprising an amino acid sequence that is at least 95% identical to SEQ ID NO: 7 and comprising the heavy chain CDR set of SEQ ID Nos: 93, 94 and 95; a heavy chain variable domain comprising an amino acid sequence that is at least 95% identical to SEQ ID NO: 9 and comprising the heavy chain CDR set of SEQ ID Nos: 99, 100 and 101; a heavy chain variable domain comprising an amino acid sequence that is at least 95% identical to SEQ ID NO: 11 and comprising the heavy chain CDR set of SEQ ID Nos: 105, 106 and 107; a heavy chain variable domain comprising an amino acid sequence that is at least 95% identical to SEQ ID NO: 13 and comprising the heavy chain CDR set of SEQ ID Nos: 111, 112 and 113; a heavy chain variable domain comprising an amino acid sequence that is at least 95% identical to SEQ ID NO: 15 and comprising the heavy chain CDR set of SEQ ID Nos: 117, 118 and 119; a heavy chain variable domain comprising an amino acid sequence that is at least 95% identical to SEQ ID NO: 17 and comprising the heavy chain CDR set of SEQ ID Nos: 123, 124 and 125; a heavy chain variable domain comprising an amino acid sequence that is at least 95% identical to SEQ ID NO: 19 and comprising the heavy chain CDR set of SEQ ID Nos: 129, 130 and 131; a heavy chain variable domain comprising an amino acid sequence that is at least 95% identical to SEQ ID NO: 21 and comprising the heavy chain CDR set of SEQ ID Nos: 135, 136 and 137; a heavy chain variable domain comprising an amino acid sequence that is at least 95% identical to SEQ ID NO: 23 and comprising the heavy chain CDR set of SEQ ID Nos: 141, 142 and 143; a heavy chain variable domain comprising an amino acid sequence that is at least 95% identical to SEQ ID NO: 25 and comprising the heavy chain CDR set of SEQ ID Nos: 147, 148 and 149; a heavy chain variable domain comprising an amino acid sequence that is at least 95% identical to SEQ ID NO: 27 and comprising the heavy chain CDR set of SEQ ID Nos: 153, 154 and 155; a heavy chain variable domain comprising an amino acid sequence that is at least 95% identical to SEQ ID NO: 29 and comprising the heavy chain CDR set of SEQ ID Nos: 159, 160 and 161; a heavy chain variable domain comprising an amino acid sequence that is at least 95% identical to SEQ ID NO: 31 and comprising the heavy chain CDR set of SEQ ID Nos: 165, 166 and 167; a heavy chain variable domain comprising an amino acid sequence that is at least 95% identical to SEQ ID NO: 33 and comprising the heavy chain CDR set of SEQ ID Nos: 171, 172 and 173; a heavy chain variable domain comprising an amino acid sequence that is at least 95% identical to SEQ ID NO: 35 and comprising the heavy chain CDR set of SEQ ID Nos: 177, 178 and 179; a heavy chain variable domain comprising an amino acid sequence that is at least 95% identical to SEQ ID NO: 37 and comprising the heavy chain CDR set of SEQ ID Nos: 183, 184 and 185; a heavy chain variable domain comprising an amino acid sequence that is at least 95% identical to SEQ ID NO: 39 and comprising the heavy chain CDR set of SEQ ID Nos: 189, 190 and 191; a heavy chain variable domain comprising an amino acid sequence that is at least 95% identical to SEQ ID NO: 41 and comprising the heavy chain CDR set of SEQ ID Nos: 195, 196 and 197; a heavy chain variable domain comprising an amino acid sequence that is at least 95% identical to SEQ ID NO: 43 and comprising the heavy chain CDR set of SEQ ID Nos: 201, 202 and 203; a heavy chain variable domain comprising an amino acid sequence that is at least 95% identical to SEQ ID NO: 45 and comprising the heavy chain CDR set of SEQ ID Nos: 207, 208 and 209; a heavy chain variable domain comprising an amino acid sequence that is at least 95% identical to SEQ ID NO: 47 and comprising the heavy chain CDR set of SEQ ID Nos: 213, 214 and 215; a heavy chain variable domain comprising an amino acid sequence that is at least 95% identical to SEQ ID NO: 49 and comprising the heavy chain CDR set of SEQ ID Nos: 219, 220 and 221; a heavy chain variable domain comprising an amino acid sequence that is at least 95% identical to SEQ ID NO: 51 and comprising the heavy chain CDR set of SEQ ID Nos: 225, 226 and 227; a heavy chain variable domain comprising an amino acid sequence that is at least 95% identical to SEQ ID NO: 53 and comprising the heavy chain CDR set of SEQ ID Nos: 231, 232 and 233; a heavy chain variable domain comprising an amino acid sequence that is at least 95% identical to SEQ ID NO: 55 and comprising the heavy chain CDR set of SEQ ID Nos: 237, 238 and 239; a heavy chain variable domain comprising an amino acid sequence that is at least 95% identical to SEQ ID NO: 57 and comprising the heavy chain CDR set of SEQ ID Nos: 243, 244 and 245; a heavy chain variable domain comprising an amino acid sequence that is at least 95% identical to SEQ ID NO: 59 and comprising the heavy chain CDR set of SEQ ID Nos: 249, 250 and 251; a heavy chain variable domain comprising an amino acid sequence that is at least 95% identical to SEQ ID NO: 61 and comprising the heavy chain CDR set of SEQ ID Nos: 255, 256 and 257; a heavy chain variable domain comprising an amino acid sequence that is at least 95% identical to SEQ ID NO: 63 and comprising the heavy chain CDR set of SEQ ID Nos: 261, 262 and 263; a heavy chain variable domain comprising an amino acid sequence that is at least 95% identical to SEQ ID NO: 65 and comprising the heavy chain CDR set of SEQ ID Nos: 267, 268 and 269; a heavy chain variable domain comprising an amino acid sequence that is at least 95% identical to SEQ ID NO: 67 and comprising the heavy chain CDR set of SEQ ID Nos: 273, 274 and 275; a heavy chain variable domain comprising an amino acid sequence that is at least 95% identical to SEQ ID NO: 69 and comprising the heavy chain CDR set of SEQ ID Nos: 279, 280 and 281; a heavy chain variable domain comprising an amino acid sequence that is at least 95% identical to SEQ ID NO: 71 and comprising the heavy chain CDR set of SEQ ID Nos: 285, 286 and 287; a heavy chain variable domain comprising an amino acid sequence that is at least 95% identical to SEQ ID NO: 73 and comprising the heavy chain CDR set of SEQ ID Nos: 291, 292 and 293; and a heavy chain variable domain comprising an amino acid sequence that is at least 95% identical to SEQ ID NO: 297 and comprising the heavy chain CDR set of SEQ ID Nos: 299, 300 and 301. In another embodiment, the light chain variable domain is selected from the group consisting of a light chain variable domain comprising an amino acid sequence that is at least 95% identical to SEQ ID NO: 2 and comprising the light chain CDR set of SEQ ID Nos: 78, 79 and 80; a light chain variable domain comprising an amino acid sequence that is at least 95% identical to SEQ ID NO: 4 and comprising the light chain CDR set of SEQ ID Nos: 84, 85 and 86; a light chain variable domain comprising an amino acid sequence that is at least 95% identical to SEQ ID NO: 6 and comprising the light chain CDR set of SEQ ID Nos: 90, 91 and 92; a light chain variable domain comprising an amino acid sequence that is at least 95% identical to SEQ ID NO: 8 and comprising the light chain CDR set of SEQ ID Nos: 96, 97 and 98; a light chain variable domain comprising an amino acid sequence that is at least 95% identical to SEQ ID NO: 10 and comprising the light chain CDR set of SEQ ID Nos: 102, 103 and 104; a light chain variable domain comprising an amino acid sequence that is at least 95% identical to SEQ ID NO: 12 and comprising the light chain CDR set of SEQ ID Nos:

108, 109 and 110; a light chain variable domain comprising an amino acid sequence that is at least 95% identical to SEQ ID NO: 14 and comprising the light chain CDR set of SEQ ID Nos: 114, 115 and 116; a light chain variable domain comprising an amino acid sequence that is at least 95% identical to SEQ ID NO: 16 and comprising the light chain CDR set of SEQ ID Nos: 120, 121 and 122; a light chain variable domain comprising an amino acid sequence that is at least 95% identical to SEQ ID NO: 18 and comprising the light chain CDR set of SEQ ID Nos: 126, 127 and 128; a light chain variable domain comprising an amino acid sequence that is at least 95% identical to SEQ ID NO: 20 and comprising the light chain CDR set of SEQ ID Nos: 132, 133 and 134; a light chain variable domain comprising an amino acid sequence that is at least 95% identical to SEQ ID NO: 22 and comprising the light chain CDR set of SEQ ID Nos: 138, 139 and 140; a light chain variable domain comprising an amino acid sequence that is at least 95% identical to SEQ ID NO: 24 and comprising the light chain CDR set of SEQ ID Nos: 144, 145 and 146; a light chain variable domain comprising an amino acid sequence that is at least 95% identical to SEQ ID NO: 26 and comprising the light chain CDR set of SEQ ID Nos: 150, 151 and 152; a light chain variable domain comprising an amino acid sequence that is at least 95% identical to SEQ ID NO: 28 and comprising the light chain CDR set of SEQ ID Nos: 156, 157 and 158; a light chain variable domain comprising an amino acid sequence that is at least 95% identical to SEQ ID NO: 30 and comprising the light chain CDR set of SEQ ID Nos: 163, 163 and 164; a light chain variable domain comprising an amino acid sequence that is at least 95% identical to SEQ ID NO: 32 and comprising the light chain CDR set of SEQ ID Nos: 168, 169 and 170; a light chain variable domain comprising an amino acid sequence that is at least 95% identical to SEQ ID NO: 34 and comprising the light chain CDR set of SEQ ID Nos: 174, 175 and 176; a light chain variable domain comprising an amino acid sequence that is at least 95% identical to SEQ ID NO: 36 and comprising the light chain CDR set of SEQ ID Nos: 180, 181 and 182; a light chain variable domain comprising an amino acid sequence that is at least 95% identical to SEQ ID NO: 38 and comprising the light chain CDR set of SEQ ID Nos: 186, 187 and 188; a light chain variable domain comprising an amino acid sequence that is at least 95% identical to SEQ ID NO: 40 and comprising the light chain CDR set of SEQ ID Nos: 192, 193 and 194; a light chain variable domain comprising an amino acid sequence that is at least 95% identical to SEQ ID NO: 42 and comprising the light chain CDR set of SEQ ID Nos: 198, 199 and 200; a light chain variable domain comprising an amino acid sequence that is at least 95% identical to SEQ ID NO: 44 and comprising the light chain CDR set of SEQ ID Nos: 204, 205 and 206; a light chain variable domain comprising an amino acid sequence that is at least 95% identical to SEQ ID NO: 46 and comprising the light chain CDR set of SEQ ID Nos: 210, 211 and 212; a light chain variable domain comprising an amino acid sequence that is at least 95% identical to SEQ ID NO: 48 and comprising the light chain CDR set of SEQ ID Nos: 216, 217 and 218; a light chain variable domain comprising an amino acid sequence that is at least 95% identical to SEQ ID NO: 50 and comprising the light chain CDR set of SEQ ID Nos: 222, 223 and 224; a light chain variable domain comprising an amino acid sequence that is at least 95% identical to SEQ ID NO: 52 and comprising the light chain CDR set of SEQ ID Nos: 228, 229 and 227; a light chain variable domain comprising an amino acid sequence that is at least 95% identical to SEQ ID NO: 54 and comprising the light chain CDR set of SEQ ID Nos: 234, 235 and 236; a light chain variable domain comprising an amino acid sequence that is at least 95% identical to SEQ ID NO: 56 and comprising the light chain CDR set of SEQ ID Nos: 240, 241 and 242; a light chain variable domain comprising an amino acid sequence that is at least 95% identical to SEQ ID NO: 58 and comprising the light chain CDR set of SEQ ID Nos: 246, 247 and 248; a light chain variable domain comprising an amino acid sequence that is at least 95% identical to SEQ ID NO: 60 and comprising the light chain CDR set of SEQ ID Nos: 252, 253 and 254; a light chain variable domain comprising an amino acid sequence that is at least 95% identical to SEQ ID NO: 62 and comprising the light chain CDR set of SEQ ID Nos: 258, 259 and 260; a light chain variable domain comprising an amino acid sequence that is at least 95% identical to SEQ ID NO: 64 and comprising the light chain CDR set of SEQ ID Nos: 264, 265 and 266; a light chain variable domain comprising an amino acid sequence that is at least 95% identical to SEQ ID NO: 66 and comprising the light chain CDR set of SEQ ID Nos: 270, 271 and 272; a light chain variable domain comprising an amino acid sequence that is at least 95% identical to SEQ ID NO: 68 and comprising the light chain CDR set of SEQ ID Nos: 276, 277 and 278; a light chain variable domain comprising an amino acid sequence that is at least 95% identical to SEQ ID NO: 70 and comprising the light chain CDR set of SEQ ID Nos: 282, 283 and 284; a light chain variable domain comprising an amino acid sequence that is at least 95% identical to SEQ ID NO: 72 and comprising the light chain CDR set of SEQ ID Nos: 288, 289 and 290; and a light chain variable domain comprising an amino acid sequence that is at least 95% identical to SEQ ID NO: 74 and comprising the light chain CDR set of SEQ ID Nos: 294, 295 and 296; and a light chain variable domain comprising an amino acid sequence that is at least 95% identical to SEQ ID NO: 298 and comprising the light chain CDR set of SEQ ID Nos: 302, 303 and 304. In another embodiment, the heavy chain variable domain is selected from the group consisting of a heavy chain variable domain comprising an amino acid sequence that is at least 96% identical to SEQ ID NO: 1 and comprising the heavy chain CDR set of SEQ ID Nos: 75, 76, and 77; a heavy chain variable domain comprising an amino acid sequence that is at least 96% identical to SEQ ID NO: 3 and comprising the heavy chain CDR set of SEQ ID Nos: 81, 82 and 83; a heavy chain variable domain comprising an amino acid sequence that is at least 96% identical to SEQ ID NO: 5 and comprising the heavy chain CDR set of SEQ ID Nos: 87, 88 and 89; a heavy chain variable domain comprising an amino acid sequence that is at least 96% identical to SEQ ID NO: 7 and comprising the heavy chain CDR set of SEQ ID Nos: 93, 94 and 95; a heavy chain variable domain comprising an amino acid sequence that is at least 96% identical to SEQ ID NO: 9 and comprising the heavy chain CDR set of SEQ ID Nos: 99, 100 and 101; a heavy chain variable domain comprising an amino acid sequence that is at least 96% identical to SEQ ID NO: 11 and comprising the heavy chain CDR set of SEQ ID Nos: 105, 106 and 107; a heavy chain variable domain comprising an amino acid sequence that is at least 96% identical to SEQ ID NO: 13 and comprising the heavy chain CDR set of SEQ ID Nos: 111, 112 and 113; a heavy chain variable domain comprising an amino acid sequence that is at least 96% identical to SEQ ID NO: 15 and comprising the heavy chain CDR set of SEQ ID Nos: 117, 118 and 119; a heavy chain variable domain comprising an amino acid sequence that is at least 96% identical to SEQ ID NO: 17 and comprising the heavy chain CDR set of SEQ ID Nos: 123, 124 and 125; a heavy chain variable domain comprising an amino acid sequence that is at least 96% identical to SEQ ID NO: 19 and comprising the heavy chain CDR set of SEQ ID Nos: 129, 130 and 131; a heavy chain variable domain comprising an amino acid sequence that is at least 96% identical to SEQ ID NO: 21 and comprising the heavy chain CDR set of SEQ ID Nos: 135, 136 and 137; a heavy chain variable domain comprising an amino acid sequence that is at least 96% identical to SEQ ID NO: 23 and comprising the heavy chain CDR set of SEQ ID Nos: 141, 142 and 143; a heavy chain variable domain comprising an amino acid sequence that is at least 96% identical to SEQ ID NO: 25 and comprising the heavy chain CDR set of SEQ ID Nos: 147, 148 and 149; a heavy chain variable domain comprising an amino acid sequence that is at least 96% identical to SEQ ID NO: 27 and comprising the heavy chain CDR set of SEQ ID Nos: 153, 154 and 155; a heavy chain variable domain comprising an amino acid sequence that is at least 96% identical to SEQ ID NO: 29 and comprising the heavy chain CDR set of SEQ ID Nos: 159, 160 and 161; a heavy chain variable domain comprising an amino acid sequence that is at least 96% identical to SEQ ID NO: 31 and comprising the heavy chain CDR set of SEQ ID Nos: 165, 166 and 167; a heavy chain variable domain comprising an amino acid sequence that is at least 96% identical to SEQ ID NO: 33 and comprising the heavy chain CDR set of SEQ ID Nos: 171, 172 and 173; a heavy chain variable domain comprising an amino acid sequence that is at least 96% identical to SEQ ID NO: 35 and comprising the heavy chain CDR set of SEQ ID Nos: 177, 178 and 179; a heavy chain variable domain comprising an amino acid sequence that is at least 96% identical to SEQ ID NO: 37 and comprising the heavy chain CDR set of SEQ ID Nos: 183, 184 and 185; a heavy chain variable domain comprising an amino acid sequence that is at least 96% identical to SEQ ID NO: 39 and comprising the heavy chain CDR set of SEQ ID Nos: 189, 190 and 191; a heavy chain variable domain comprising an amino acid sequence that is at least 96% identical to SEQ ID NO: 41 and comprising the heavy chain CDR set of SEQ ID Nos: 195, 196 and 197; a heavy chain variable domain comprising an amino acid sequence that is at least 96% identical to SEQ ID NO: 43 and comprising the heavy chain CDR set of SEQ ID Nos: 201, 202 and 203; a heavy chain variable domain comprising an amino acid sequence that is at least 96% identical to SEQ ID NO: 45 and comprising the heavy chain CDR set of SEQ ID Nos: 207, 208 and 209; a heavy chain variable domain comprising an amino acid sequence that is at least 96% identical to SEQ ID NO: 47 and comprising the heavy chain CDR set of SEQ ID Nos: 213, 214 and 215; a heavy chain variable domain comprising an amino acid sequence that is at least 96% identical to SEQ ID NO: 49 and comprising the heavy chain CDR set of SEQ ID Nos: 219, 220 and 221; a heavy chain variable domain comprising an amino acid sequence that is at least 96% identical to SEQ ID NO: 51 and comprising the heavy chain CDR set of SEQ ID Nos: 225, 226 and 227; a heavy chain variable domain comprising an amino acid sequence that is at least 96% identical to SEQ ID NO: 53 and comprising the heavy chain CDR set of SEQ ID Nos: 231, 232 and 233; a heavy chain variable domain comprising an amino acid sequence that is at least 96% identical to SEQ ID NO: 55 and comprising the heavy chain CDR set of SEQ ID Nos: 237, 238 and 239; a heavy chain variable domain comprising an amino acid sequence that is at least 96% identical to SEQ ID NO: 57 and comprising the heavy chain CDR set of SEQ ID Nos: 243, 244 and 245; a heavy chain variable domain comprising an amino acid sequence that is at least 96% identical to SEQ ID NO: 59 and comprising the heavy chain CDR set of SEQ ID Nos: 249, 250 and 251; a heavy chain variable domain comprising an amino acid sequence that is at least 96% identical to SEQ ID NO: 61 and comprising the heavy chain CDR set of SEQ ID Nos: 255, 256 and 257; a heavy chain variable domain comprising an amino acid sequence that is at least 96% identical to SEQ ID NO: 63 and comprising the heavy chain CDR set of SEQ ID Nos: 261, 262 and 263; a heavy chain variable domain comprising an amino acid sequence that is at least 96% identical to SEQ ID NO: 65 and comprising the heavy chain CDR set of SEQ ID Nos: 267, 268 and 269; a heavy chain variable domain comprising an amino acid sequence that is at least 96% identical to SEQ ID NO: 67 and comprising the heavy chain CDR set of SEQ ID Nos: 273, 274 and 275; a heavy chain variable domain comprising an amino acid sequence that is at least 96% identical to SEQ ID NO: 69 and comprising the heavy chain CDR set of SEQ ID Nos: 279, 280 and 281; a heavy chain variable domain comprising an amino acid sequence that is at least 96% identical to SEQ ID NO: 71 and comprising the heavy chain CDR set of SEQ ID Nos: 285, 286 and 287; a heavy chain variable domain comprising an amino acid sequence that is at least 96% identical to SEQ ID NO: 73 and comprising the heavy chain CDR set of SEQ ID Nos: 291, 292 and 293; and a heavy chain variable domain comprising an amino acid sequence that is at least 95% identical to SEQ ID NO: 297 and comprising the heavy chain CDR set of SEQ ID Nos: 299, 300 and 301. In one embodiment of any one of the above aspects or embodiments, the light chain variable domain is selected from the group consisting of a light chain variable domain comprising an amino acid sequence that is at least 96% identical to SEQ ID NO: 2 and comprising the light chain CDR set of SEQ ID Nos: 78, 79 and 80; a light chain variable domain comprising an amino acid sequence that is at least 96% identical to SEQ ID NO: 4 and comprising the light chain CDR set of SEQ ID Nos: 84, 85 and 86; a light chain variable domain comprising an amino acid sequence that is at least 96% identical to SEQ ID NO: 6 and comprising the light chain CDR set of SEQ ID Nos: 90, 91 and 92; a light chain variable domain comprising an amino acid sequence that is at least 96% identical to SEQ ID NO: 8 and comprising the light chain CDR set of SEQ ID Nos: 96, 97 and 98; a light chain variable domain comprising an amino acid sequence that is at least 96% identical to SEQ ID NO: 10 and comprising the light chain CDR set of SEQ ID Nos: 102, 103 and 104; a light chain variable domain comprising an amino acid sequence that is at least 96% identical to SEQ ID NO: 12 and comprising the light chain CDR set of SEQ ID Nos: 108, 109 and 110; a light chain variable domain comprising an amino acid sequence that is at least 96% identical to SEQ ID NO: 14 and comprising the light chain CDR set of SEQ ID Nos: 114, 115 and 116; a light chain variable domain comprising an amino acid sequence that is at least 96% identical to SEQ ID NO: 16 and comprising the light chain CDR set of SEQ ID Nos: 120, 121 and 122; a light chain variable domain comprising an amino acid sequence that is at least 96% identical to SEQ ID NO: 18 and comprising the light chain CDR set of SEQ ID Nos: 126, 127 and 128; a light chain variable domain comprising an amino acid sequence that is at least 96% identical to SEQ ID NO: 20 and comprising the light chain CDR set of SEQ ID Nos: 132, 133 and 134; a light chain variable domain comprising an amino acid sequence that is at least 96% identical to SEQ ID NO: 22 and comprising the light chain CDR set of SEQ ID Nos: 138, 139 and 140; a light chain variable domain comprising an amino acid sequence that is at least 96% identical to SEQ ID NO: 24 and comprising the light chain CDR set of SEQ ID Nos: 144, 145 and 146; a light chain variable domain comprising an amino acid sequence that is at least 96% identical to SEQ ID NO: 26 and comprising the light chain CDR set of SEQ ID Nos: 150, 151 and 152; a light chain variable domain comprising an amino acid sequence that is at least 96% identical to SEQ ID NO: 28 and comprising the light chain CDR set of SEQ ID Nos: 156, 157 and 158; a light chain variable domain comprising an amino acid sequence that is at least 96% identical to SEQ ID NO: 30 and comprising the light chain CDR set of SEQ ID Nos: 163, 163 and 164; a light chain variable domain comprising an amino acid sequence that is at least 96% identical to SEQ ID NO: 32 and comprising the light chain CDR set of SEQ ID Nos: 168, 169 and 170; a light chain variable domain comprising an amino acid sequence that is at least 96% identical to SEQ ID NO: 34 and comprising the light chain CDR set of SEQ ID Nos: 174, 175 and 176; a light chain variable domain comprising an amino acid sequence that is at least 96% identical to SEQ ID NO: 36 and comprising the light chain CDR set of SEQ ID Nos: 180, 181 and 182; a light chain variable domain comprising an amino acid sequence that is at least 96% identical to SEQ ID NO: 38 and comprising the light chain CDR set of SEQ ID Nos: 186, 187 and 188; a light chain variable domain comprising an amino acid sequence that is at least 96% identical to SEQ ID NO: 40 and comprising the light chain CDR set of SEQ ID Nos: 192, 193 and 194; a light chain variable domain comprising an amino acid sequence that is at least 96% identical to SEQ ID NO: 42 and comprising the light chain CDR set of SEQ ID Nos: 198, 199 and 200; a light chain variable domain comprising an amino acid sequence that is at least 96% identical to SEQ ID NO: 44 and comprising the light chain CDR set of SEQ ID Nos: 204, 205 and 206; a light chain variable domain comprising an amino acid sequence that is at least 96% identical to SEQ ID NO: 46 and comprising the light chain CDR set of SEQ ID Nos: 210, 211 and 212; a light chain variable domain comprising an amino acid sequence that is at least 96% identical to SEQ ID NO: 48 and comprising the light chain CDR set of SEQ ID Nos: 216, 217 and 218; a light chain variable domain comprising an amino acid sequence that is at least 96% identical to SEQ ID NO: 50 and comprising the light chain CDR set of SEQ ID Nos: 222, 223 and 224; a light chain variable domain comprising an amino acid sequence that is at least 96% identical to SEQ ID NO: 52 and comprising the light chain CDR set of SEQ ID Nos: 228, 229 and 227; a light chain variable domain comprising an amino acid sequence that is at least 96% identical to SEQ ID NO: 54 and comprising the light chain CDR set of SEQ ID Nos: 234, 235 and 236; a light chain variable domain comprising an amino acid sequence that is at least 96% identical to SEQ ID NO: 56 and comprising the light chain CDR set of SEQ ID Nos: 240, 241 and 242; a light chain variable domain comprising an amino acid sequence that is at least 96% identical to SEQ ID NO: 58 and comprising the light chain CDR set of SEQ ID Nos: 246, 247 and 248; a light chain variable domain comprising an amino acid sequence that is at least 96% identical to SEQ ID NO: 60 and comprising the light chain CDR set of SEQ ID Nos: 252, 253 and 254; a light chain variable domain comprising an amino acid sequence that is at least 96% identical to SEQ ID NO: 62 and comprising the light chain CDR set of SEQ ID Nos: 258, 259 and 260; a light chain variable domain comprising an amino acid sequence that is at least 96% identical to SEQ ID NO: 64 and comprising the light chain CDR set of SEQ ID Nos: 264, 265 and 266; a light chain variable domain comprising an amino acid sequence that is at least 96% identical to SEQ ID NO: 66 and comprising the light chain CDR set of SEQ ID Nos: 270, 271 and 272; a light chain variable domain comprising an amino acid sequence that is at least 96% identical to SEQ ID NO: 68 and comprising the light chain CDR set of SEQ ID Nos: 276, 277 and 278; a light chain variable domain comprising an amino acid sequence that is at least 96% identical to SEQ ID NO: 70 and comprising the light chain CDR set of SEQ ID Nos: 282, 283 and 284; a light chain variable domain comprising an amino acid sequence that is at least 96% identical to SEQ ID NO: 72 and comprising the light chain CDR set of SEQ ID Nos: 288, 289 and 290; a light chain variable domain comprising an amino acid sequence that is at least 96% identical to SEQ ID NO: 74 and comprising the light chain CDR set of SEQ ID Nos: 294, 295 and 296; and a light chain variable domain comprising an amino acid sequence that is at least 95% identical to SEQ ID NO: 298 and comprising the light chain CDR set of SEQ ID Nos: 302, 303 and 304. In another embodiment, the heavy chain variable domain is selected from the group consisting of a heavy chain variable domain comprising an amino acid sequence that is at least 97% identical to SEQ ID NO: 1 and comprising the heavy chain CDR set of SEQ ID Nos: 75, 76, and 77; a heavy chain variable domain comprising an amino acid sequence that is at least 97% identical to SEQ ID NO: 3 and comprising the heavy chain CDR set of SEQ ID Nos: 81, 82 and 83; a heavy chain variable domain comprising an amino acid sequence that is at least 97% identical to SEQ ID NO: 5 and comprising the heavy chain CDR set of SEQ ID Nos: 87, 88 and 89; a heavy chain variable domain comprising an amino acid sequence that is at least 97% identical to SEQ ID NO: 7 and comprising the heavy chain CDR set of SEQ ID Nos: 93, 94 and 95; a heavy chain variable domain comprising an amino acid sequence that is at least 97% identical to SEQ ID NO: 9 and comprising the heavy chain CDR set of SEQ ID Nos: 99, 100 and 101; a heavy chain variable domain comprising an amino acid sequence that is at least 97% identical to SEQ ID NO: 11 and comprising the heavy chain CDR set of SEQ ID Nos: 105, 106 and 107; a heavy chain variable domain comprising an amino acid sequence that is at least 97% identical to SEQ ID NO: 13 and comprising the heavy chain CDR set of SEQ ID Nos: 111, 112 and 113; a heavy chain variable domain comprising an amino acid sequence that is at least 97% identical to SEQ ID NO: 15 and comprising the heavy chain CDR set of SEQ ID Nos: 117, 118 and 119; a heavy chain variable domain comprising an amino acid sequence that is at least 97% identical to SEQ ID NO: 17 and comprising the heavy chain CDR set of SEQ ID Nos: 123, 124 and 125; a heavy chain variable domain comprising an amino acid sequence that is at least 97% identical to SEQ ID NO: 19 and comprising the heavy chain CDR set of SEQ ID Nos: 129, 130 and 131; a heavy chain variable domain comprising an amino acid sequence that is at least 97% identical to SEQ ID NO: 21 and comprising the heavy chain CDR set of SEQ ID Nos: 135, 136 and 137; a heavy chain variable domain comprising an amino acid sequence that is at least 97% identical to SEQ ID NO: 23 and comprising the heavy chain CDR set of SEQ ID Nos: 141, 142 and 143; a heavy chain variable domain comprising an amino acid sequence that is at least 97% identical to SEQ ID NO: 25 and comprising the heavy chain CDR set of SEQ ID Nos: 147, 148 and 149; a heavy chain variable domain comprising an amino acid sequence that is at least 97% identical to SEQ ID NO: 27 and comprising the heavy chain CDR set of SEQ ID Nos: 153, 154 and 155; a heavy chain variable domain comprising an amino acid sequence that is at least 97% identical to SEQ ID NO: 29 and comprising the heavy chain CDR set of SEQ ID Nos: 159, 160 and 161; a heavy chain variable domain comprising an amino acid sequence that is at least 97% identical to SEQ ID NO: 31 and comprising the heavy chain CDR set of SEQ ID Nos: 165, 166 and 167; a heavy chain variable domain comprising an amino acid sequence that is at least 97% identical to SEQ ID NO: 33 and comprising the heavy chain CDR set of SEQ ID Nos: 171, 172 and 173; a heavy chain variable domain comprising an amino acid sequence that is at least 97% identical to SEQ ID NO: 35 and comprising the heavy chain CDR set of SEQ ID Nos: 177, 178 and 179; a heavy chain variable domain comprising an amino acid sequence that is at least 97% identical to SEQ ID NO: 37 and comprising the heavy chain CDR set of SEQ ID Nos: 183, 184 and 185; a heavy chain variable domain comprising an amino acid sequence that is at least 97% identical to SEQ ID NO: 39 and comprising the heavy chain CDR set of SEQ ID Nos: 189, 190 and 191; a heavy chain variable domain comprising an amino acid sequence that is at least 97% identical to SEQ ID NO: 41 and comprising the heavy chain CDR set of SEQ ID Nos: 195, 196 and 197; a heavy chain variable domain comprising an amino acid sequence that is at least 97% identical to SEQ ID NO: 43 and comprising the heavy chain CDR set of SEQ ID Nos: 201, 202 and 203; a heavy chain variable domain comprising an amino acid sequence that is at least 97% identical to SEQ ID NO: 45 and comprising the heavy chain CDR set of SEQ ID Nos: 207, 208 and 209; a heavy chain variable domain comprising an amino acid sequence that is at least 97% identical to SEQ ID NO: 47 and comprising the heavy chain CDR set of SEQ ID Nos: 213, 214 and 215; a heavy chain variable domain comprising an amino acid sequence that is at least 97% identical to SEQ ID NO: 49 and comprising the heavy chain CDR set of SEQ ID Nos: 219, 220 and 221; a heavy chain variable domain comprising an amino acid sequence that is at least 97% identical to SEQ ID NO: 51 and comprising the heavy chain CDR set of SEQ ID Nos: 225, 226 and 227; a heavy chain variable domain comprising an amino acid sequence that is at least 97% identical to SEQ ID NO: 53 and comprising the heavy chain CDR set of SEQ ID Nos: 231, 232 and 233; a heavy chain variable domain comprising an amino acid sequence that is at least 97% identical to SEQ ID NO: 55 and comprising the heavy chain CDR set of SEQ ID Nos: 237, 238 and 239; a heavy chain variable domain comprising an amino acid sequence that is at least 97% identical to SEQ ID NO: 57 and comprising the heavy chain CDR set of SEQ ID Nos: 243, 244 and 245; a heavy chain variable domain comprising an amino acid sequence that is at least 97% identical to SEQ ID NO: 59 and comprising the heavy chain CDR set of SEQ ID Nos: 249, 250 and 251; a heavy chain variable domain comprising an amino acid sequence that is at least 97% identical to SEQ ID NO: 61 and comprising the heavy chain CDR set of SEQ ID Nos: 255, 256 and 257; a heavy chain variable domain comprising an amino acid sequence that is at least 97% identical to SEQ ID NO: 63 and comprising the heavy chain CDR set of SEQ ID Nos: 261, 262 and 263; a heavy chain variable domain comprising an amino acid sequence that is at least 97% identical to SEQ ID NO: 65 and comprising the heavy chain CDR set of SEQ ID Nos: 267, 268 and 269; a heavy chain variable domain comprising an amino acid sequence that is at least 97% identical to SEQ ID NO: 67 and comprising the heavy chain CDR set of SEQ ID Nos: 273, 274 and 275; a heavy chain variable domain comprising an amino acid sequence that is at least 97% identical to SEQ ID NO: 69 and comprising the heavy chain CDR set of SEQ ID Nos: 279, 280 and 281; a heavy chain variable domain comprising an amino acid sequence that is at least 97% identical to SEQ ID NO: 71 and comprising the heavy chain CDR set of SEQ ID Nos: 285, 286 and 287; a heavy chain variable domain comprising an amino acid sequence that is at least 97% identical to SEQ ID NO: 73 and comprising the heavy chain CDR set of SEQ ID Nos: 291, 292 and 293; and a heavy chain variable domain comprising an amino acid sequence that is at least 95% identical to SEQ ID NO: 297 and comprising the heavy chain CDR set of SEQ ID Nos: 299, 300 and 301. In one embodiment of any one of the above aspects or embodiments, the light chain variable domain is selected from the group consisting of a light chain variable domain comprising an amino acid sequence that is at least 97% identical to SEQ ID NO: 2 and comprising the light chain CDR set of SEQ ID Nos: 78, 79 and 80; a light chain variable domain comprising an amino acid sequence that is at least 97% identical to SEQ ID NO: 4 and comprising the light chain CDR set of SEQ ID Nos: 84, 85 and 86; a light chain variable domain comprising an amino acid sequence that is at least 97% identical to SEQ ID NO: 6 and comprising the light chain CDR set of SEQ ID Nos: 90, 91 and 92; a light chain variable domain comprising an amino acid sequence that is at least 97% identical to SEQ ID NO: 8 and comprising the light chain CDR set of SEQ ID Nos: 96, 97 and 98; a light chain variable domain comprising an amino acid sequence that is at least 97% identical to SEQ ID NO: 10 and comprising the light chain CDR set of SEQ ID Nos: 102, 103 and 104; a light chain variable domain comprising an amino acid sequence that is at least 97% identical to SEQ ID NO: 12 and comprising the light chain CDR set of SEQ ID Nos: 108, 109 and 110; a light chain variable domain comprising an amino acid sequence that is at least 97% identical to SEQ ID NO: 14 and comprising the light chain CDR set of SEQ ID Nos: 114, 115 and 116; a light chain variable domain comprising an amino acid sequence that is at least 97% identical to SEQ ID NO: 16 and comprising the light chain CDR set of SEQ ID Nos: 120, 121 and 122; a light chain variable domain comprising an amino acid sequence that is at least 97% identical to SEQ ID NO: 18 and comprising the light chain CDR set of SEQ ID Nos: 126, 127 and 128; a light chain variable domain comprising an amino acid sequence that is at least 97% identical to SEQ ID NO: 20 and comprising the light chain CDR set of SEQ ID Nos: 132, 133 and 134; a light chain variable domain comprising an amino acid sequence that is at least 97% identical to SEQ ID NO: 22 and comprising the light chain CDR set of SEQ ID Nos: 138, 139 and 140; a light chain variable domain comprising an amino acid sequence that is at least 97% identical to SEQ ID NO: 24 and comprising the light chain CDR set of SEQ ID Nos: 144, 145 and 146; a light chain variable domain comprising an amino acid sequence that is at least 97% identical to SEQ ID NO: 26 and comprising the light chain CDR set of SEQ ID Nos: 150, 151 and 152; a light chain variable domain comprising an amino acid sequence that is at least 97% identical to SEQ ID NO: 28 and comprising the light chain CDR set of SEQ ID Nos: 156, 157 and 158; a light chain variable domain comprising an amino acid sequence that is at least 97% identical to SEQ ID NO: 30 and comprising the light chain CDR set of SEQ ID Nos: 163, 163 and 164; a light chain variable domain comprising an amino acid sequence that is at least 97% identical to SEQ ID NO: 32 and comprising the light chain CDR set of SEQ ID Nos: 168, 169 and 170; a light chain variable domain comprising an amino acid sequence that is at least 97% identical to SEQ ID NO: 34 and comprising the light chain CDR set of SEQ ID Nos: 174, 175 and 176; a light chain variable domain comprising an amino acid sequence that is at least 97% identical to SEQ ID NO: 36 and comprising the light chain CDR set of SEQ ID Nos: 180, 181 and 182; a light chain variable domain comprising an amino acid sequence that is at least 97% identical to SEQ ID NO: 38 and comprising the light chain CDR set of SEQ ID Nos: 186, 187 and 188; a light chain variable domain comprising an amino acid sequence that is at least 97% identical to SEQ ID NO: 40 and comprising the light chain CDR set of SEQ ID Nos: 192, 193 and 194; a light chain variable domain comprising an amino acid sequence that is at least 97% identical to SEQ ID NO: 42 and comprising the light chain CDR set of SEQ ID Nos: 198, 199 and 200; a light chain variable domain comprising an amino acid sequence that is at least 97% identical to SEQ ID NO: 44 and comprising the light chain CDR set of SEQ ID Nos: 204, 205 and 206; a light chain variable domain comprising an amino acid sequence that is at least 97% identical to SEQ ID NO: 46 and comprising the light chain CDR set of SEQ ID Nos: 210, 211 and 212; a light chain variable domain comprising an amino acid sequence that is at least 97% identical to SEQ ID NO: 48 and comprising the light chain CDR set of SEQ ID Nos: 216, 217 and 218; a light chain variable domain comprising an amino acid sequence that is at least 97% identical to SEQ ID NO: 50 and comprising the light chain CDR set of SEQ ID Nos: 222, 223 and 224; a light chain variable domain comprising an amino acid sequence that is at least 97% identical to SEQ ID NO: 52 and comprising the light chain CDR set of SEQ ID Nos: 228, 229 and 227; a light chain variable domain comprising an amino acid sequence that is at least 97% identical to SEQ ID NO: 54 and comprising the light chain CDR set of SEQ ID Nos: 234, 235 and 236; a light chain variable domain comprising an amino acid sequence that is at least 97% identical to SEQ ID NO: 56 and comprising the light chain CDR set of SEQ ID Nos: 240, 241 and 242; a light chain variable domain comprising an amino acid sequence that is at least 97% identical to SEQ ID NO: 58 and comprising the light chain CDR set of SEQ ID Nos: 246, 247 and 248; a light chain variable domain comprising an amino acid sequence that is at least 97% identical to SEQ ID NO: 60 and comprising the light chain CDR set of SEQ ID Nos: 252, 253 and 254; a light chain variable domain comprising an amino acid sequence that is at least 97% identical to SEQ ID NO: 62 and comprising the light chain CDR set of SEQ ID Nos: 258, 259 and 260; a light chain variable domain comprising an amino acid sequence that is at least 97% identical to SEQ ID NO: 64 and comprising the light chain CDR set of SEQ ID Nos: 264, 265 and 266; a light chain variable domain comprising an amino acid sequence that is at least 97% identical to SEQ ID NO: 66 and comprising the light chain CDR set of SEQ ID Nos: 270, 271 and 272; a light chain variable domain comprising an amino acid sequence that is at least 97% identical to SEQ ID NO: 68 and comprising the light chain CDR set of SEQ ID Nos: 276, 277 and 278; a light chain variable domain comprising an amino acid sequence that is at least 97% identical to SEQ ID NO: 70 and comprising the light chain CDR set of SEQ ID Nos: 282, 283 and 284; a light chain variable domain comprising an amino acid sequence that is at least 97% identical to SEQ ID NO: 72 and comprising the light chain CDR set of SEQ ID Nos: 288, 289 and 290; a light chain variable domain comprising an amino acid sequence that is at least 97% identical to SEQ ID NO: 74 and comprising the light chain CDR set of SEQ ID Nos: 294, 295 and 296; and a light chain variable domain comprising an amino acid sequence that is at least 95% identical to SEQ ID NO: 298 and comprising the light chain CDR set of SEQ ID Nos: 302, 303 and 304. In another embodiment of any one of the above aspects or embodiments, the heavy chain variable domain is selected from the group consisting of a heavy chain variable domain comprising an amino acid sequence that is at least 98% identical to SEQ ID NO: 1 and comprising the heavy chain CDR set of SEQ ID Nos: 75, 76, and 77; a heavy chain variable domain comprising an amino acid sequence that is at least 98% identical to SEQ ID NO: 3 and comprising the heavy chain CDR set of SEQ ID Nos: 81, 82 and 83; a heavy chain variable domain comprising an amino acid sequence that is at least 98% identical to SEQ ID NO: 5 and comprising the heavy chain CDR set of SEQ ID Nos: 87, 88 and 89; a heavy chain variable domain comprising an amino acid sequence that is at least 98% identical to SEQ ID NO: 7 and comprising the heavy chain CDR set of SEQ ID Nos: 93, 94 and 95; a heavy chain variable domain comprising an amino acid sequence that is at least 98% identical to SEQ ID NO: 9 and comprising the heavy chain CDR set of SEQ ID Nos: 99, 100 and 101; a heavy chain variable domain comprising an amino acid sequence that is at least 98% identical to SEQ ID NO: 11 and comprising the heavy chain CDR set of SEQ ID Nos: 105, 106 and 107; a heavy chain variable domain comprising an amino acid sequence that is at least 98% identical to SEQ ID NO: 13 and comprising the heavy chain CDR set of SEQ ID Nos: 111, 112 and 113; a heavy chain variable domain comprising an amino acid sequence that is at least 98% identical to SEQ ID NO: 15 and comprising the heavy chain CDR set of SEQ ID Nos: 117, 118 and 119; a heavy chain variable domain comprising an amino acid sequence that is at least 98% identical to SEQ ID NO: 17 and comprising the heavy chain CDR set of SEQ ID Nos: 123, 124 and 125; a heavy chain variable domain comprising an amino acid sequence that is at least 98% identical to SEQ ID NO: 19 and comprising the heavy chain CDR set of SEQ ID Nos: 129, 130 and 131; a heavy chain variable domain comprising an amino acid sequence that is at least 98% identical to SEQ ID NO: 21 and comprising the heavy chain CDR set of SEQ ID Nos: 135, 136 and 137; a heavy chain variable domain comprising an amino acid sequence that is at least 98% identical to SEQ ID NO: 23 and comprising the heavy chain CDR set of SEQ ID Nos: 141, 142 and 143; a heavy chain variable domain comprising an amino acid sequence that is at least 98% identical to SEQ ID NO: 25 and comprising the heavy chain CDR set of SEQ ID Nos: 147, 148 and 149; a heavy chain variable domain comprising an amino acid sequence that is at least 98% identical to SEQ ID NO: 27 and comprising the heavy chain CDR set of SEQ ID Nos: 153, 154 and 155; a heavy chain variable domain comprising an amino acid sequence that is at least 98% identical to SEQ ID NO: 29 and comprising the heavy chain CDR set of SEQ ID Nos: 159, 160 and 161; a heavy chain variable domain comprising an amino acid sequence that is at least 98% identical to SEQ ID NO: 31 and comprising the heavy chain CDR set of SEQ ID Nos: 165, 166 and 167; a heavy chain variable domain comprising an amino acid sequence that is at least 98% identical to SEQ ID NO: 33 and comprising the heavy chain CDR set of SEQ ID Nos: 171, 172 and 173; a heavy chain variable domain comprising an amino acid sequence that is at least 98% identical to SEQ ID NO: 35 and comprising the heavy chain CDR set of SEQ ID Nos: 177, 178 and 179; a heavy chain variable domain comprising an amino acid sequence that is at least 98% identical to SEQ ID NO: 37 and comprising the heavy chain CDR set of SEQ ID Nos: 183, 184 and 185; a heavy chain variable domain comprising an amino acid sequence that is at least 98% identical to SEQ ID NO: 39 and comprising the heavy chain CDR set of SEQ ID Nos: 189, 190 and 191; a heavy chain variable domain comprising an amino acid sequence that is at least 98% identical to SEQ ID NO: 41 and comprising the heavy chain CDR set of SEQ ID Nos: 195, 196 and 197; a heavy chain variable domain comprising an amino acid sequence that is at least 98% identical to SEQ ID NO: 43 and comprising the heavy chain CDR set of SEQ ID Nos: 201, 202 and 203; a heavy chain variable domain comprising an amino acid sequence that is at least 98% identical to SEQ ID NO: 45 and comprising the heavy chain CDR set of SEQ ID Nos: 207, 208 and 209; a heavy chain variable domain comprising an amino acid sequence that is at least 98% identical to SEQ ID NO: 47 and comprising the heavy chain CDR set of SEQ ID Nos: 213, 214 and 215; a heavy chain variable domain comprising an amino acid sequence that is at least 98% identical to SEQ ID NO: 49 and comprising the heavy chain CDR set of SEQ ID Nos: 219, 220 and 221; a heavy chain variable domain comprising an amino acid sequence that is at least 98% identical to SEQ ID NO: 51 and comprising the heavy chain CDR set of SEQ ID Nos: 225, 226 and 227; a heavy chain variable domain comprising an amino acid sequence that is at least 98% identical to SEQ ID NO: 53 and comprising the heavy chain CDR set of SEQ ID Nos: 231, 232 and 233; a heavy chain variable domain comprising an amino acid sequence that is at least 98% identical to SEQ ID NO: 55 and comprising the heavy chain CDR set of SEQ ID Nos: 237, 238 and 239; a heavy chain variable domain comprising an amino acid sequence that is at least 98% identical to SEQ ID NO: 57 and comprising the heavy chain CDR set of SEQ ID Nos: 243, 244 and 245; a heavy chain variable domain comprising an amino acid sequence that is at least 98% identical to SEQ ID NO: 59 and comprising the heavy chain CDR set of SEQ ID Nos: 249, 250 and 251; a heavy chain variable domain comprising an amino acid sequence that is at least 98% identical to SEQ ID NO: 61 and comprising the heavy chain CDR set of SEQ ID Nos: 255, 256 and 257; a heavy chain variable domain comprising an amino acid sequence that is at least 98% identical to SEQ ID NO: 63 and comprising the heavy chain CDR set of SEQ ID Nos: 261, 262 and 263; a heavy chain variable domain comprising an amino acid sequence that is at least 98% identical to SEQ ID NO: 65 and comprising the heavy chain CDR set of SEQ ID Nos: 267, 268 and 269; a heavy chain variable domain comprising an amino acid sequence that is at least 98% identical to SEQ ID NO: 67 and comprising the heavy chain CDR set of SEQ ID Nos: 273, 274 and 275; a heavy chain variable domain comprising an amino acid sequence that is at least 98% identical to SEQ ID NO: 69 and comprising the heavy chain CDR set of SEQ ID Nos: 279, 280 and 281; a heavy chain variable domain comprising an amino acid sequence that is at least 98% identical to SEQ ID NO: 71 and comprising the heavy chain CDR set of SEQ ID Nos: 285, 286 and 287; a heavy chain variable domain comprising an amino acid sequence that is at least 98% identical to SEQ ID NO: 73 and comprising the heavy chain CDR set of SEQ ID Nos: 291, 292 and 293; and a heavy chain variable domain comprising an amino acid sequence that is at least 98% identical to SEQ ID NO: 297 and comprising the heavy chain CDR set of SEQ ID Nos: 299, 300 and 301. In another embodiment of any one of the above aspects or embodiments, the light chain variable domain is selected from the group consisting of a light chain variable domain comprising an amino acid sequence that is at least 98% identical to SEQ ID NO: 2 and comprising the light chain CDR set of SEQ ID Nos: 78, 79 and 80; a light chain variable domain comprising an amino acid sequence that is at least 98% identical to SEQ ID NO: 4 and comprising the light chain CDR set of SEQ ID Nos: 84, 85 and 86; a light chain variable domain comprising an amino acid sequence that is at least 98% identical to SEQ ID NO: 6 and comprising the light chain CDR set of SEQ ID Nos: 90, 91 and 92; a light chain variable domain comprising an amino acid sequence that is at least 98% identical to SEQ ID NO: 8 and comprising the light chain CDR set of SEQ ID Nos: 96, 97 and 98; a light chain variable domain comprising an amino acid sequence that is at least 98% identical to SEQ ID NO: 10 and comprising the light chain CDR set of SEQ ID Nos: 102, 103 and 104; a light chain variable domain comprising an amino acid sequence that is at least 98% identical to SEQ ID NO: 12 and comprising the light chain CDR set of SEQ ID Nos: 108, 109 and 110; a light chain variable domain comprising an amino acid sequence that is at least 98% identical to SEQ ID NO: 14 and comprising the light chain CDR set of SEQ ID Nos: 114, 115 and 116; a light chain variable domain comprising an amino acid sequence that is at least 98% identical to SEQ ID NO: 16 and comprising the light chain CDR set of SEQ ID Nos: 120, 121 and 122; a light chain variable domain comprising an amino acid sequence that is at least 98% identical to SEQ ID NO: 18 and comprising the light chain CDR set of SEQ ID Nos: 126, 127 and 128; a light chain variable domain comprising an amino acid sequence that is at least 98% identical to SEQ ID NO: 20 and comprising the light chain CDR set of SEQ ID Nos: 132, 133 and 134; a light chain variable domain comprising an amino acid sequence that is at least 98% identical to SEQ ID NO: 22 and comprising the light chain CDR set of SEQ ID Nos: 138, 139 and 140; a light chain variable domain comprising an amino acid sequence that is at least 98% identical to SEQ ID NO: 24 and comprising the light chain CDR set of SEQ ID Nos: 144, 145 and 146; a light chain variable domain comprising an amino acid sequence that is at least 98% identical to SEQ ID NO: 26 and comprising the light chain CDR set of SEQ ID Nos: 150, 151 and 152; a light chain variable domain comprising an amino acid sequence that is at least 98% identical to SEQ ID NO: 28 and comprising the light chain CDR set of SEQ ID Nos: 156, 157 and 158; a light chain variable domain comprising an amino acid sequence that is at least 98% identical to SEQ ID NO: 30 and comprising the light chain CDR set of SEQ ID Nos: 163, 163 and 164; a light chain variable domain comprising an amino acid sequence that is at least 98% identical to SEQ ID NO: 32 and comprising the light chain CDR set of SEQ ID Nos: 168, 169 and 170; a light chain variable domain comprising an amino acid sequence that is at least 98% identical to SEQ ID NO: 34 and comprising the light chain CDR set of SEQ ID Nos: 174, 175 and 176; a light chain variable domain comprising an amino acid sequence that is at least 98% identical to SEQ ID NO: 36 and comprising the light chain CDR set of SEQ ID Nos: 180, 181 and 182; a light chain variable domain comprising an amino acid sequence that is at least 98% identical to SEQ ID NO: 38 and comprising the light chain CDR set of SEQ ID Nos: 186, 187 and 188; a light chain variable domain comprising an amino acid sequence that is at least 98% identical to SEQ ID NO: 40 and comprising the light chain CDR set of SEQ ID Nos: 192, 193 and 194; a light chain variable domain comprising an amino acid sequence that is at least 98% identical to SEQ ID NO: 42 and comprising the light chain CDR set of SEQ ID Nos: 198, 199 and 200; a light chain variable domain comprising an amino acid sequence that is at least 98% identical to SEQ ID NO: 44 and comprising the light chain CDR set of SEQ ID Nos: 204, 205 and 206; a light chain variable domain comprising an amino acid sequence that is at least 98% identical to SEQ ID NO: 46 and comprising the light chain CDR set of SEQ ID Nos: 210, 211 and 212; a light chain variable domain comprising an amino acid sequence that is at least 98% identical to SEQ ID NO: 48 and comprising the light chain CDR set of SEQ ID Nos: 216, 217 and 218; a light chain variable domain comprising an amino acid sequence that is at least 98% identical to SEQ ID NO: 50 and comprising the light chain CDR set of SEQ ID Nos: 222, 223 and 224; a light chain variable domain comprising an amino acid sequence that is at least 98% identical to SEQ ID NO: 52 and comprising the light chain CDR set of SEQ ID Nos: 228, 229 and 227; a light chain variable domain comprising an amino acid sequence that is at least 98% identical to SEQ ID NO: 54 and comprising the light chain CDR set of SEQ ID Nos: 234, 235 and 236; a light chain variable domain comprising an amino acid sequence that is at least 98% identical to SEQ ID NO: 56 and comprising the light chain CDR set of SEQ ID Nos: 240, 241 and 242; a light chain variable domain comprising an amino acid sequence that is at least 98% identical to SEQ ID NO: 58 and comprising the light chain CDR set of SEQ ID Nos: 246, 247 and 248; a light chain variable domain comprising an amino acid sequence that is at least 98% identical to SEQ ID NO: 60 and comprising the light chain CDR set of SEQ ID Nos: 252, 253 and 254; a light chain variable domain comprising an amino acid sequence that is at least 98% identical to SEQ ID NO: 62 and comprising the light chain CDR set of SEQ ID Nos: 258, 259 and 260; a light chain variable domain comprising an amino acid sequence that is at least 98% identical to SEQ ID NO: 64 and comprising the light chain CDR set of SEQ ID Nos: 264, 265 and 266; a light chain variable domain comprising an amino acid sequence that is at least 98% identical to SEQ ID NO: 66 and comprising the light chain CDR set of SEQ ID Nos: 270, 271 and 272; a light chain variable domain comprising an amino acid sequence that is at least 98% identical to SEQ ID NO: 68 and comprising the light chain CDR set of SEQ ID Nos: 276, 277 and 278; a light chain variable domain comprising an amino acid sequence that is at least 98% identical to SEQ ID NO: 70 and comprising the light chain CDR set of SEQ ID Nos: 282, 283 and 284; a light chain variable domain comprising an amino acid sequence that is at least 98% identical to SEQ ID NO: 72 and comprising the light chain CDR set of SEQ ID Nos: 288, 289 and 290; a light chain variable domain comprising an amino acid sequence that is at least 98% identical to SEQ ID NO: 74 and comprising the light chain CDR set of SEQ ID Nos: 294, 295 and 296; and a light chain variable domain comprising an amino acid sequence that is at least 98% identical to SEQ ID NO: 298 and comprising the light chain CDR set of SEQ ID Nos: 302, 303 and 304. In another embodiment of any one of the above aspects or embodiments, the heavy chain variable domain is selected from the group consisting of a heavy chain variable domain comprising an amino acid sequence that is at least 99% identical to SEQ ID NO: 1 and comprising the heavy chain CDR set of SEQ ID Nos: 75, 76, and 77; a heavy chain variable domain comprising an amino acid sequence that is at least 99% identical to SEQ ID NO: 3 and comprising the heavy chain CDR set of SEQ ID Nos: 81, 82 and 83; a heavy chain variable domain comprising an amino acid sequence that is at least 99% identical to SEQ ID NO: 5 and comprising the heavy chain CDR set of SEQ ID Nos: 87, 88 and 89; a heavy chain variable domain comprising an amino acid sequence that is at least 99% identical to SEQ ID NO: 7 and comprising the heavy chain CDR set of SEQ ID Nos: 93, 94 and 95; a heavy chain variable domain comprising an amino acid sequence that is at least 99% identical to SEQ ID NO: 9 and comprising the heavy chain CDR set of SEQ ID Nos: 99, 100 and 101; a heavy chain variable domain comprising an amino acid sequence that is at least 99% identical to SEQ ID NO: 11 and comprising the heavy chain CDR set of SEQ ID Nos: 105, 106 and 107; a heavy chain variable domain comprising an amino acid sequence that is at least 99% identical to SEQ ID NO: 13 and comprising the heavy chain CDR set of SEQ ID Nos: 111, 112 and 113; a heavy chain variable domain comprising an amino acid sequence that is at least 99% identical to SEQ ID NO: 15 and comprising the heavy chain CDR set of SEQ ID Nos: 117, 118 and 119; a heavy chain variable domain comprising an amino acid sequence that is at least 99% identical to SEQ ID NO: 17 and comprising the heavy chain CDR set of SEQ ID Nos: 123, 124 and 125; a heavy chain variable domain comprising an amino acid sequence that is at least 99% identical to SEQ ID NO: 19 and comprising the heavy chain CDR set of SEQ ID Nos: 129, 130 and 131; a heavy chain variable domain comprising an amino acid sequence that is at least 99% identical to SEQ ID NO: 21 and comprising the heavy chain CDR set of SEQ ID Nos: 135, 136 and 137; a heavy chain variable domain comprising an amino acid sequence that is at least 99% identical to SEQ ID NO: 23 and comprising the heavy chain CDR set of SEQ ID Nos: 141, 142 and 143; a heavy chain variable domain comprising an amino acid sequence that is at least 99% identical to SEQ ID NO: 25 and comprising the heavy chain CDR set of SEQ ID Nos: 147, 148 and 149; a heavy chain variable domain comprising an amino acid sequence that is at least 99% identical to SEQ ID NO: 27 and comprising the heavy chain CDR set of SEQ ID Nos: 153, 154 and 155; a heavy chain variable domain comprising an amino acid sequence that is at least 99% identical to SEQ ID NO: 29 and comprising the heavy chain CDR set of SEQ ID Nos: 159, 160 and 161; a heavy chain variable domain comprising an amino acid sequence that is at least 99% identical to SEQ ID NO: 31 and comprising the heavy chain CDR set of SEQ ID Nos: 165, 166 and 167; a heavy chain variable domain comprising an amino acid sequence that is at least 99% identical to SEQ ID NO: 33 and comprising the heavy chain CDR set of SEQ ID Nos: 171, 172 and 173; a heavy chain variable domain comprising an amino acid sequence that is at least 99% identical to SEQ ID NO: 35 and comprising the heavy chain CDR set of SEQ ID Nos: 177, 178 and 179; a heavy chain variable domain comprising an amino acid sequence that is at least 99% identical to SEQ ID NO: 37 and comprising the heavy chain CDR set of SEQ ID Nos: 183, 184 and 185; a heavy chain variable domain comprising an amino acid sequence that is at least 99% identical to SEQ ID NO: 39 and comprising the heavy chain CDR set of SEQ ID Nos: 189, 190 and 191; a heavy chain variable domain comprising an amino acid sequence that is at least 99% identical to SEQ ID NO: 41 and comprising the heavy chain CDR set of SEQ ID Nos: 195, 196 and 197; a heavy chain variable domain comprising an amino acid sequence that is at least 99% identical to SEQ ID NO: 43 and comprising the heavy chain CDR set of SEQ ID Nos: 201, 202 and 203; a heavy chain variable domain comprising an amino acid sequence that is at least 99% identical to SEQ ID NO: 45 and comprising the heavy chain CDR set of SEQ ID Nos: 207, 208 and 209; a heavy chain variable domain comprising an amino acid sequence that is at least 99% identical to SEQ ID NO: 47 and comprising the heavy chain CDR set of SEQ ID Nos: 213, 214 and 215; a heavy chain variable domain comprising an amino acid sequence that is at least 99% identical to SEQ ID NO: 49 and comprising the heavy chain CDR set of SEQ ID Nos: 219, 220 and 221; a heavy chain variable domain comprising an amino acid sequence that is at least 99% identical to SEQ ID NO: 51 and comprising the heavy chain CDR set of SEQ ID Nos: 225, 226 and 227; a heavy chain variable domain comprising an amino acid sequence that is at least 99% identical to SEQ ID NO: 53 and comprising the heavy chain CDR set of SEQ ID Nos: 231, 232 and 233; a heavy chain variable domain comprising an amino acid sequence that is at least 99% identical to SEQ ID NO: 55 and comprising the heavy chain CDR set of SEQ ID Nos: 237, 238 and 239; a heavy chain variable domain comprising an amino acid sequence that is at least 99% identical to SEQ ID NO: 57 and comprising the heavy chain CDR set of SEQ ID Nos: 243, 244 and 245; a heavy chain variable domain comprising an amino acid sequence that is at least 99% identical to SEQ ID NO: 59 and comprising the heavy chain CDR set of SEQ ID Nos: 249, 250 and 251; a heavy chain variable domain comprising an amino acid sequence that is at least 99% identical to SEQ ID NO: 61 and comprising the heavy chain CDR set of SEQ ID Nos: 255, 256 and 257; a heavy chain variable domain comprising an amino acid sequence that is at least 99% identical to SEQ ID NO: 63 and comprising the heavy chain CDR set of SEQ ID Nos: 261, 262 and 263; a heavy chain variable domain comprising an amino acid sequence that is at least 99% identical to SEQ ID NO: 65 and comprising the heavy chain CDR set of SEQ ID Nos: 267, 268 and 269; a heavy chain variable domain comprising an amino acid sequence that is at least 99% identical to SEQ ID NO: 67 and comprising the heavy chain CDR set of SEQ ID Nos: 273, 274 and 275; a heavy chain variable domain comprising an amino acid sequence that is at least 99% identical to SEQ ID NO: 69 and comprising the heavy chain CDR set of SEQ ID Nos: 279, 280 and 281; a heavy chain variable domain comprising an amino acid sequence that is at least 99% identical to SEQ ID NO: 71 and comprising the heavy chain CDR set of SEQ ID Nos: 285, 286 and 287; a heavy chain variable domain comprising an amino acid sequence that is at least 99% identical to SEQ ID NO: 73 and comprising the heavy chain CDR set of SEQ ID Nos: 291, 292 and 293; and a heavy chain variable domain comprising an amino acid sequence that is at least 99% identical to SEQ ID NO: 297 and comprising the heavy chain CDR set of SEQ ID Nos: 299, 300 and 301. In another embodiment of any one of the above aspects or embodiments, the light chain variable domain is selected from the group consisting of a light chain variable domain comprising an amino acid sequence that is at least 99% identical to SEQ ID NO: 2 and comprising the light chain CDR set of SEQ ID Nos: 78, 79 and 80; a light chain variable domain comprising an amino acid sequence that is at least 99% identical to SEQ ID NO: 4 and comprising the light chain CDR set of SEQ ID Nos: 84, 85 and 86; a light chain variable domain comprising an amino acid sequence that is at least 99% identical to SEQ ID NO: 6 and comprising the light chain CDR set of SEQ ID Nos: 90, 91 and 92; a light chain variable domain comprising an amino acid sequence that is at least 99% identical to SEQ ID NO: 8 and comprising the light chain CDR set of SEQ ID Nos: 96, 97 and 98; a light chain variable domain comprising an amino acid sequence that is at least 99% identical to SEQ ID NO: 10 and comprising the light chain CDR set of SEQ ID Nos: 102, 103 and 104; a light chain variable domain comprising an amino acid sequence that is at least 99% identical to SEQ ID NO: 12 and comprising the light chain CDR set of SEQ ID Nos: 108, 109 and 110; a light chain variable domain comprising an amino acid sequence that is at least 99% identical to SEQ ID NO: 14 and comprising the light chain CDR set of SEQ ID Nos: 114, 115 and 116; a light chain variable domain comprising an amino acid sequence that is at least 99% identical to SEQ ID NO: 16 and comprising the light chain CDR set of SEQ ID Nos: 120, 121 and 122; a light chain variable domain comprising an amino acid sequence that is at least 99% identical to SEQ ID NO: 18 and comprising the light chain CDR set of SEQ ID Nos: 126, 127 and 128; a light chain variable domain comprising an amino acid sequence that is at least 99% identical to SEQ ID NO: 20 and comprising the light chain CDR set of SEQ ID Nos: 132, 133 and 134; a light chain variable domain comprising an amino acid sequence that is at least 99% identical to SEQ ID NO: 22 and comprising the light chain CDR set of SEQ ID Nos: 138, 139 and 140; a light chain variable domain comprising an amino acid sequence that is at least 99% identical to SEQ ID NO: 24 and comprising the light chain CDR set of SEQ ID Nos: 144, 145 and 146; a light chain variable domain comprising an amino acid sequence that is at least 99% identical to SEQ ID NO: 26 and comprising the light chain CDR set of SEQ ID Nos: 150, 151 and 152; a light chain variable domain comprising an amino acid sequence that is at least 99% identical to SEQ ID NO: 28 and comprising the light chain CDR set of SEQ ID Nos: 156, 157 and 158; a light chain variable domain comprising an amino acid sequence that is at least 99% identical to SEQ ID NO: 30 and comprising the light chain CDR set of SEQ ID Nos: 163, 163 and 164; a light chain variable domain comprising an amino acid sequence that is at least 99% identical to SEQ ID NO: 32 and comprising the light chain CDR set of SEQ ID Nos: 168, 169 and 170; a light chain variable domain comprising an amino acid sequence that is at least 99% identical to SEQ ID NO: 34 and comprising the light chain CDR set of SEQ ID Nos: 174, 175 and 176; a light chain variable domain comprising an amino acid sequence that is at least 99% identical to SEQ ID NO: 36 and comprising the light chain CDR set of SEQ ID Nos: 180, 181 and 182; a light chain variable domain comprising an amino acid sequence that is at least 99% identical to SEQ ID NO: 38 and comprising the light chain CDR set of SEQ ID Nos: 186, 187 and 188; a light chain variable domain comprising an amino acid sequence that is at least 99% identical to SEQ ID NO: 40 and comprising the light chain CDR set of SEQ ID Nos: 192, 193 and 194; a light chain variable domain comprising an amino acid sequence that is at least 99% identical to SEQ ID NO: 42 and comprising the light chain CDR set of SEQ ID Nos: 198, 199 and 200; a light chain variable domain comprising an amino acid sequence that is at least 99% identical to SEQ ID NO: 44 and comprising the light chain CDR set of SEQ ID Nos: 204, 205 and 206; a light chain variable domain comprising an amino acid sequence that is at least 99% identical to SEQ ID NO: 46 and comprising the light chain CDR set of SEQ ID Nos: 210, 211 and 212; a light chain variable domain comprising an amino acid sequence that is at least 99% identical to SEQ ID NO: 48 and comprising the light chain CDR set of SEQ ID Nos: 216, 217 and 218; a light chain variable domain comprising an amino acid sequence that is at least 99% identical to SEQ ID NO: 50 and comprising the light chain CDR set of SEQ ID Nos: 222, 223 and 224; a light chain variable domain comprising an amino acid sequence that is at least 99% identical to SEQ ID NO: 52 and comprising the light chain CDR set of SEQ ID Nos: 228, 229 and 227; a light chain variable domain comprising an amino acid sequence that is at least 99% identical to SEQ ID NO: 54 and comprising the light chain CDR set of SEQ ID Nos: 234, 235 and 236; a light chain variable domain comprising an amino acid sequence that is at least 99% identical to SEQ ID NO: 56 and comprising the light chain CDR set of SEQ ID Nos: 240, 241 and 242; a light chain variable domain comprising an amino acid sequence that is at least 99% identical to SEQ ID NO: 58 and comprising the light chain CDR set of SEQ ID Nos: 246, 247 and 248; a light chain variable domain comprising an amino acid sequence that is at least 99% identical to SEQ ID NO: 60 and comprising the light chain CDR set of SEQ ID Nos: 252, 253 and 254; a light chain variable domain comprising an amino acid sequence that is at least 99% identical to SEQ ID NO: 62 and comprising the light chain CDR set of SEQ ID Nos: 258, 259 and 260; a light chain variable domain comprising an amino acid sequence that is at least 99% identical to SEQ ID NO: 64 and comprising the light chain CDR set of SEQ ID Nos: 264, 265 and 266; a light chain variable domain comprising an amino acid sequence that is at least 99% identical to SEQ ID NO: 66 and comprising the light chain CDR set of SEQ ID Nos: 270, 271 and 272; a light chain variable domain comprising an amino acid sequence that is at least 99% identical to SEQ ID NO: 68 and comprising the light chain CDR set of SEQ ID Nos: 276, 277 and 278; a light chain variable domain comprising an amino acid sequence that is at least 99% identical to SEQ ID NO: 70 and comprising the light chain CDR set of SEQ ID Nos: 282, 283 and 284; a light chain variable domain comprising an amino acid sequence that is at least 99% identical to SEQ ID NO: 72 and comprising the light chain CDR set of SEQ ID Nos: 288, 289 and 290; a light chain variable domain comprising an amino acid sequence that is at least 99% identical to SEQ ID NO: 74 and comprising the light chain CDR set of SEQ ID Nos: 294, 295 and 296; and a light chain variable domain comprising an amino acid sequence that is at least 99% identical to SEQ ID NO: 298 and comprising the light chain CDR set of SEQ ID Nos: 302, 303 and 304.

In one aspect, the invention features an isolated anti-KRAS antibody, or an antigen-binding fragment thereof, comprising a heavy chain variable domain comprising an amino acid sequence selected from the group consisting of: SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73 and SEQ ID NO. 297; and comprising a light chain variable domain comprising an amino acid sequence selected from the group consisting of: SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74 and SEQ ID NO. 298.

In one aspect, the invention features an isolated anti-KRAS antibody, or an antigen-binding fragment thereof, comprising a heavy chain variable domain comprising amino acid sequences of a heavy chain CDR set and a light chain variable domain comprising amino acid sequences of a light chain CDR set, wherein the heavy chain CDR set and the light chain CDR set are selected from the group consisting of a heavy chain variable domain CDR set of SEQ ID Nos: 75, 76 and 77 and a light chain variable domain CDR set of 78, 79 and 80; a heavy chain variable domain CDR set of SEQ ID Nos: 81, 82 and 83 and a light chain variable domain CDR set of 84, 85 and 86; a heavy chain variable domain CDR set of SEQ ID Nos: 87, 88 and 89 and a light chain variable domain CDR set of 90, 91 and 92; a heavy chain variable domain CDR set of SEQ ID Nos: 93, 94 and 95 and a light chain variable domain CDR set of 96, 97 and 98; a heavy chain variable domain CDR set of SEQ ID Nos: 99, 100 and 101 and a light chain variable domain CDR set of 102, 103 and 104; a heavy chain variable domain CDR set of SEQ ID Nos: 105, 106 and 107 and a light chain variable domain CDR set of 108, 109 and 110; a heavy chain variable domain CDR set of SEQ ID Nos: 111, 112 and 113 and a light chain variable domain CDR set of 114, 115 and 116; a heavy chain variable domain CDR set of SEQ ID Nos: 117, 118 and 119 and a light chain variable domain CDR set of 120, 121 and 122; a heavy chain variable domain CDR set of SEQ ID Nos: 123, 124 and 125 and a light chain variable domain CDR set of 126, 127 and 128; a heavy chain variable domain CDR set of SEQ ID Nos: 129, 130 and 131 and a light chain variable domain CDR set of 132, 133 and 134; a heavy chain variable domain CDR set of SEQ ID Nos: 135, 136 and 137 and a light chain variable domain CDR set of 138, 139 and 140; a heavy chain variable domain CDR set of SEQ ID Nos: 141, 142 and 143 and a light chain variable domain CDR set of 144, 145 and 146; a heavy chain variable domain CDR set of SEQ ID Nos: 147, 148 and 149 and a light chain variable domain CDR set of 150, 151 and 152; a heavy chain variable domain CDR set of SEQ ID Nos: 153, 154 and 155 and a light chain variable domain CDR set of 156, 157 and 158; a heavy chain variable domain CDR set of SEQ ID Nos: 159, 160 and 161 and a light chain variable domain CDR set of 162, 163 and 164; a heavy chain variable domain CDR set of SEQ ID Nos: 165, 166 and 167 and a light chain variable domain CDR set of 168, 169 and 170; a heavy chain variable domain CDR set of SEQ ID Nos: 171, 172 and 173 and a light chain variable domain CDR set of 174, 175 and 176; a heavy chain variable domain CDR set of SEQ ID Nos: 177, 178 and 179 and a light chain variable domain CDR set of 180, 181 and 182; a heavy chain variable domain CDR set of SEQ ID Nos: 183, 184 and 185 and a light chain variable domain CDR set of 186, 187 and 188; a heavy chain variable domain CDR set of SEQ ID Nos: 189, 190 and 191 and a light chain variable domain CDR set of 192, 193 and 194; a heavy chain variable domain CDR set of SEQ ID Nos: 195, 196 and 197 and a light chain variable domain CDR set of 198, 199 and 200; a heavy chain variable domain CDR set of SEQ ID Nos: 201, 202 and 203 and a light chain variable domain CDR set of 204, 205 and 206; a heavy chain variable domain CDR set of SEQ ID Nos: 207, 208 and 209 and a light chain variable domain CDR set of 210, 211 and 212; a heavy chain variable domain CDR set of SEQ ID Nos: 213, 1214 and 215 and a light chain variable domain CDR set of 216, 217 and 218; a heavy chain variable domain CDR set of SEQ ID Nos: 219, 220 and 221 and a light chain variable domain CDR set of 222, 223 and 224; a heavy chain variable domain CDR set of SEQ ID Nos: 225, 226 and 227 and a light chain variable domain CDR set of 228, 229 and 230; a heavy chain variable domain CDR set of SEQ ID Nos: 231, 232 and 233 and a light chain variable domain CDR set of 234, 235 and 236; a heavy chain variable domain CDR set of SEQ ID Nos: 237, 238 and 239 and a light chain variable domain CDR set of 240, 241 and 242; a heavy chain variable domain CDR set of SEQ ID Nos: 243, 244 and 245 and a light chain variable domain CDR set of 246, 247 and 248; a heavy chain variable domain CDR set of SEQ ID Nos: 249, 250 and 251 and a light chain variable domain CDR set of 252, 253 and 254; a heavy chain variable domain CDR set of SEQ ID Nos: 255, 256 and 257 and a light chain variable domain CDR set of 258, 259 and 260; a heavy chain variable domain CDR set of SEQ ID Nos: 261, 262 and 263 and a light chain variable domain CDR set of 1264, 265 and 266; a heavy chain variable domain CDR set of SEQ ID Nos: 267, 268 and 269 and a light chain variable domain CDR set of 270, 271 and 272; a heavy chain variable domain CDR set of SEQ ID Nos: 273, 274 and 275 and a light chain variable domain CDR set of 276, 277 and 278; a heavy chain variable domain CDR set of SEQ ID Nos: 279, 280 and 281 and a light chain variable domain CDR set of 282, 283 and 284; a heavy chain variable domain CDR set of SEQ ID Nos: 285, 286 and 287 and a light chain variable domain CDR set of 288, 289 and 290; a heavy chain variable domain CDR set of SEQ ID Nos: 291, 292 and 293 and a light chain variable domain CDR set of 294, 295 and 296; and a heavy chain variable domain CDR set of SEQ ID Nos: 299, 300 and 301 and a light chain variable domain CDR set of 302, 303 and 304.

In one aspect, the invention features an anti-KRAS antibody, or an antigen-binding fragment thereof, comprising a heavy chain variable domain comprising an amino acid sequence that is at least 95% identical to an amino acid sequence selected from the group consisting of: SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73 and SEQ ID NO. 297; and comprising a light chain variable domain comprising an amino acid sequence that is at least 95% identical to an amino acid sequence selected from the group consisting of: SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74 and SEQ ID NO. 298.

In one aspect, the invention features an anti-KRAS antibody, or an antigen-binding fragment thereof, comprising a heavy chain variable domain comprising an amino acid sequence that is at least 96% identical to an amino acid sequence selected from the group consisting of: SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73 and SEQ ID NO. 297; and comprising a light chain variable domain comprising an amino acid sequence that is at least 96% identical to an amino acid sequence selected from the group consisting of: SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74 and SEQ ID NO. 298.

In one aspect, the invention features an anti-KRAS antibody, or an antigen-binding fragment thereof, comprising a heavy chain variable domain comprising an amino acid sequence that is at least 97% identical to an amino acid sequence selected from the group consisting of: SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73 and SEQ ID NO. 297; and comprising a light chain variable domain comprising an amino acid sequence that is at least 97% identical to an amino acid sequence selected from the group consisting of: SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74 and SEQ ID NO. 298.

In one aspect, the invention features an anti-KRAS antibody, or an antigen-binding fragment thereof, comprising a heavy chain variable domain comprising an amino acid sequence that is at least 98% identical to an amino acid sequence selected from the group consisting of: SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73 and SEQ ID NO. 297; and comprising a light chain variable domain comprising an amino acid sequence that is at least 98% identical to an amino acid sequence selected from the group consisting of: SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74 and SEQ ID NO. 298.

In one aspect, the invention features an anti-KRAS antibody, or an antigen-binding fragment thereof, comprising a heavy chain variable domain comprising an amino acid sequence that is at least 99% identical to an amino acid sequence selected from the group consisting of: SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73 and SEQ ID NO. 297; and comprising a light chain variable domain comprising an amino acid sequence that is at least 99% identical to an amino acid sequence selected from the group consisting of: SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74 and SEQ ID NO. 298.

In one aspect, the invention features an isolated anti-KRAS antibody, or an antigen-binding fragment thereof, comprising a heavy chain variable domain and a light chain variable domain selected from the group consisting of a heavy chain variable domain comprising the amino acid sequence set forth in SEQ ID NO: 1 and a light chain variable domain comprising the amino acid sequence set forth in SEQ ID NO: 2; a heavy chain variable domain comprising the amino acid sequence set forth in SEQ ID NO: 3 and a light chain variable domain comprising the amino acid sequence set forth in SEQ ID NO: 4; a heavy chain variable domain comprising the amino acid sequence set forth in SEQ ID NO: 5 and a light chain variable domain comprising the amino acid sequence set forth in SEQ ID NO: 6; a heavy chain variable domain comprising the amino acid sequence set forth in SEQ ID NO: 7 and a light chain variable domain comprising the amino acid sequence set forth in SEQ ID NO: 8; a heavy chain variable domain comprising the amino acid sequence set forth in SEQ ID NO: 9 and a light chain variable domain comprising the amino acid sequence set forth in SEQ ID NO: 10; a heavy chain variable domain comprising the amino acid sequence set forth in SEQ ID NO: 11 and a light chain variable domain comprising the amino acid sequence set forth in SEQ ID NO: 12; a heavy chain variable domain comprising the amino acid sequence set forth in SEQ ID NO: 13 and a light chain variable domain comprising the amino acid sequence set forth in SEQ ID NO: 14; a heavy chain variable domain comprising the amino acid sequence set forth in SEQ ID NO: 15 and a light chain variable domain comprising the amino acid sequence set forth in SEQ ID NO: 16; a heavy chain variable domain comprising the amino acid sequence set forth in SEQ ID NO: 17 and a light chain variable domain comprising the amino acid sequence set forth in SEQ ID NO: 18; a heavy chain variable domain comprising the amino acid sequence set forth in SEQ ID NO: 19 and a light chain variable domain comprising the amino acid sequence set forth in SEQ ID NO: 20; a heavy chain variable domain comprising the amino acid sequence set forth in SEQ ID NO: 21 and a light chain variable domain comprising the amino acid sequence set forth in SEQ ID NO: 22; a heavy chain variable domain comprising the amino acid sequence set forth in SEQ ID NO: 23 and a light chain variable domain comprising the amino acid sequence set forth in SEQ ID NO: 24; a heavy chain variable domain comprising the amino acid sequence set forth in SEQ ID NO: 25 and a light chain variable domain comprising the amino acid sequence set forth in SEQ ID NO: 26; a heavy chain variable domain comprising the amino acid sequence set forth in SEQ ID NO: 27 and a light chain variable domain comprising the amino acid sequence set forth in SEQ ID NO: 28; a heavy chain variable domain comprising the amino acid sequence set forth in SEQ ID NO: 29 and a light chain variable domain comprising the amino acid sequence set forth in SEQ ID NO: 30; a heavy chain variable domain comprising the amino acid sequence set forth in SEQ ID NO: 31 and a light chain variable domain comprising the amino acid sequence set forth in SEQ ID NO: 32; a heavy chain variable domain comprising the amino acid sequence set forth in SEQ ID NO: 33 and a light chain variable domain comprising the amino acid sequence set forth in SEQ ID NO: 34; a heavy chain variable domain comprising the amino acid sequence set forth in SEQ ID NO: 35 and a light chain variable domain comprising the amino acid sequence set forth in SEQ ID NO: 36; a heavy chain variable domain comprising the amino acid sequence set forth in SEQ ID NO: 37 and a light chain variable domain of SEQ ID NO: 38; a heavy chain variable domain comprising the amino acid sequence set forth in SEQ ID NO: 39 and a light chain variable domain comprising the amino acid sequence set forth in SEQ ID NO: 40; a heavy chain variable domain comprising the amino acid sequence set forth in SEQ ID NO: 41 and a light chain variable domain comprising the amino acid sequence set forth in SEQ ID NO: 42; a heavy chain variable domain comprising the amino acid sequence set forth in SEQ ID NO: 43 and a light chain variable domain comprising the amino acid sequence set forth in SEQ ID NO: 44; a heavy chain variable domain comprising the amino acid sequence set forth in SEQ ID NO: 45 and a light chain variable domain comprising the amino acid sequence set forth in SEQ ID NO: 46; a heavy chain variable domain comprising the amino acid sequence set forth in SEQ ID NO: 47 and a light chain variable domain comprising the amino acid sequence set forth in SEQ ID NO: 48; a heavy chain variable domain comprising the amino acid sequence set forth in SEQ ID NO: 49 and a light chain variable domain comprising the amino acid sequence set forth in SEQ ID NO: 50; a heavy chain variable domain comprising the amino acid sequence set forth in SEQ ID NO: 51 and a light chain variable domain comprising the amino acid sequence set forth in SEQ ID NO: 52; a heavy chain variable domain comprising the amino acid sequence set forth in SEQ ID NO: 53 and a light chain variable domain comprising the amino acid sequence set forth in SEQ ID NO: 54; a heavy chain variable domain comprising the amino acid sequence set forth in SEQ ID NO: 55 and a light chain variable domain comprising the amino acid sequence set forth in SEQ ID NO: 56; a heavy chain variable domain comprising the amino acid sequence set forth in SEQ ID NO: 57 and the light chain variable domain comprising the amino acid sequence set forth in SEQ ID NO: 58; a heavy chain variable domain comprising the amino acid sequence set forth in SEQ ID NO: 59 and a light chain variable domain comprising the amino acid sequence set forth in SEQ ID NO: 60; a heavy chain variable domain comprising the amino acid sequence set forth in SEQ ID NO: 61 and a light chain variable domain comprising the amino acid sequence set forth in SEQ ID NO: 62; a heavy chain variable domain comprising the amino acid sequence set forth in SEQ ID NO: 63 and a light chain variable domain comprising the amino acid sequence set forth in SEQ ID NO: 64; a heavy chain variable domain comprising the amino acid sequence set forth in SEQ ID NO: 65 and a light chain variable domain comprising the amino acid sequence set forth in SEQ ID NO: 66; a heavy chain variable domain comprising the amino acid sequence set forth in SEQ ID NO: 67 and a light chain variable domain comprising the amino acid sequence set forth in SEQ ID NO: 68; a heavy chain variable domain comprising the amino acid sequence set forth in SEQ ID NO: 69 and a light chain variable domain comprising the amino acid sequence set forth in SEQ ID NO: 70; a heavy chain variable domain comprising the amino acid sequence set forth in SEQ ID NO: 71 and a light chain variable domain comprising the amino acid sequence set forth in SEQ ID NO: 72; a heavy chain variable domain comprising the amino acid sequence set forth in SEQ ID NO: 73 and a light chain variable domain comprising the amino acid sequence set forth in SEQ ID NO: 74; and a heavy chain variable domain comprising the amino acid sequence set forth in SEQ ID NO: 297 and a light chain variable domain comprising the amino acid sequence set forth in SEQ ID NO: 298. In one embodiment of any one of the aspects or embodiments above, the antibody has a $K_D$ of at least $1\times10^{-6}$M. In one embodiment of any one of the aspects or embodiments above, the antibody is human. In one embodiment of any one of the aspects or embodiments above, the antibody is an IgG. In another embodiment, the antibody is an IgG1, IgG2, IgG3 or an IgG4 isotype. In one embodiment, the antigen-binding fragment is a Fab fragment or an scFv.

In one aspect, the anti-KRAS antibody, or antigen-binding fragment thereof, of any one of the above aspects or embodiments, is conjugated to an intracellular delivery compound.

In one embodiment, the antibody conjugate is the structure shown in FIG. 2B.

In one embodiment, the antibody conjugate is the structure shown in FIG. 2C.

In one aspect, the invention features a pharmaceutical composition comprising the anti-KRAS antibody, or antibody fragment thereof, of any one of the above aspects or embodiments, and a pharmaceutically acceptable carrier.

In one aspect, the invention features a method for treating a subject having cancer comprising administering an effective amount of the anti-KRAS antibody, or antigen-binding fragment thereof, of any one of the above aspects or embodiments to the subject. In one embodiment, the cancer is a cancer associated with a KRAS mutation. In another embodiment, the KRAS mutation is G12D mutation. In a further embodiment, the cancer is selected from the group consisting of pancreatic cancer, lung cancer, including non-small cell lung cancer, colorectal cancer, prostate cancer, breast cancer, ovarian cancer, head and neck cancer, bladder cancer, melanoma, colorectal cancer, leiomyoma, leiomyosarcoma, glioma, glioblastoma, esophageal cancer, liver cancer, kidney cancer, stomach cancer, colon cancer, cervical cancer, uterine cancer, liver cancer and a hematological cancer.

In another embodiment, the invention features a nucleic acid encoding the antibody or antigen binding fragment of any one of the above aspects or embodiments.

In one embodiment, the invention features a vector comprising the nucleic acid of any one of the aspects or embodiments herein.

In one embodiment, the invention features a host cell comprising the vector of any one of the above aspects or embodiments.

DETAILED DESCRIPTION

Definitions

Figure 1:
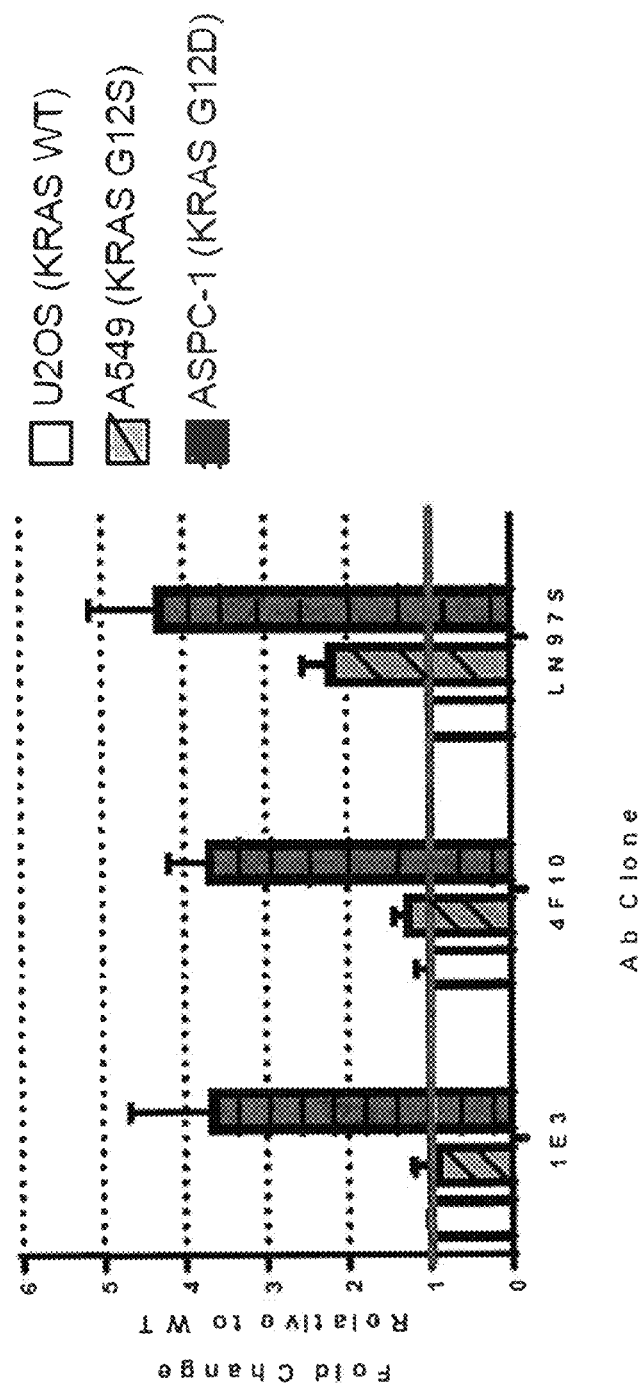
FIG. 1 is a graph that shows the binding of fully human anti-KRAS antibody clones 1E3, 4F10 and LN97S to cellular targets in KRAS G12D over-expressing pancreatic tumor cells (ASPC-1). Binding in U2OS human osteosarcoma cells (KRAS wildtype) and A549 human lung adenocarcinoma epithelial cells (KRASG12S expressing cells) were tested as controls. Binding is shown as fold change relative to wild type.

An "antigen binding protein" is a protein comprising a portion that binds to an antigen and, optionally, a scaffold or framework portion that allows the antigen binding portion to adopt a confirmation that promotes binding of the antigen binding protein to the antigen. Examples of antigen binding proteins include antibodies, antibody fragments (i.e., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al. (2003) *Proteins: Structure, Function, and Bioinformatics*, 53(1):121-129; Roque et al. (2004) *Biotechnol. Prog.* 20:639-654. In addition, peptide antibody mimetics ("PAMs") can be used, as well as scaffolds based on antibody mimetics utilizing fibronectin components as a scaffold.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least one of its CDRs.

An "epitope" is the portion of a molecule that is bound by an antigen binding protein (e.g., by an antibody). Generally the variable regions, particularly the CDRs, of an antibody interact with the epitope.

The term "antibody" refers to an immunoglobulin (Ig) molecule comprised of four polypeptide chains, two heavy (H) chains and two light (L) chains, or any functional fragment, mutant, variant, or derivation thereof, which retains the essential epitope binding features of an Ig molecule.

Generally, the amino-terminal portion of each antibody chain includes a variable region, including three hypervariable complementarity determining regions (CDRs) that are primarily responsible for antigen recognition. The carboxy-terminal portion of each chain defines a constant region, e.g., responsible for effector function. Human light chains are classified as kappa or lambda light chains Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites. A single VH or VL domain may be sufficient to confer antigen-binding specificity.

The variable regions of antibody heavy and light chains (VH and VL, respectively) exhibit the same general structure of relatively conserved framework regions (FR) joined by three CDRs. From N-terminus to C-terminus, both light and heavy chains comprise the domains FR1, CDR1, FR2, CDR2, FR3, CDR3 and FR4. The assignment of amino acids to each domain is known in the art, including, for example, definitions as described in Kabat et al. in Sequences of Proteins of Immunological Interest, 5$^{th}$ Ed., US Dept. of Health and Human Services, PHS, NIH, NIH Publication no. 91-3242, 1991 (herein referred to as "Kabat numbering"). For example, the CDR regions of an antibody can be determined according to Kabat numbering.

The terms "intact antibody" or "full length antibody" refer to an antibody composed of two identical antibody light chains and two identical antibody heavy chains that each contain an Fc region.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

The terms "anti-KRAS antibody" and "an antibody that binds to KRAS" refer to an antibody that is capable of binding KRAS with sufficient affinity such that the antibody is useful as a diagnostic and/or therapeutic agent in targeting KRAS, including human KRAS.

The term "monospecific", as used herein, refers to an antibody, or antigen binding fragment thereof, that displays an affinity for one particular epitope. In contrast, a bispecific antibody, or antigen-binding fragment thereof, displays affinity for two different epitopes. In one embodiment, the methods and compositions described herein are useful for intracellular delivery of a monospecific antibody, or antigen-binding fragment thereof. In one embodiment, the anti-KRAS antibody, or antigen-binding fragment thereof, of the invention is monospecific.

A "multi-specific antibody" is an antibody that recognizes more than one epitope on one or more antigens. A subclass of this type of antibody is a "bispecific antibody" which recognizes two distinct epitopes on the same or different antigens.

The terms "specific binding", "specifically binds" or "specifically binding", as used herein in the context of an antibody, refer to non-covalent or covalent preferential binding of an antibody to an antigen relative to other molecules or moieties (e.g., an antibody specifically binds to a particular antigen relative to other available antigens). In one embodiment, an antibody specifically binds to an antigen (e.g., KRAS) if it binds to the antigen with a dissociation constant $K_D$ of $10^{-5}$ M or less (e.g., $10^{-6}$ M or less, $10^{-7}$ M or less, $10^{-8}$ M or less, $10^{-9}$ M or less, or $10^{-10}$ M or less).

The term "human antibody", as used herein, refers to an antibody, or an antigen binding fragment of an antibody, comprising heavy and lights chains derived from human immunoglobulin sequences. Human antibodies may be identified in a variety of ways, examples of which are described below, including through the immunization with an antigen of interest of a mouse that is genetically modified to express antibodies derived from human heavy and/or light chain-encoding genes. In one embodiment, a human antibody is made using recombinant methods such that the glycosylation pattern of the antibody is different than an antibody having the same sequence if it were to exist in nature.

The term "chimeric antibody" refers to an antibody that contains one or more regions derived from a particular source or species, and one or more regions derived from a different source or species.

A "humanized antibody" is an antibody or a variant, derivative, analog, or fragment thereof, which specifically binds to an antigen of interest and which comprises a framework (FR) region having substantially the amino acid sequence of a human antibody and a complementary determining region (CDR) having substantially the amino acid sequence of a non-human antibody. Generally, a humanized antibody is less likely to induce an immune response, and/or induces a less severe immune response, as compared to the non-human species antibody, e.g., a murine or chimeric antibody, when it is administered to a human subject. In one embodiment, certain amino acids in the framework and constant domains of the heavy and/or light chains of the non-human species antibody are mutated to produce the humanized antibody. Examples of how to make humanized antibodies may be found in U.S. Pat. Nos. 6,054,297, 5,886,152 and 5,877,293.

An "antibody fragment", "antibody portion", "antigen-binding fragment of an antibody", or "antigen-binding portion of an antibody" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; Fd; and Fv fragments, as well as dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, tetrabodies, and In one embodiment, the antibody fragment is an scFv. A single-chain antibody (scFv) is an antibody in which a $V_L$ and a $V_H$ region are joined via a linker (e.g., a synthetic sequence of amino acid residues) to form a continuous protein chain (see e.g., Bird et al. (1988) *Science* 242:423-426; and Huston et al. (1988) *Proc. Natl. Acad. Sci. USA* 85:5879-5883)).

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US Patent Publication Nos. 2005/0202512; 2004/0202995; 2004/0038291; 2004/0009507; 2003/0039958, and Ward et al., Nature 341:544-546, 1989).

Diabodies are bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al. (1993) *Proc. Natl. Acad. Sci. USA* 90:6444-48, and Poljak et al. (1994) *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel (1990) Gene Expression Technology: *Methods in Enzymology* 185, Academic Press, San Diego, Calif. and Baron et al. (1995) *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al. (1981) *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al. (1998) *Cytotechnology* 28:31) or CHO strain DX-B11, which is deficient in DHFR (see Urlaub et al. (1980) *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al. (1991) *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "recombinant antibody" refers to an antibody that is expressed from a cell or cell line transfected with an expression vector (or possibly more than one expression vector) comprising the coding sequence of the antibody, or a portion thereof (e.g., a DNA sequence encoding a heavy chain or a light chain). In one embodiment, said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

The term "effective amount" as used herein, refers to that amount of an antibody, or an antigen binding portion thereof, that binds KRAS which is sufficient to effect treatment of a disease associated with KRAS signaling when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art.

The term "isolated" refers to a protein (e.g., an antibody) that is substantially free of other cellular material. In one embodiment, an isolated antibody is substantially free of other proteins from the same species. In one embodiment, an isolated antibody is expressed by a cell from a different species and is substantially free of other proteins from the different species. A protein may be rendered substantially free of naturally associated components (or components associated with the cellular expression system used to produce the antibody) by isolation, using protein purification techniques well known in the art. In one embodiment, the ant-KRAS antibodies, or antigen binding fragments, of the invention are isolated.

An "intracellular delivery compound" (also referred to herein as "conjugate" or "antibody conjugate"), as used herein, refers to a compound which is conjugated (covalently or non-covalently) to an antigen binding protein (e.g., an antibody or antibody fragment) which is capable of internalizing the antigen binding protein into a cell. Examples of intracellular delivery compounds (conjugated to an antibody) are provided in FIGS. 2A-2C.

The term "KRAS," as used herein, refers to any native KRAS from any vertebrate source, including mammals such as primates (e.g., humans) and rodents (e.g., mice and rats), unless otherwise indicated. The term encompasses "full-length," unprocessed KRAS as well as any form of KRAS that results from processing in the cell. The term also encompasses naturally occurring variants of KRAS, for example, splice variants or allelic variants. The amino acid sequence of an exemplary human KRAS isoform (variant (b)) is shown in SEQ ID NO. 305. This variant (b) is composed of five exons and lacks exon 4a which the longer transcript variant (a) includes. This predominant variant (b) has a cds that terminates in exon 4b and encodes isoform b.

```
                                                                   (SEQ ID NO: 305)
  1 mteyklvvvg aggvgksalt iqliqnhfvd eydptiedsy rkqvvidget clldildtag 61 qeeysamrdq ymrtgegflc vfainntksf edihhyreqi krvkdsedvp mvlvgnkcdl 121 psrtvdtkqa qdlarsygip fietsaktrq gvddafytlv reirkhkekm skdgkkkkkk 181 sktkcvim
```

In one embodiment, the antibody, or fragment, of the invention binds to human KRAS as set forth in SEQ ID NO: 305.

KRAS Antigen Binding Proteins

The invention provides anti-KRAS antigen binding proteins, e.g., antibodies and fragments thereof, as well as methods of using and making the same. In a preferred embodiment, the anti-KRAS antibodies, and antigen-binding fragments thereof, bind to human KRAS (hKRAS). The KRAS gene encodes a 21-kDa small protein that is activated transiently as a response to extracellular stimuli or signals such as growth factors, cytokines, and hormones via cell surface receptors.

The present invention pertains to KRAS binding proteins, particularly anti-KRAS antibodies, or antigen-binding portions thereof, that bind KRAS (e.g., human KRAS), and uses thereof. Various aspects of the invention relate to antibodies and antibody fragments, pharmaceutical compositions, nucleic acids, recombinant expression vectors, and host cells for making such antibodies and fragments. Methods of using the antibodies of the invention to detect human KRAS, to inhibit KRAS activity, either in vitro or in vivo, and to prevent or treat disorders such as cancer are also encompassed by the invention.

As described in Table 4 below, included in the invention are novel human antibody heavy and light chain variable regions and CDRs that are specific to human KRAS. In one embodiment, the invention provides an anti-KRAS antibody, or an antigen-binding fragment thereof, that comprises a heavy chain having a variable domain comprising an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71 and SEQ ID NO. 73. In one embodiment, the invention provides an anti-KRAS antibody, or an antigen-binding fragment thereof, that comprises a light chain having a variable domain comprising an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72 and SEQ ID NO. 74. In one embodiment, the invention provides an anti-KRAS antibody, or an antigen-binding fragment thereof, that comprises a light chain having a variable domain comprising an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72 and SEQ ID NO. 74; and a heavy chain having a variable domain comprising an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71 and SEQ ID NO. 73.

In one embodiment, the present disclosure provides a human antibody of an IgG class that binds to a human KRAS epitope with a binding affinity of at least $10^{-6}$M, where the antibody, or antigen-binding fragment, has a heavy chain variable domain sequence which is at least 95% identical, at least 96% identical, at least 97% identical, at least 98% identical, or at least 99% identical, or identical, to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71 and SEQ ID NO. 73, and has a light chain variable domain sequence that is at least 95% identical, at least 96% identical, at least 97% identical, at least 98% identical, or at least 99% identical, or identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72 and SEQ ID NO. 74.

In one embodiment, the invention includes an anti-KRAS antibody which is an IgG and comprises four polypeptide chains including two heavy chains each comprising a heavy chain variable domain and heavy chain constant regions $C_{H1}$, $C_{H2}$ and $C_{H3}$, and two light chains each comprising a light chain variable domain and a light chain constant region ($C_L$). In certain embodiments, the antibody is an IgG1, IgG2, IgG3 or an IgG4. The heavy and light chain variable domain sequences may be selected from those described herein in SEQ ID Nos: 1-74.

Complementarity determining regions (CDRs) are known as hypervariable regions both in the light chain and the heavy chain variable domains. The more highly conserved portions of variable domains are called the framework (FR). Complementarity determining regions (CDRs) and framework regions (FR) of a given antibody may be identified using the numbering system described by Kabat et al. (1991) NIH Publication 91-3242, National Technical Information Service, Springfield, Va. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

In certain embodiments, the present invention provides an anti-KRAS antibody comprising the CDRs of the heavy and light chain variable domains described in Table 4 (SEQ ID Nos: 1 to 74). For example, the invention provides an anti-KRAS antibody, or antigen-binding fragment thereof, comprising a heavy chain variable region having the CDRs described in an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71 and SEQ ID NO. 73. In one embodiment, the invention provides an anti-KRAS antibody, or antigen-binding fragment thereof, comprising a light chain variable region having the CDRs described in an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72 and SEQ ID NO. 74. In one embodiment, the invention provides an anti-KRAS antibody, or antigen-binding fragment thereof, comprising a light chain variable region having the CDRs described in an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72 and SEQ ID NO. 74; and a heavy chain variable region having the CDRs described in an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71 and SEQ ID NO. 73.

In one embodiment, the invention includes an isolated anti-KRAS antibody, or an antigen-binding fragment thereof, wherein the heavy chain variable domain is selected from the group consisting of a heavy chain variable domain comprising an amino acid sequence that is at least 95% identical to SEQ ID NO: 1 and comprising the heavy chain CDR set of SEQ ID Nos: 75, 76, and 77; a heavy chain variable domain comprising an amino acid sequence that is at least 95% identical to SEQ ID NO: 3 and comprising the heavy chain CDR set of SEQ ID Nos: 81, 82 and 83; a heavy chain variable domain comprising an amino acid sequence that is at least 95% identical to SEQ ID NO: 5 and comprising the heavy chain CDR set of SEQ ID Nos: 87, 88 and 89; a heavy chain variable domain comprising an amino acid sequence that is at least 95% identical to SEQ ID NO: 7 and comprising the heavy chain CDR set of SEQ ID Nos: 93, 94 and 95; a heavy chain variable domain comprising an amino acid sequence that is at least 95% identical to SEQ ID NO: 9 and comprising the heavy chain CDR set of SEQ ID Nos: 99, 100 and 101; a heavy chain variable domain comprising an amino acid sequence that is at least 95% identical to SEQ ID NO: 11 and comprising the heavy chain CDR set of SEQ ID Nos: 105, 106 and 107; a heavy chain variable domain comprising an amino acid sequence that is at least 95% identical to SEQ ID NO: 13 and comprising the heavy chain CDR set of SEQ ID Nos: 111, 112 and 113; a heavy chain variable domain comprising an amino acid sequence that is at least 95% identical to SEQ ID NO: 15 and comprising the heavy chain CDR set of SEQ ID Nos: 117, 118 and 119; a heavy chain variable domain comprising an amino acid sequence that is at least 95% identical to SEQ ID NO: 17 and comprising the heavy chain CDR set of SEQ ID Nos: 123, 124 and 125; a heavy chain variable domain comprising an amino acid sequence that is at least 95% identical to SEQ ID NO: 19 and comprising the heavy chain CDR set of SEQ ID Nos: 129, 130 and 131; a heavy chain variable domain comprising an amino acid sequence that is at least 95% identical to SEQ ID NO: 21 and comprising the heavy chain CDR set of SEQ ID Nos: 135, 136 and 137; a heavy chain variable domain comprising an amino acid sequence that is at least 95% identical to SEQ ID NO: 23 and comprising the heavy chain CDR set of SEQ ID Nos: 141, 142 and 143; a heavy chain variable domain comprising an amino acid sequence that is at least 95% identical to SEQ ID NO: 25 and comprising the heavy chain CDR set of SEQ ID Nos: 147, 148 and 149; a heavy chain variable domain comprising an amino acid sequence that is at least 95% identical to SEQ ID NO: 27 and comprising the heavy chain CDR set of SEQ ID Nos: 153, 154 and 155; a heavy chain variable domain comprising an amino acid sequence that is at least 95% identical to SEQ ID NO: 29 and comprising the heavy chain CDR set of SEQ ID Nos: 159, 160 and 161; a heavy chain variable domain comprising an amino acid sequence that is at least 95% identical to SEQ ID NO: 31 and comprising the heavy chain CDR set of SEQ ID Nos: 165, 166 and 167; a heavy chain variable domain comprising an amino acid sequence that is at least 95% identical to SEQ ID NO: 33 and comprising the heavy chain CDR set of SEQ ID Nos: 171, 172 and 173; a heavy chain variable domain comprising an amino acid sequence that is at least 95% identical to SEQ ID NO: 35 and comprising the heavy chain CDR set of SEQ ID Nos: 177, 178 and 179; a heavy chain variable domain comprising an amino acid sequence that is at least 95% identical to SEQ ID NO: 37 and comprising the heavy chain CDR set of SEQ ID Nos: 183, 184 and 185; a heavy chain variable domain comprising an amino acid sequence that is at least 95% identical to SEQ ID NO: 39 and comprising the heavy chain CDR set of SEQ ID Nos: 189, 190 and 191; a heavy chain variable domain comprising an amino acid sequence that is at least 95% identical to SEQ ID NO: 41 and comprising the heavy chain CDR set of SEQ ID Nos: 195, 196 and 197; a heavy chain variable domain comprising an amino acid sequence that is at least 95% identical to SEQ ID NO: 43 and comprising the heavy chain CDR set of SEQ ID Nos: 201, 202 and 203; a heavy chain variable domain comprising an amino acid sequence that is at least 95% identical to SEQ ID NO: 45 and comprising the heavy chain CDR set of SEQ ID Nos: 207, 208 and 209; a heavy chain variable domain comprising an amino acid sequence that is at least 95% identical to SEQ ID NO: 47 and comprising the heavy chain CDR set of SEQ ID Nos: 213, 214 and 215; a heavy chain variable domain comprising an amino acid sequence that is at least 95% identical to SEQ ID NO: 49 and comprising the heavy chain CDR set of SEQ ID Nos: 219, 220 and 221; a heavy chain variable domain comprising an amino acid sequence that is at least 95% identical to SEQ ID NO: 51 and comprising the heavy chain CDR set of SEQ ID Nos: 225, 226 and 227; a heavy chain variable domain comprising an amino acid sequence that is at least 95% identical to SEQ ID NO: 53 and comprising the heavy chain CDR set of SEQ ID Nos: 231, 232 and 233; a heavy chain variable domain comprising an amino acid sequence that is at least 95% identical to SEQ ID NO: 55 and comprising the heavy chain CDR set of SEQ ID Nos: 237, 238 and 239; a heavy chain variable domain comprising an amino acid sequence that is at least 95% identical to SEQ ID NO: 57 and comprising the heavy chain CDR set of SEQ ID Nos: 243, 244 and 245; a heavy chain variable domain comprising an amino acid sequence that is at least 95% identical to SEQ ID NO: 59 and comprising the heavy chain CDR set of SEQ ID Nos: 249, 250 and 251; a heavy chain variable domain comprising an amino acid sequence that is at least 95% identical to SEQ ID NO: 61 and comprising the heavy chain CDR set of SEQ ID Nos: 255, 256 and 257; a heavy chain variable domain comprising an amino acid sequence that is at least 95% identical to SEQ ID NO: 63 and comprising the heavy chain CDR set of SEQ ID Nos: 261, 262 and 263; a heavy chain variable domain comprising an amino acid sequence that is at least 95% identical to SEQ ID NO: 65 and comprising the heavy chain CDR set of SEQ ID Nos: 267, 268 and 269; a heavy chain variable domain comprising an amino acid sequence that is at least 95% identical to SEQ ID NO: 67 and comprising the heavy chain CDR set of SEQ ID Nos: 273, 274 and 275; a heavy chain variable domain comprising an amino acid sequence that is at least 95% identical to SEQ ID NO: 69 and comprising the heavy chain CDR set of SEQ ID Nos: 279, 280 and 281; a heavy chain variable domain comprising an amino acid sequence that is at least 95% identical to SEQ ID NO: 71 and comprising the heavy chain CDR set of SEQ ID Nos: 285, 286 and 287; and a heavy chain variable domain comprising an amino acid sequence that is at least 95% identical to SEQ ID NO: 73 and comprising the heavy chain CDR set of SEQ ID Nos: 291, 292 and 293; and comprises a light chain variable domain selected from the group consisting of a light chain variable domain comprising an amino acid sequence that is at least 95% identical to SEQ ID NO: 2 and comprising the light chain CDR set of SEQ ID Nos: 78, 79 and 80; a light chain variable domain comprising an amino acid sequence that is at least 95% identical to SEQ ID NO: 4 and comprising the light chain CDR set of SEQ ID Nos: 84, 85 and 86; a light chain variable domain comprising an amino acid sequence that is at least 95% identical to SEQ ID NO: 6 and comprising the light chain CDR set of SEQ ID Nos: 90, 91 and 92; a light chain variable domain comprising an amino acid sequence that is at least 95% identical to SEQ ID NO: 8 and comprising the light chain CDR set of SEQ ID Nos: 96, 97 and 98; a light chain variable domain comprising an amino acid sequence that is at least 95% identical to SEQ ID NO: 10 and comprising the light chain CDR set of SEQ ID Nos: 102, 103 and 104; a light chain variable domain comprising an amino acid sequence that is at least 95% identical to SEQ ID NO: 12 and comprising the light chain CDR set of SEQ ID Nos: 108, 109 and 110; a light chain variable domain comprising an amino acid sequence that is at least 95% identical to SEQ ID NO: 14 and comprising the light chain CDR set of SEQ ID Nos: 114, 115 and 116; a light chain variable domain comprising an amino acid sequence that is at least 95% identical to SEQ ID NO: 16 and comprising the light chain CDR set of SEQ ID Nos: 120, 121 and 122; a light chain variable domain comprising an amino acid sequence that is at least 95% identical to SEQ ID NO: 18 and comprising the light chain CDR set of SEQ ID Nos: 126, 127 and 128; a light chain variable domain comprising an amino acid sequence that is at least 95% identical to SEQ ID NO: 20 and comprising the light chain CDR set of SEQ ID Nos: 132, 133 and 134; a light chain variable domain comprising an amino acid sequence that is at least 95% identical to SEQ ID NO: 22 and comprising the light chain CDR set of SEQ ID Nos: 138, 139 and 140; a light chain variable domain comprising an amino acid sequence that is at least 95% identical to SEQ ID NO: 24 and comprising the light chain CDR set of SEQ ID Nos: 144, 145 and 146; a light chain variable domain comprising an amino acid sequence that is at least 95% identical to SEQ ID NO: 26 and comprising the light chain CDR set of SEQ ID Nos: 150, 151 and 152; a light chain variable domain comprising an amino acid sequence that is at least 95% identical to SEQ ID NO: 28 and comprising the light chain CDR set of SEQ ID Nos: 156, 157 and 158; a light chain variable domain comprising an amino acid sequence that is at least 95% identical to SEQ ID NO: 30 and comprising the light chain CDR set of SEQ ID Nos: 163, 163 and 164; a light chain variable domain comprising an amino acid sequence that is at least 95% identical to SEQ ID NO: 32 and comprising the light chain CDR set of SEQ ID Nos: 168, 169 and 170; a light chain variable domain comprising an amino acid sequence that is at least 95% identical to SEQ ID NO: 34 and comprising the light chain CDR set of SEQ ID Nos: 174, 175 and 176; a light chain variable domain comprising an amino acid sequence that is at least 95% identical to SEQ ID NO: 36 and comprising the light chain CDR set of SEQ ID Nos: 180, 181 and 182; a light chain variable domain comprising an amino acid sequence that is at least 95% identical to SEQ ID NO: 38 and comprising the light chain CDR set of SEQ ID Nos: 186, 187 and 188; a light chain variable domain comprising an amino acid sequence that is at least 95% identical to SEQ ID NO: 40 and comprising the light chain CDR set of SEQ ID Nos: 192, 193 and 194; a light chain variable domain comprising an amino acid sequence that is at least 95% identical to SEQ ID NO: 42 and comprising the light chain CDR set of SEQ ID Nos: 198, 199 and 200; a light chain variable domain comprising an amino acid sequence that is at least 95% identical to SEQ ID NO: 44 and comprising the light chain CDR set of SEQ ID Nos: 204, 205 and 206; a light chain variable domain comprising an amino acid sequence that is at least 95% identical to SEQ ID NO: 46 and comprising the light chain CDR set of SEQ ID Nos: 210, 211 and 212; a light chain variable domain comprising an amino acid sequence that is at least 95% identical to SEQ ID NO: 48 and comprising the light chain CDR set of SEQ ID Nos: 216, 217 and 218; a light chain variable domain comprising an amino acid sequence that is at least 95% identical to SEQ ID NO: 50 and comprising the light chain CDR set of SEQ ID Nos: 222, 223 and 224; a light chain variable domain comprising an amino acid sequence that is at least 95% identical to SEQ ID NO: 52 and comprising the light chain CDR set of SEQ ID Nos: 228, 229 and 227; a light chain variable domain comprising an amino acid sequence that is at least 95% identical to SEQ ID NO: 54 and comprising the light chain CDR set of SEQ ID Nos: 234, 235 and 236; a light chain variable domain comprising an amino acid sequence that is at least 95% identical to SEQ ID NO: 56 and comprising the light chain CDR set of SEQ ID Nos: 240, 241 and 242; a light chain variable domain comprising an amino acid sequence that is at least 95% identical to SEQ ID NO: 58 and comprising the light chain CDR set of SEQ ID Nos: 246, 247 and 248; a light chain variable domain comprising an amino acid sequence that is at least 95% identical to SEQ ID NO: 60 and comprising the light chain CDR set of SEQ ID Nos: 252, 253 and 254; a light chain variable domain comprising an amino acid sequence that is at least 95% identical to SEQ ID NO: 62 and comprising the light chain CDR set of SEQ ID Nos: 258, 259 and 260; a light chain variable domain comprising an amino acid sequence that is at least 95% identical to SEQ ID NO: 64 and comprising the light chain CDR set of SEQ ID Nos: 264, 265 and 266; a light chain variable domain comprising an amino acid sequence that is at least 95% identical to SEQ ID NO: 66 and comprising the light chain CDR set of SEQ ID Nos: 270, 271 and 272; a light chain variable domain comprising an amino acid sequence that is at least 95% identical to SEQ ID NO: 68 and comprising the light chain CDR set of SEQ ID Nos: 276, 277 and 278; a light chain variable domain comprising an amino acid sequence that is at least 95% identical to SEQ ID NO: 70 and comprising the light chain CDR set of SEQ ID Nos: 282, 283 and 284; a light chain variable domain comprising an amino acid sequence that is at least 95% identical to SEQ ID NO: 72 and comprising the light chain CDR set of SEQ ID Nos: 288, 289 and 290; a light chain variable domain comprising an amino acid sequence that is at least 95% identical to SEQ ID NO: 74 and comprising the light chain CDR set of SEQ ID Nos: 294, 295 and 296.

In one embodiment, the present disclosure provides a fully human antibody of an IgG class that binds to a KRAS epitope with a binding affinity of $10^{-6}$M or less, that has a heavy chain variable domain sequence that is at least 95% identical, at least 96% identical, at least 97% identical, at least 98% identical, at least 99% identical, or 100% identical to an amino acid sequence selected from SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71 and SEQ ID NO. 73; and that has a light chain variable domain sequence that is at least 95% identical, at least 96% identical, at least 97% identical, at least 98% identical, at least 99% identical, or 100% identical to an amino acid sequence selected from SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72 and SEQ ID NO. 74.

In one embodiment, the invention provides an anti-KRAS antibody, or an antigen-binding fragment thereof, comprising a heavy chain comprising a CDR3 domain as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71 and SEQ ID NO. 73, and comprising a variable domain comprising an amino acid sequence that has at least 95%, at least 96%, at least 97%, at least 98%, or at least 99% identical to a sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71 and SEQ ID NO. 73. In one embodiment, the invention provides an anti-KRAS antibody, or an antigen-binding fragment thereof, comprising a light chain comprising a CDR3 domain as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72 and SEQ ID NO. 74, and having a light chain variable domain comprising an amino acid sequence that has at least 95%, at least 96%, at least 97%, at least 98%, or at least 99% identical to a sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72 and SEQ ID NO. 74. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to KRAS and retains the functional characteristics, e.g., binding affinity, of the parent.

In one embodiment, the present invention features an isolated human anti-human KRAS (hKRAS) antibody, or an antigen-binding fragment thereof, comprising a heavy chain variable domain comprising a heavy chain CDR set (CDR1, CDR2, and CDR3) selected from the group consisting of SEQ ID Nos. 75, 76 and 77; SEQ ID Nos. 81, 82 and 83; SEQ ID Nos. 87, 88 and 89; SEQ ID Nos. 93, 94 and 95; SEQ ID Nos. 99, 100 and 101; SEQ ID Nos. 105, 106 and 107; SEQ ID Nos. 111, 112 and 113; SEQ ID Nos. 117, 118 and 119; SEQ ID Nos. 123, 124 and 125; SEQ ID Nos. 129, 130 and 131; SEQ ID Nos. 135, 136 and 137; SEQ ID Nos. 141, 142 and 143; SEQ ID Nos. 147, 148 and 149; SEQ ID Nos. 153, 154 and 155; SEQ ID Nos. 159, 160, 161; SEQ ID Nos. 165, 166 and 167; SEQ ID Nos. 171, 172 and 173; SEQ ID Nos. 177, 178 and 179; SEQ ID Nos. 183, 184 and 185; SEQ ID Nos. 189, 190 and 191; SEQ ID Nos. 195, 196 and 197; SEQ ID Nos. 201, 202 and 203; SEQ ID Nos. 207, 208 and 209; SEQ ID Nos. 213, 214 and 215; SEQ ID Nos. 219, 220 and 221; SEQ ID Nos. 225, 226 and 227; SEQ ID Nos. 231, 232 and 233; SEQ ID Nos. 237, 238 and 239; SEQ ID Nos. 243, 244 and 245; SEQ ID Nos. 249, 250 and 251; SEQ ID Nos. 255, 256 and 257; SEQ ID Nos. 261, 262 and 263; SEQ ID Nos. 267, 268 and 269; SEQ ID Nos. 273, 274 and 275; SEQ ID Nos. 279, 280 and 281; SEQ ID Nos. 285, 286 and 287; and SEQ ID Nos. 291, 292 and 293; and a light chain variable domain comprising a light chain CDR set (CDR1, CDR2, and CDR3) selected from the group consisting of SEQ ID Nos. 78, 79 and 80; SEQ ID Nos. 84, 85 and 86; SEQ ID Nos. 90, 91 and 92; SEQ ID Nos. 96, 97 and 98; SEQ ID Nos. 102, 103 and 104; SEQ ID Nos. 108, 109 and 110; SEQ ID Nos. 114, 115 and 116; SEQ ID Nos. 120, 121 and 122; SEQ ID Nos. 126, 127 and 128; SEQ ID Nos. 132, 133 and 134; SEQ ID Nos. 138, 139 and 140; SEQ ID Nos. 144, 145 and 146; SEQ ID Nos. 150, 151 and 152; SEQ ID Nos. 156, 157 and 158; SEQ ID Nos. 162, 163 and 164; SEQ ID Nos. 168, 169 and 170; SEQ ID Nos. 174, 175 and 176; SEQ ID Nos. 180, 181 and 182; SEQ ID Nos. 186, 187 and 188; SEQ ID Nos. 192, 193 and 194; SEQ ID Nos. 198, 199 and 200; SEQ ID Nos. 204, 205 and 206; SEQ ID Nos. 210, 211 and 212; SEQ ID Nos. 216, 217 and 218; SEQ ID Nos. 222, 223 and 224; SEQ ID Nos. 228, 229 and 230; SEQ ID Nos. 234, 235 and 236; SEQ ID Nos. 240, 241 and 242; SEQ ID Nos. 246, 247 and 248; SEQ ID Nos. 252, 253 and 254; SEQ ID Nos. 258, 259 and 260; SEQ ID Nos. 264, 265 and 266; SEQ ID Nos. 270, 271 and 272; 276, 277 and 278; SEQ ID Nos. 282, 283 and 284; SEQ ID Nos. 288, 289 and 290; and SEQ ID Nos. 294, 295 and 296.

In one embodiment, the antibody of the invention comprises a heavy chain CDR set/light chain CDR set selected from the group consisting of the heavy chain variable domain CDR set of SEQ ID Nos: 75, 76 and 77 and the light chain variable domain CDR set of 78, 79 and 80; the heavy chain variable domain CDR set of SEQ ID Nos: 81, 82 and 83 and the light chain variable domain CDR set of 84, 85 and 86; the heavy chain variable domain CDR set of SEQ ID Nos: 87, 88 and 89 and the light chain variable domain CDR set of 90, 91 and 92; the heavy chain variable domain CDR set of SEQ ID Nos: 93, 94 and 95 and the light chain variable domain CDR set of 96, 97 and 98; the heavy chain variable domain CDR set of SEQ ID Nos: 99, 100 and 101 and the light chain variable domain CDR set of 102, 103 and 104; the heavy chain variable domain CDR set of SEQ ID Nos: 105, 106 and 107 and the light chain variable domain CDR set of 108, 109 and 110; the heavy chain variable domain CDR set of SEQ ID Nos: 111, 112 and 113 and the light chain variable domain CDR set of 114, 115 and 116; the heavy chain variable domain CDR set of SEQ ID Nos: 117, 118 and 119 and the light chain variable domain CDR set of 120, 121 and 122; the heavy chain variable domain CDR set of SEQ ID Nos: 123, 124 and 125 and the light chain variable domain CDR set of 126, 127 and 128; the heavy chain variable domain CDR set of SEQ ID Nos: 129, 130 and 131 and the light chain variable domain CDR set of 132, 133 and 134; the heavy chain variable domain CDR set of SEQ ID Nos: 135, 136 and 137 and the light chain variable domain CDR set of 138, 139 and 140; the heavy chain variable domain CDR set of SEQ ID Nos: 141, 142 and 143 and the light chain variable domain CDR set of 144, 145 and 146; the heavy chain variable domain CDR set of SEQ ID Nos: 147, 148 and 149 and the light chain variable domain CDR set of 150, 151 and 152; the heavy chain variable domain CDR set of SEQ ID Nos: 153, 154 and 155 and the light chain variable domain CDR set of 156, 157 and 158; the heavy chain variable domain CDR set of SEQ ID Nos: 159, 160 and 161 and the light chain variable domain CDR set of 162, 163 and 164; the heavy chain variable domain CDR set of SEQ ID Nos: 165, 166 and 167 and the light chain variable domain CDR set of 168, 169 and 170; the heavy chain variable domain CDR set of SEQ ID Nos: 171, 172 and 173 and the light chain variable domain CDR set of 174, 175 and 176; the heavy chain variable domain CDR set of SEQ ID Nos: 177, 178 and 179 and the light chain variable domain CDR set of 180, 181 and 182; the heavy chain variable domain CDR set of SEQ ID Nos: 183, 184 and 185 and the light chain variable domain CDR set of 186, 187 and 188; the heavy chain variable domain CDR set of SEQ ID Nos: 189, 190 and 191 and the light chain variable domain CDR set of 192, 193 and 194; the heavy chain variable domain CDR set of SEQ ID Nos: 195, 196 and 197 and the light chain variable domain CDR set of 198, 199 and 200; the heavy chain variable domain CDR set of SEQ ID Nos: 201, 202 and 203 and the light chain variable domain CDR set of 204, 205 and 206; the heavy chain variable domain CDR set of SEQ ID Nos: 207, 208 and 209 and the light chain variable domain CDR set of 210, 211 and 212; the heavy chain variable domain CDR set of SEQ ID Nos: 213, 1214 and 215 and the light chain variable domain CDR set of 216, 217 and 218; the heavy chain variable domain CDR set of SEQ ID Nos: 219, 220 and 221 and the light chain variable domain CDR set of 222, 223 and 224; the heavy chain variable domain CDR set of SEQ ID Nos: 225, 226 and 227 and the light chain variable domain CDR set of 228, 229 and 230; the heavy chain variable domain CDR set of SEQ ID Nos: 231, 232 and 233 and the light chain variable domain CDR set of 234, 235 and 236; the heavy chain variable domain CDR set of SEQ ID Nos: 237, 238 and 239 and the light chain variable domain CDR set of 240, 241 and 242; the heavy chain variable domain CDR set of SEQ ID Nos: 243, 244 and 245 and the light chain variable domain CDR set of 246, 247 and 248; the heavy chain variable domain CDR set of SEQ ID Nos: 249, 250 and 251 and the light chain variable domain CDR set of 252, 253 and 254; the heavy chain variable domain CDR set of SEQ ID Nos: 255, 256 and 257 and the light chain variable domain CDR set of 258, 259 and 260; the heavy chain variable domain CDR set of SEQ ID Nos: 261, 262 and 263 and the light chain variable domain CDR set of 1264, 265 and 266; the heavy chain variable domain CDR set of SEQ ID Nos: 267, 268 and 269 and the light chain variable domain CDR set of 270, 271 and 272; the heavy chain variable domain CDR set of SEQ ID Nos: 273, 274 and 275 and the light chain variable domain CDR set of 276, 277 and 278; the heavy chain variable domain CDR set of SEQ ID Nos: 279, 280 and 281 and the light chain variable domain CDR set of 282, 283 and 284; the heavy chain variable domain CDR set of SEQ ID Nos: 285, 286 and 287 and the light chain variable domain CDR set of 288, 289 and 290; and the heavy chain variable domain CDR set of SEQ ID Nos: 291, 292 and 293 and the light chain variable domain CDR set of 294, 295 and 296.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

In one embodiment, the present invention is directed to an antibody, or an antigen binding fragment thereof, having the antigen binding regions of any of the antibodies described in Table 4. The antibodies of the invention, including those described in Table 4, bind to human KRAS. In one aspect, the present invention is directed to an isolated anti-KRAS antibody, or an antigen-binding fragment thereof, comprising a heavy chain variable domain and a light chain variable domain selected from the group consisting of the heavy chain variable domain of SEQ ID NO: 1 and the light chain variable domain of SEQ ID NO: 2; the heavy chain variable domain of SEQ ID NO: 3 and the light chain variable domain of SEQ ID NO: 4; the heavy chain variable domain of SEQ ID NO: 5 and the light chain variable domain of SEQ ID NO: 6; the heavy chain variable domain of SEQ ID NO: 7 and the light chain variable domain of SEQ ID NO: 8; the heavy chain variable domain of SEQ ID NO: 9 and the light chain variable domain of SEQ ID NO: 10; the heavy chain variable domain of SEQ ID NO: 11 and the light chain variable domain of SEQ ID NO: 12; the heavy chain variable domain of SEQ ID NO: 13 and the light chain variable domain of SEQ ID NO: 14; the heavy chain variable domain of SEQ ID NO: 15 and the light chain variable domain of SEQ ID NO: 16; the heavy chain variable domain of SEQ ID NO: 17 and the light chain variable domain of SEQ ID NO: 18; the heavy chain variable domain of SEQ ID NO: 19 and the light chain variable domain of SEQ ID NO: 20; the heavy chain variable domain of SEQ ID NO: 21 and the light chain variable domain of SEQ ID NO: 22; the heavy chain variable domain of SEQ ID NO: 23 and the light chain variable domain of SEQ ID NO: 24; the heavy chain variable domain of SEQ ID NO: 25 and the light chain variable domain of SEQ ID NO: 26; the heavy chain variable domain of SEQ ID NO: 27 and the light chain variable domain of SEQ ID NO: 28; the heavy chain variable domain of SEQ ID NO: 29 and the light chain variable domain of SEQ ID NO: 30; the heavy chain variable domain of SEQ ID NO: 31 and the light chain variable domain of SEQ ID NO: 32; the heavy chain variable domain of SEQ ID NO: 33 and the light chain variable domain of SEQ ID NO: 34; the heavy chain variable domain of SEQ ID NO: 35 and the light chain variable domain of SEQ ID NO: 36; the heavy chain variable domain of SEQ ID NO: 37 and the light chain variable domain of SEQ ID NO: 38; the heavy chain variable domain of SEQ ID NO: 39 and the light chain variable domain of SEQ ID NO: 40; the heavy chain variable domain of SEQ ID NO: 41 and the light chain variable domain of SEQ ID NO: 42; the heavy chain variable domain of SEQ ID NO: 43 and the light chain variable domain of SEQ ID NO: 44; the heavy chain variable domain of SEQ ID NO: 45 and the light chain variable domain of SEQ ID NO: 46; the heavy chain variable domain of SEQ ID NO: 47 and the light chain variable domain of SEQ ID NO: 48; the heavy chain variable domain of SEQ ID NO: 49 and the light chain variable domain of SEQ ID NO: 50; the heavy chain variable domain of SEQ ID NO: 51 and the light chain variable domain of SEQ ID NO: 52; the heavy chain variable domain of SEQ ID NO: 53 and the light chain variable domain of SEQ ID NO: 54; the heavy chain variable domain of SEQ ID NO: 55 and the light chain variable domain of SEQ ID NO: 56; the heavy chain variable domain of SEQ ID NO: 57 and the light chain variable domain of SEQ ID NO: 58; the heavy chain variable domain of SEQ ID NO: 59 and the light chain variable domain of SEQ ID NO: 60; the heavy chain variable domain of SEQ ID NO: 61 and the light chain variable domain of SEQ ID NO: 62; the heavy chain variable domain of SEQ ID NO: 63 and the light chain variable domain of SEQ ID NO: 64; the heavy chain variable domain of SEQ ID NO: 65 and the light chain variable domain of SEQ ID NO: 66; the heavy chain variable domain of SEQ ID NO: 67 and the light chain variable domain of SEQ ID NO: 68; the heavy chain variable domain of SEQ ID NO: 69 and the light chain variable domain of SEQ ID NO: 70; the heavy chain variable domain of SEQ ID NO: 71 and the light chain variable domain of SEQ ID NO: 72; and the heavy chain variable domain of SEQ ID NO: 73 and the light chain variable domain of SEQ ID NO: 74.

In one embodiment, the present invention is directed to an antibody, or an antigen binding fragment thereof, having antigen binding regions of antibody K3-1F4. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 2. In one embodiment, the invention is directed to an antibody having a heavy chain variable domain comprising the CDRs of SEQ ID NO: 1, and a light chain variable domain comprising the CDRs of SEQ ID NO: 2. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 2. In one embodiment, the invention features an anti-KRAS antibody, or an antigen-binding portion thereof, comprising a heavy chain variable region comprising a CDR3 domain comprising the amino acid as set forth in SEQ ID NO: 77, a CDR2 domain comprising the amino acid sequence as set forth in SEQ ID NO: 76, and a CDR1 domain comprising the amino acid sequence as set forth in SEQ ID NO: 75; and comprising a light chain variable region comprising a CDR3 domain comprising the amino acid as set forth in SEQ ID NO: 80, a CDR2 domain comprising the amino acid sequence as set forth in SEQ ID NO: 79 and a CDR1 domain comprising the amino acid sequence as set forth in SEQ ID NO: 78. The antibody may be an IgG1 or an IgG4 isotype.

In one embodiment, the present invention is directed to an antibody, or an antigen binding fragment thereof, having antigen binding regions of antibody K3-1A7. In one embodiment, the invention provides an antibody, or antigen-binding fragment thereof, comprising a heavy chain variable domain sequence as set forth in SEQ ID NO: 3, and a light chain variable domain sequence as set forth in SEQ ID NO: 4. In one embodiment, the invention is directed to an antibody having a heavy chain variable domain comprising the CDRs of SEQ ID NO: 3, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 3, and comprises a light chain variable region having an amino acid sequence that is at least 95% identical, at least 96% identical, at least 97% identical, at least 98% identical, or at least 99% identical to the sequence set forth in SEQ ID NO: 4. In one embodiment, the invention features an anti-KRAS antibody, or an antigen-binding portion thereof, comprising a heavy chain variable region comprising a CDR3 domain comprising the amino acid as set forth in SEQ ID NO: 83, a CDR2 domain comprising the amino acid sequence as set forth in SEQ ID NO: 82, and a CDR1 domain comprising the amino acid sequence as set forth in SEQ ID NO: 81; and comprising a light chain variable region comprising a CDR3 domain comprising the amino acid as set forth in SEQ ID NO: 86, a CDR2 domain comprising the amino acid sequence as set forth in SEQ ID NO: 85 and a CDR1 domain comprising the amino acid sequence as set forth in SEQ ID NO: 84. The antibody may be an IgG1 or an IgG4 isotype.

In one embodiment, the present invention is directed to an antibody, or an antigen binding fragment thereof, having antigen binding regions of antibody K3-2B2. In one embodiment, the invention provides an antibody, or antigen-binding fragment thereof, comprising a heavy chain variable domain sequence as set forth in SEQ ID NO: 5, and a light chain variable domain sequence as set forth in SEQ ID NO: 6. In one embodiment, the invention is directed to an antibody having a heavy chain variable domain comprising the CDRs of SEQ ID NO: 5, and a light chain variable domain comprising the CDRs of SEQ ID NO: 6. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 5, and comprises a light chain variable region having an amino acid sequence that is at least 95% identical, at least 96% identical, at least 97% identical, at least 98% identical, or at least 99% identical to the sequence set forth in SEQ ID NO: 6. In one embodiment, the invention features an anti-KRAS antibody, or an antigen-binding portion thereof, comprising a heavy chain variable region comprising a CDR3 domain comprising the amino acid as set forth in SEQ ID NO: 89, a CDR2 domain comprising the amino acid sequence as set forth in SEQ ID NO: 88, and a CDR1 domain comprising the amino acid sequence as set forth in SEQ ID NO: 87; and comprising a light chain variable region comprising a CDR3 domain comprising the amino acid as set forth in SEQ ID NO: 92, a CDR2 domain comprising the amino acid sequence as set forth in SEQ ID NO: 91 and a CDR1 domain comprising the amino acid sequence as set forth in SEQ ID NO: 90. The antibody may be an IgG1 or an IgG4 isotype.

In one embodiment, the present invention is directed to an antibody, or an antigen binding fragment thereof, having antigen binding regions of antibody K3-2C2. In one embodiment, the invention provides an antibody, or antigen-binding fragment thereof, comprising a heavy chain variable domain sequence as set forth in SEQ ID NO: 7, and a light chain variable domain sequence as set forth in SEQ ID NO: 8. In one embodiment, the invention is directed to an antibody having a heavy chain variable domain comprising the CDRs of SEQ ID NO: 7, and a light chain variable domain comprising the CDRs of SEQ ID NO: 8. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 7, and comprises a light chain variable region having an amino acid sequence that is at least 95% identical, at least 96% identical, at least 97% identical, at least 98% identical, or at least 99% identical to the sequence set forth in SEQ ID NO: 8 In one embodiment, the invention features an anti-KRAS antibody, or an antigen-binding portion thereof, comprising a heavy chain variable region comprising a CDR3 domain comprising the amino acid as set forth in SEQ ID NO: 95, a CDR2 domain comprising the amino acid sequence as set forth in SEQ ID NO: 94, and a CDR1 domain comprising the amino acid sequence as set forth in SEQ ID NO: 93; and comprising a light chain variable region comprising a CDR3 domain comprising the amino acid as set forth in SEQ ID NO: 98, a CDR2 domain comprising the amino acid sequence as set forth in SEQ ID NO: 97 and a CDR1 domain comprising the amino acid sequence as set forth in SEQ ID NO: 96. The antibody may be an IgG1 or an IgG4 isotype.

In one embodiment, the present invention is directed to an antibody, or an antigen binding fragment thereof, having antigen binding regions of antibody K3-2H8. In one embodiment, the invention provides an antibody, or antigen-binding fragment thereof, comprising a heavy chain variable domain sequence as set forth in SEQ ID NO: 9, and a light chain variable domain sequence as set forth in SEQ ID NO: 10. In one embodiment, the invention is directed to an antibody having a heavy chain variable domain comprising the CDRs of SEQ ID NO: 9, and a light chain variable domain comprising the CDRs of SEQ ID NO: 10. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 9, and comprises a light chain variable region having an amino acid sequence that is at least 95% identical, at least 96% identical, at least 97% identical, at least 98% identical, or at least 99% identical to the sequence set forth in SEQ ID NO: 10. In one embodiment, the invention features an anti-KRAS antibody, or an antigen-binding portion thereof, comprising a heavy chain variable region comprising a CDR3 domain comprising the amino acid as set forth in SEQ ID NO: 101, a CDR2 domain comprising the amino acid sequence as set forth in SEQ ID NO: 100, and a CDR1 domain comprising the amino acid sequence as set forth in SEQ ID NO: 99; and comprising a light chain variable region comprising a CDR3 domain comprising the amino acid as set forth in SEQ ID NO: 104, a CDR2 domain comprising the amino acid sequence as set forth in SEQ ID NO: 103 and a CDR1 domain comprising the amino acid sequence as set forth in SEQ ID NO: 102. The antibody may be an IgG1 or an IgG4 isotype.

In one embodiment, the present invention is directed to an antibody, or an antigen binding fragment thereof, having antigen binding regions of antibody K3-3E8. In one embodiment, the invention provides an antibody, or antigen-binding fragment thereof, comprising a heavy chain variable domain sequence as set forth in SEQ ID NO: 11, and a light chain variable domain sequence as set forth in SEQ ID NO: 12. In one embodiment, the invention is directed to an antibody having a heavy chain variable domain comprising the CDRs of SEQ ID NO: 11, and a light chain variable domain comprising the CDRs of SEQ ID NO: 12. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 11, and comprises a light chain variable region having an amino acid sequence that is at least 95% identical, at least 96% identical, at least 97% identical, at least 98% identical, or at least 99% identical to the sequence set forth in SEQ ID NO: 12. In one embodiment, the invention features an anti-KRAS antibody, or an antigen-binding portion thereof, comprising a heavy chain variable region comprising a CDR3 domain comprising the amino acid as set forth in SEQ ID NO: 107, a CDR2 domain comprising the amino acid sequence as set forth in SEQ ID NO: 106, and a CDR1 domain comprising the amino acid sequence as set forth in SEQ ID NO: 105; and comprising a light chain variable region comprising a CDR3 domain comprising the amino acid as set forth in SEQ ID NO: 110, a CDR2 domain comprising the amino acid sequence as set forth in SEQ ID NO: 109 and a CDR1 domain comprising the amino acid sequence as set forth in SEQ ID NO: 108. The antibody may be an IgG1 or an IgG4 isotype.

In one embodiment, the present invention is directed to an antibody, or an antigen binding fragment thereof, having antigen binding regions of antibody K3-4D9. In one embodiment, the invention provides an antibody, or antigen-binding fragment thereof, comprising a heavy chain variable domain sequence as set forth in SEQ ID NO: 13, and a light chain variable domain sequence as set forth in SEQ ID NO: 14. In one embodiment, the invention is directed to an antibody having a heavy chain variable domain comprising the CDRs of SEQ ID NO: 13, and a light chain variable domain comprising the CDRs of SEQ ID NO: 14. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 13, and comprises a light chain variable region having an amino acid sequence that is at least 95% identical, at least 96% identical, at least 97% identical, at least 98% identical, or at least 99% identical to the sequence set forth in SEQ ID NO: 14. In one embodiment, the invention features an anti-KRAS antibody, or an antigen-binding portion thereof, comprising a heavy chain variable region comprising a CDR3 domain comprising the amino acid as set forth in SEQ ID NO: 1133, a CDR2 domain comprising the amino acid sequence as set forth in SEQ ID NO: 112, and a CDR1 domain comprising the amino acid sequence as set forth in SEQ ID NO: 111; and comprising a light chain variable region comprising a CDR3 domain comprising the amino acid as set forth in SEQ ID NO: 116, a CDR2 domain comprising the amino acid sequence as set forth in SEQ ID NO: 115 and a CDR1 domain comprising the amino acid sequence as set forth in SEQ ID NO: 114. The antibody may be an IgG1 or an IgG4 isotype.

In one embodiment, the present invention is directed to an antibody, or an antigen binding fragment thereof, having antigen binding regions of antibody K3-4F10. In one embodiment, the invention provides an antibody, or antigen-binding fragment thereof, comprising a heavy chain variable domain sequence as set forth in SEQ ID NO: 15, and a light chain variable domain sequence as set forth in SEQ ID NO: 16. In one embodiment, the invention is directed to an antibody having a heavy chain variable domain comprising the CDRs of SEQ ID NO: 15, and a light chain variable domain comprising the CDRs of SEQ ID NO: 16. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 15, and comprises a light chain variable region having an amino acid sequence that is at least 95% identical, at least 96% identical, at least 97% identical, at least 98% identical, or at least 99% identical to the sequence set forth in SEQ ID NO: 16. In one embodiment, the invention features an anti-KRAS antibody, or an antigen-binding portion thereof, comprising a heavy chain variable region comprising a CDR3 domain comprising the amino acid as set forth in SEQ ID NO: 119, a CDR2 domain comprising the amino acid sequence as set forth in SEQ ID NO: 118, and a CDR1 domain comprising the amino acid sequence as set forth in SEQ ID NO: 117; and comprising a light chain variable region comprising a CDR3 domain comprising the amino acid as set forth in SEQ ID NO: 122, a CDR2 domain comprising the amino acid sequence as set forth in SEQ ID NO: 121 and a CDR1 domain comprising the amino acid sequence as set forth in SEQ ID NO: 120. The antibody may be an IgG1 or an IgG4 isotype.

In one embodiment, the present invention is directed to an antibody, or an antigen binding fragment thereof, having antigen binding regions of antibody K3-5H6. In one embodiment, the invention provides an antibody, or antigen-binding fragment thereof, comprising a heavy chain variable domain sequence as set forth in SEQ ID NO: 17, and a light chain variable domain sequence as set forth in SEQ ID NO: 18. In one embodiment, the invention is directed to an antibody having a heavy chain variable domain comprising the CDRs of SEQ ID NO: 17, and a light chain variable domain comprising the CDRs of SEQ ID NO: 18. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 17, and comprises a light chain variable region having an amino acid sequence that is at least 95% identical, at least 96% identical, at least 97% identical, at least 98% identical, or at least 99% identical to the sequence set forth in SEQ ID NO: 18. In one embodiment, the invention features an anti-KRAS antibody, or an antigen-binding portion thereof, comprising a heavy chain variable region comprising a CDR3 domain comprising the amino acid as set forth in SEQ ID NO: 125, a CDR2 domain comprising the amino acid sequence as set forth in SEQ ID NO: 124, and a CDR1 domain comprising the amino acid sequence as set forth in SEQ ID NO: 123; and comprising a light chain variable region comprising a CDR3 domain comprising the amino acid as set forth in SEQ ID NO: 128, a CDR2 domain comprising the amino acid sequence as set forth in SEQ ID NO: 127 and a CDR1 domain comprising the amino acid sequence as set forth in SEQ ID NO: 126. The antibody may be an IgG1 or an IgG4 isotype.

In one embodiment, the present invention is directed to an antibody, or an antigen binding fragment thereof, having antigen binding regions of antibody K3-1F12. In one embodiment, the invention provides an antibody, or antigen-binding fragment thereof, comprising a heavy chain variable domain sequence as set forth in SEQ ID NO: 19, and a light chain variable domain sequence as set forth in SEQ ID NO: 20. In one embodiment, the invention is directed to an antibody having a heavy chain variable domain comprising the CDRs of SEQ ID NO: 19, and a light chain variable domain comprising the CDRs of SEQ ID NO: 20. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 19, and comprises a light chain variable region having an amino acid sequence that is at least 95% identical, at least 96% identical, at least 97% identical, at least 98% identical, or at least 99% identical to the sequence set forth in SEQ ID NO: 20. In one embodiment, the invention features an anti-KRAS antibody, or an antigen-binding portion thereof, comprising a heavy chain variable region comprising a CDR3 domain comprising the amino acid as set forth in SEQ ID NO: 131, a CDR2 domain comprising the amino acid sequence as set forth in SEQ ID NO: 130, and a CDR1 domain comprising the amino acid sequence as set forth in SEQ ID NO: 129; and comprising a light chain variable region comprising a CDR3 domain comprising the amino acid as set forth in SEQ ID NO: 134, a CDR2 domain comprising the amino acid sequence as set forth in SEQ ID NO: 133 and a CDR1 domain comprising the amino acid sequence as set forth in SEQ ID NO: 132. The antibody may be an IgG1 or an IgG4 isotype.

In one embodiment, the present invention is directed to an antibody, or an antigen binding fragment thereof, having antigen binding regions of antibody K3-1H12. In one embodiment, the invention provides an antibody, or antigen-binding fragment thereof, comprising a heavy chain variable domain sequence as set forth in SEQ ID NO: 21, and a light chain variable domain sequence as set forth in SEQ ID NO: 22. In one embodiment, the invention is directed to an antibody having a heavy chain variable domain comprising the CDRs of SEQ ID NO: 21, and a light chain variable domain comprising the CDRs of SEQ ID NO: 22. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 21, and comprises a light chain variable region having an amino acid sequence that is at least 95% identical, at least 96% identical, at least 97% identical, at least 98% identical, or at least 99% identical to the sequence set forth in SEQ ID NO: 22. In one embodiment, the invention features an anti-KRAS antibody, or an antigen-binding portion thereof, comprising a heavy chain variable region comprising a CDR3 domain comprising the amino acid as set forth in SEQ ID NO: 137, a CDR2 domain comprising the amino acid sequence as set forth in SEQ ID NO: 136, and a CDR1 domain comprising the amino acid sequence as set forth in SEQ ID NO: 135; and comprising a light chain variable region comprising a CDR3 domain comprising the amino acid as set forth in SEQ ID NO: 140, a CDR2 domain comprising the amino acid sequence as set forth in SEQ ID NO: 139 and a CDR1 domain comprising the amino acid sequence as set forth in SEQ ID NO: 138. The antibody may be an IgG1 or an IgG4 isotype.

In one embodiment, the present invention is directed to an antibody, or an antigen binding fragment thereof, having antigen binding regions of antibody K3-1C3. In one embodiment, the invention provides an antibody, or antigen-binding fragment thereof, comprising a heavy chain variable domain sequence as set forth in SEQ ID NO: 23, and a light chain variable domain sequence as set forth in SEQ ID NO: 24. In one embodiment, the invention is directed to an antibody having a heavy chain variable domain comprising the CDRs of SEQ ID NO: 23, and a light chain variable domain comprising the CDRs of SEQ ID NO: 24. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 23, and comprises a light chain variable region having an amino acid sequence that is at least 95% identical, at least 96% identical, at least 97% identical, at least 98% identical, or at least 99% identical to the sequence set forth in SEQ ID NO: 24. In one embodiment, the invention features an anti-KRAS antibody, or an antigen-binding portion thereof, comprising a heavy chain variable region comprising a CDR3 domain comprising the amino acid as set forth in SEQ ID NO: 143, a CDR2 domain comprising the amino acid sequence as set forth in SEQ ID NO: 142, and a CDR1 domain comprising the amino acid sequence as set forth in SEQ ID NO: 141; and comprising a light chain variable region comprising a CDR3 domain comprising the amino acid as set forth in SEQ ID NO: 146, a CDR2 domain comprising the amino acid sequence as set forth in SEQ ID NO: 145 and a CDR1 domain comprising the amino acid sequence as set forth in SEQ ID NO: 144. The antibody may be an IgG1 or an IgG4 isotype.

In one embodiment, the present invention is directed to an antibody, or an antigen binding fragment thereof, having antigen binding regions of antibody K3-1D3. In one embodiment, the invention provides an antibody, or antigen-binding fragment thereof, comprising a heavy chain variable domain sequence as set forth in SEQ ID NO: 25, and a light chain variable domain sequence as set forth in SEQ ID NO: 26. In one embodiment, the invention is directed to an antibody having a heavy chain variable domain comprising the CDRs of SEQ ID NO: 25, and a light chain variable domain comprising the CDRs of SEQ ID NO: 26. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 25, and comprises a light chain variable region having an amino acid sequence that is at least 95% identical, at least 96% identical, at least 97% identical, at least 98% identical, or at least 99% identical to the sequence set forth in SEQ ID NO: 26. In one embodiment, the invention features an anti-KRAS antibody, or an antigen-binding portion thereof, comprising a heavy chain variable region comprising a CDR3 domain comprising the amino acid as set forth in SEQ ID NO: 149, a CDR2 domain comprising the amino acid sequence as set forth in SEQ ID NO: 148, and a CDR1 domain comprising the amino acid sequence as set forth in SEQ ID NO: 147; and comprising a light chain variable region comprising a CDR3 domain comprising the amino acid as set forth in SEQ ID NO: 152, a CDR2 domain comprising the amino acid sequence as set forth in SEQ ID NO: 151 and a CDR1 domain comprising the amino acid sequence as set forth in SEQ ID NO: 150. The antibody may be an IgG1 or an IgG4 isotype.

In one embodiment, the present invention is directed to an antibody, or an antigen binding fragment thereof, having antigen binding regions of antibody K3-1E6. In one embodiment, the invention provides an antibody, or antigen-binding fragment thereof, comprising a heavy chain variable domain sequence as set forth in SEQ ID NO: 27, and a light chain variable domain sequence as set forth in SEQ ID NO: 28. In one embodiment, the invention is directed to an antibody having a heavy chain variable domain comprising the CDRs of SEQ ID NO: 27, and a light chain variable domain comprising the CDRs of SEQ ID NO: 28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 27, and comprises a light chain variable region having an amino acid sequence that is at least 95% identical, at least 96% identical, at least 97% identical, at least 98% identical, or at least 99% identical to the sequence set forth in SEQ ID NO: 28. In one embodiment, the invention features an anti-KRAS antibody, or an antigen-binding portion thereof, comprising a heavy chain variable region comprising a CDR3 domain comprising the amino acid as set forth in SEQ ID NO: 155, a CDR2 domain comprising the amino acid sequence as set forth in SEQ ID NO: 154, and a CDR1 domain comprising the amino acid sequence as set forth in SEQ ID NO: 153; and comprising a light chain variable region comprising a CDR3 domain comprising the amino acid as set forth in SEQ ID NO: 158, a CDR2 domain comprising the amino acid sequence as set forth in SEQ ID NO: 157 and a CDR1 domain comprising the amino acid sequence as set forth in SEQ ID NO: 156. The antibody may be an IgG1 or an IgG4 isotype.

In one embodiment, the present invention is directed to an antibody, or an antigen binding fragment thereof, having antigen binding regions of antibody K3-1F6. In one embodiment, the invention provides an antibody, or antigen-binding fragment thereof, comprising a heavy chain variable domain sequence as set forth in SEQ ID NO: 29, and a light chain variable domain sequence as set forth in SEQ ID NO: 30. In one embodiment, the invention is directed to an antibody having a heavy chain variable domain comprising the CDRs of SEQ ID NO: 29, and a light chain variable domain comprising the CDRs of SEQ ID NO: 30. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 29, and comprises a light chain variable region having an amino acid sequence that is at least 95% identical, at least 96% identical, at least 97% identical, at least 98% identical, or at least 99% identical to the sequence set forth in SEQ ID NO: 30. In one embodiment, the invention features an anti-KRAS antibody, or an antigen-binding portion thereof, comprising a heavy chain variable region comprising a CDR3 domain comprising the amino acid as set forth in SEQ ID NO: 161, a CDR2 domain comprising the amino acid sequence as set forth in SEQ ID NO: 160, and a CDR1 domain comprising the amino acid sequence as set forth in SEQ ID NO: 159; and comprising a light chain variable region comprising a CDR3 domain comprising the amino acid as set forth in SEQ ID NO: 164, a CDR2 domain comprising the amino acid sequence as set forth in SEQ ID NO: 163 and a CDR1 domain comprising the amino acid sequence as set forth in SEQ ID NO: 162. The antibody may be an IgG1 or an IgG4 isotype.

In one embodiment, the present invention is directed to an antibody, or an antigen binding fragment thereof, having antigen binding regions of antibody K3-1G6. In one embodiment, the invention provides an antibody, or antigen-binding fragment thereof, comprising a heavy chain variable domain sequence as set forth in SEQ ID NO: 31, and a light chain variable domain sequence as set forth in SEQ ID NO: 32. In one embodiment, the invention is directed to an antibody having a heavy chain variable domain comprising the CDRs of SEQ ID NO: 31, and a light chain variable domain comprising the CDRs of SEQ ID NO: 32. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 31, and comprises a light chain variable region having an amino acid sequence that is at least 95% identical, at least 96% identical, at least 97% identical, at least 98% identical, or at least 99% identical to the sequence set forth in SEQ ID NO: 32. In one embodiment, the invention features an anti-KRAS antibody, or an antigen-binding portion thereof, comprising a heavy chain variable region comprising a CDR3 domain comprising the amino acid as set forth in SEQ ID NO: 167, a CDR2 domain comprising the amino acid sequence as set forth in SEQ ID NO: 166, and a CDR1 domain comprising the amino acid sequence as set forth in SEQ ID NO: 165; and comprising a light chain variable region comprising a CDR3 domain comprising the amino acid as set forth in SEQ ID NO: 170, a CDR2 domain comprising the amino acid sequence as set forth in SEQ ID NO: 169 and a CDR1 domain comprising the amino acid sequence as set forth in SEQ ID NO: 168. The antibody may be an IgG1 or an IgG4 isotype.

In one embodiment, the present invention is directed to an antibody, or an antigen binding fragment thereof, having antigen binding regions of antibody K3-1E3. In one embodiment, the invention provides an antibody, or antigen-binding fragment thereof, comprising a heavy chain variable domain sequence as set forth in SEQ ID NO: 33, and a light chain variable domain sequence as set forth in SEQ ID NO: 34. In one embodiment, the invention is directed to an antibody having a heavy chain variable domain comprising the CDRs of SEQ ID NO: 33, and a light chain variable domain comprising the CDRs of SEQ ID NO: 34. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 33, and comprises a light chain variable region having an amino acid sequence that is at least 95% identical, at least 96% identical, at least 97% identical, at least 98% identical, or at least 99% identical to the sequence set forth in SEQ ID NO: 34. In one embodiment, the invention features an anti-KRAS antibody, or an antigen-binding portion thereof, comprising a heavy chain variable region comprising a CDR3 domain comprising the amino acid as set forth in SEQ ID NO: 173, a CDR2 domain comprising the amino acid sequence as set forth in SEQ ID NO: 172, and a CDR1 domain comprising the amino acid sequence as set forth in SEQ ID NO: 171; and comprising a light chain variable region comprising a CDR3 domain comprising the amino acid as set forth in SEQ ID NO: 176, a CDR2 domain comprising the amino acid sequence as set forth in SEQ ID NO: 175 and a CDR1 domain comprising the amino acid sequence as set forth in SEQ ID NO: 174. The antibody may be an IgG1 or an IgG4 isotype.

In one embodiment, the present invention is directed to an antibody, or an antigen binding fragment thereof, having antigen binding regions of antibody K3-3D11. In one embodiment, the invention provides an antibody, or antigen-binding fragment thereof, comprising a heavy chain variable domain sequence as set forth in SEQ ID NO: 35, and a light chain variable domain sequence as set forth in SEQ ID NO: 36. In one embodiment, the invention is directed to an antibody having a heavy chain variable domain comprising the CDRs of SEQ ID NO: 36, and a light chain variable domain comprising the CDRs of SEQ ID NO: 36. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 35, and comprises a light chain variable region having an amino acid sequence that is at least 95% identical, at least 96% identical, at least 97% identical, at least 98% identical, or at least 99% identical to the sequence set forth in SEQ ID NO: 36. In one embodiment, the invention features an anti-KRAS antibody, or an antigen-binding portion thereof, comprising a heavy chain variable region comprising a CDR3 domain comprising the amino acid as set forth in SEQ ID NO: 179, a CDR2 domain comprising the amino acid sequence as set forth in SEQ ID NO: 178, and a CDR1 domain comprising the amino acid sequence as set forth in SEQ ID NO: 177; and comprising a light chain variable region comprising a CDR3 domain comprising the amino acid as set forth in SEQ ID NO: 182, a CDR2 domain comprising the amino acid sequence as set forth in SEQ ID NO: 181 and a CDR1 domain comprising the amino acid sequence as set forth in SEQ ID NO: 180. The antibody may be an IgG1 or an IgG4 isotype.

In one embodiment, the present invention is directed to an antibody, or an antigen binding fragment thereof, having antigen binding regions of antibody K3-4E10. In one embodiment, the invention provides an antibody, or antigen-binding fragment thereof, comprising a heavy chain variable domain sequence as set forth in SEQ ID NO: 37, and a light chain variable domain sequence as set forth in SEQ ID NO: 38. In one embodiment, the invention is directed to an antibody having a heavy chain variable domain comprising the CDRs of SEQ ID NO: 37, and a light chain variable domain comprising the CDRs of SEQ ID NO: 38. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 37, and comprises a light chain variable region having an amino acid sequence that is at least 95% identical, at least 96% identical, at least 97% identical, at least 98% identical, or at least 99% identical to the sequence set forth in SEQ ID NO: 38. In one embodiment, the invention features an anti-KRAS antibody, or an antigen-binding portion thereof, comprising a heavy chain variable region comprising a CDR3 domain comprising the amino acid as set forth in SEQ ID NO: 185, a CDR2 domain comprising the amino acid sequence as set forth in SEQ ID NO: 184, and a CDR1 domain comprising the amino acid sequence as set forth in SEQ ID NO: 183; and comprising a light chain variable region comprising a CDR3 domain comprising the amino acid as set forth in SEQ ID NO: 188, a CDR2 domain comprising the amino acid sequence as set forth in SEQ ID NO: 187 and a CDR1 domain comprising the amino acid sequence as set forth in SEQ ID NO: 186. The antibody may be an IgG1 or an IgG4 isotype.

In one embodiment, the present invention is directed to an antibody, or an antigen binding fragment thereof, having antigen binding regions of antibody K3-4F10. In one embodiment, the invention provides an antibody, or antigen-binding fragment thereof, comprising a heavy chain variable domain sequence as set forth in SEQ ID NO: 39, and a light chain variable domain sequence as set forth in SEQ ID NO: 40. In one embodiment, the invention is directed to an antibody having a heavy chain variable domain comprising the CDRs of SEQ ID NO: 39, and a light chain variable domain comprising the CDRs of SEQ ID NO: 40. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 39, and comprises a light chain variable region having an amino acid sequence that is at least 95% identical, at least 96% identical, at least 97% identical, at least 98% identical, or at least 99% identical to the sequence set forth in SEQ ID NO: 40. In one embodiment, the invention features an anti-KRAS antibody, or an antigen-binding portion thereof, comprising a heavy chain variable region comprising a CDR3 domain comprising the amino acid as set forth in SEQ ID NO: 191, a CDR2 domain comprising the amino acid sequence as set forth in SEQ ID NO: 190, and a CDR1 domain comprising the amino acid sequence as set forth in SEQ ID NO: 189; and comprising a light chain variable region comprising a CDR3 domain comprising the amino acid as set forth in SEQ ID NO: 194, a CDR2 domain comprising the amino acid sequence as set forth in SEQ ID NO: 193 and a CDR1 domain comprising the amino acid sequence as set forth in SEQ ID NO: 192. The antibody may be an IgG1 or an IgG4 isotype.

In one embodiment, the present invention is directed to an antibody, or an antigen binding fragment thereof, having antigen binding regions of antibody K3-4A12. In one embodiment, the invention provides an antibody, or antigen-binding fragment thereof, comprising a heavy chain variable domain sequence as set forth in SEQ ID NO: 41, and a light chain variable domain sequence as set forth in SEQ ID NO: 42. In one embodiment, the invention is directed to an antibody having a heavy chain variable domain comprising the CDRs of SEQ ID NO: 41, and a light chain variable domain comprising the CDRs of SEQ ID NO: 42. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 41, and comprises a light chain variable region having an amino acid sequence that is at least 95% identical, at least 96% identical, at least 97% identical, at least 98% identical, or at least 99% identical to the sequence set forth in SEQ ID NO: 42. In one embodiment, the invention features an anti-KRAS antibody, or an antigen-binding portion thereof, comprising a heavy chain variable region comprising a CDR3 domain comprising the amino acid as set forth in SEQ ID NO: 197, a CDR2 domain comprising the amino acid sequence as set forth in SEQ ID NO: 196, and a CDR1 domain comprising the amino acid sequence as set forth in SEQ ID NO: 195; and comprising a light chain variable region comprising a CDR3 domain comprising the amino acid as set forth in SEQ ID NO: 200, a CDR2 domain comprising the amino acid sequence as set forth in SEQ ID NO: 199 and a CDR1 domain comprising the amino acid sequence as set forth in SEQ ID NO: 198. The antibody may be an IgG1 or an IgG4 isotype.

In one embodiment, the present invention is directed to an antibody, or an antigen binding fragment thereof, having antigen binding regions of antibody K3-4D12. In one embodiment, the invention provides an antibody, or antigen-binding fragment thereof, comprising a heavy chain variable domain sequence as set forth in SEQ ID NO: 43, and a light chain variable domain sequence as set forth in SEQ ID NO: 44. In one embodiment, the invention is directed to an antibody having a heavy chain variable domain comprising the CDRs of SEQ ID NO: 43, and a light chain variable domain comprising the CDRs of SEQ ID NO: 44. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 43, and comprises a light chain variable region having an amino acid sequence that is at least 95% identical, at least 96% identical, at least 97% identical, at least 98% identical, or at least 99% identical to the sequence set forth in SEQ ID NO: 44. In one embodiment, the invention features an anti-KRAS antibody, or an antigen-binding portion thereof, comprising a heavy chain variable region comprising a CDR3 domain comprising the amino acid as set forth in SEQ ID NO: 203, a CDR2 domain comprising the amino acid sequence as set forth in SEQ ID NO: 202, and a CDR1 domain comprising the amino acid sequence as set forth in SEQ ID NO: 201; and comprising a light chain variable region comprising a CDR3 domain comprising the amino acid as set forth in SEQ ID NO: 206, a CDR2 domain comprising the amino acid sequence as set forth in SEQ ID NO: 205 and a CDR1 domain comprising the amino acid sequence as set forth in SEQ ID NO: 204. The antibody may be an IgG1 or an IgG4 isotype.

In one embodiment, the present invention is directed to an antibody, or an antigen binding fragment thereof, having antigen binding regions of antibody K3-4E12. In one embodiment, the invention provides an antibody, or antigen-binding fragment thereof, comprising a heavy chain variable domain sequence as set forth in SEQ ID NO: 45, and a light chain variable domain sequence as set forth in SEQ ID NO: 46. In one embodiment, the invention is directed to an antibody having a heavy chain variable domain comprising the CDRs of SEQ ID NO: 45, and a light chain variable domain comprising the CDRs of SEQ ID NO: 46. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 45, and comprises a light chain variable region having an amino acid sequence that is at least 95% identical, at least 96% identical, at least 97% identical, at least 98% identical, or at least 99% identical to the sequence set forth in SEQ ID NO: 46. In one embodiment, the invention features an anti-KRAS antibody, or an antigen-binding portion thereof, comprising a heavy chain variable region comprising a CDR3 domain comprising the amino acid as set forth in SEQ ID NO: 209, a CDR2 domain comprising the amino acid sequence as set forth in SEQ ID NO: 208, and a CDR1 domain comprising the amino acid sequence as set forth in SEQ ID NO: 207; and comprising a light chain variable region comprising a CDR3 domain comprising the amino acid as set forth in SEQ ID NO: 212, a CDR2 domain comprising the amino acid sequence as set forth in SEQ ID NO: 211 and a CDR1 domain comprising the amino acid sequence as set forth in SEQ ID NO: 210. The antibody may be an IgG1 or an IgG4 isotype.

In one embodiment, the present invention is directed to an antibody, or an antigen binding fragment thereof, having antigen binding regions of antibody K3-5C4. In one embodiment, the invention provides an antibody, or antigen-binding fragment thereof, comprising a heavy chain variable domain sequence as set forth in SEQ ID NO: 47, and a light chain variable domain sequence as set forth in SEQ ID NO: 48. In one embodiment, the invention is directed to an antibody having a heavy chain variable domain comprising the CDRs of SEQ ID NO: 47, and a light chain variable domain comprising the CDRs of SEQ ID NO: 48. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 47, and comprises a light chain variable region having an amino acid sequence that is at least 95% identical, at least 96% identical, at least 97% identical, at least 98% identical, or at least 99% identical to the sequence set forth in SEQ ID NO: 48. In one embodiment, the invention features an anti-KRAS antibody, or an antigen-binding portion thereof, comprising a heavy chain variable region comprising a CDR3 domain comprising the amino acid as set forth in SEQ ID NO: 215, a CDR2 domain comprising the amino acid sequence as set forth in SEQ ID NO: 214, and a CDR1 domain comprising the amino acid sequence as set forth in SEQ ID NO: 213; and comprising a light chain variable region comprising a CDR3 domain comprising the amino acid as set forth in SEQ ID NO: 218, a CDR2 domain comprising the amino acid sequence as set forth in SEQ ID NO: 217 and a CDR1 domain comprising the amino acid sequence as set forth in SEQ ID NO: 216. The antibody may be an IgG1 or an IgG4 isotype.

In one embodiment, the present invention is directed to an antibody, or an antigen binding fragment thereof, having antigen binding regions of antibody K3-5A4. In one embodiment, the invention provides an antibody, or antigen-binding fragment thereof, comprising a heavy chain variable domain sequence as set forth in SEQ ID NO: 49, and a light chain variable domain sequence as set forth in SEQ ID NO: 50. In one embodiment, the invention is directed to an antibody having a heavy chain variable domain comprising the CDRs of SEQ ID NO: 49, and a light chain variable domain comprising the CDRs of SEQ ID NO: 50. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 49, and comprises a light chain variable region having an amino acid sequence that is at least 95% identical, at least 96% identical, at least 97% identical, at least 98% identical, or at least 99% identical to the sequence set forth in SEQ ID NO: 50. In one embodiment, the invention features an anti-KRAS antibody, or an antigen-binding portion thereof, comprising a heavy chain variable region comprising a CDR3 domain comprising the amino acid as set forth in SEQ ID NO: 221, a CDR2 domain comprising the amino acid sequence as set forth in SEQ ID NO: 220, and a CDR1 domain comprising the amino acid sequence as set forth in SEQ ID NO: 219; and comprising a light chain variable region comprising a CDR3 domain comprising the amino acid as set forth in SEQ ID NO: 224, a CDR2 domain comprising the amino acid sequence as set forth in SEQ ID NO: 223 and a CDR1 domain comprising the amino acid sequence as set forth in SEQ ID NO: 222. The antibody may be an IgG1 or an IgG4 isotype.

In one embodiment, the present invention is directed to an antibody, or an antigen binding fragment thereof, having antigen binding regions of antibody K3-5B7. In one embodiment, the invention provides an antibody, or antigen-binding fragment thereof, comprising a heavy chain variable domain sequence as set forth in SEQ ID NO: 51, and a light chain variable domain sequence as set forth in SEQ ID NO: 52. In one embodiment, the invention is directed to an antibody having a heavy chain variable domain comprising the CDRs of SEQ ID NO: 51, and a light chain variable domain comprising the CDRs of SEQ ID NO: 52. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 51, and comprises a light chain variable region having an amino acid sequence that is at least 95% identical, at least 96% identical, at least 97% identical, at least 98% identical, or at least 99% identical to the sequence set forth in SEQ ID NO: 52. In one embodiment, the invention features an anti-KRAS antibody, or an antigen-binding portion thereof, comprising a heavy chain variable region comprising a CDR3 domain comprising the amino acid as set forth in SEQ ID NO: 227, a CDR2 domain comprising the amino acid sequence as set forth in SEQ ID NO: 226, and a CDR1 domain comprising the amino acid sequence as set forth in SEQ ID NO: 225; and comprising a light chain variable region comprising a CDR3 domain comprising the amino acid as set forth in SEQ ID NO: 230, a CDR2 domain comprising the amino acid sequence as set forth in SEQ ID NO: 229 and a CDR1 domain comprising the amino acid sequence as set forth in SEQ ID NO: 228. The antibody may be an IgG1 or an IgG4 isotype.

In one embodiment, the present invention is directed to an antibody, or an antigen binding fragment thereof, having antigen binding regions of antibody K3-5F8. In one embodiment, the invention provides an antibody, or antigen-binding fragment thereof, comprising a heavy chain variable domain sequence as set forth in SEQ ID NO: 53, and a light chain variable domain sequence as set forth in SEQ ID NO: 54. In one embodiment, the invention is directed to an antibody having a heavy chain variable domain comprising the CDRs of SEQ ID NO: 53, and a light chain variable domain comprising the CDRs of SEQ ID NO: 54. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 53, and comprises a light chain variable region having an amino acid sequence that is at least 95% identical, at least 96% identical, at least 97% identical, at least 98% identical, or at least 99% identical to the sequence set forth in SEQ ID NO: 54. In one embodiment, the invention features an anti-KRAS antibody, or an antigen-binding portion thereof, comprising a heavy chain variable region comprising a CDR3 domain comprising the amino acid as set forth in SEQ ID NO: 233, a CDR2 domain comprising the amino acid sequence as set forth in SEQ ID NO: 232, and a CDR1 domain comprising the amino acid sequence as set forth in SEQ ID NO: 231; and comprising a light chain variable region comprising a CDR3 domain comprising the amino acid as set forth in SEQ ID NO: 236, a CDR2 domain comprising the amino acid sequence as set forth in SEQ ID NO: 235 and a CDR1 domain comprising the amino acid sequence as set forth in SEQ ID NO: 234. The antibody may be an IgG1 or an IgG4 isotype.

In one embodiment, the present invention is directed to an antibody, or an antigen binding fragment thereof, having antigen binding regions of antibody K3-5D3. In one embodiment, the invention provides an antibody, or antigen-binding fragment thereof, comprising a heavy chain variable domain sequence as set forth in SEQ ID NO: 55, and a light chain variable domain sequence as set forth in SEQ ID NO: 56. In one embodiment, the invention is directed to an antibody having a heavy chain variable domain comprising the CDRs of SEQ ID NO: 55, and a light chain variable domain comprising the CDRs of SEQ ID NO: 56. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 55, and comprises a light chain variable region having an amino acid sequence that is at least 95% identical, at least 96% identical, at least 97% identical, at least 98% identical, or at least 99% identical to the sequence set forth in SEQ ID NO: 56. In one embodiment, the invention features an anti-KRAS antibody, or an antigen-binding portion thereof, comprising a heavy chain variable region comprising a CDR3 domain comprising the amino acid as set forth in SEQ ID NO: 239, a CDR2 domain comprising the amino acid sequence as set forth in SEQ ID NO: 238, and a CDR1 domain comprising the amino acid sequence as set forth in SEQ ID NO: 237; and comprising a light chain variable region comprising a CDR3 domain comprising the amino acid as set forth in SEQ ID NO: 242, a CDR2 domain comprising the amino acid sequence as set forth in SEQ ID NO: 241 and a CDR1 domain comprising the amino acid sequence as set forth in SEQ ID NO: 240. The antibody may be an IgG1 or an IgG4 isotype.

In one embodiment, the present invention is directed to an antibody, or an antigen binding fragment thereof, having antigen binding regions of antibody K3-5G5. In one embodiment, the invention provides an antibody, or antigen-binding fragment thereof, comprising a heavy chain variable domain sequence as set forth in SEQ ID NO: 57, and a light chain variable domain sequence as set forth in SEQ ID NO: 58. In one embodiment, the invention is directed to an antibody having a heavy chain variable domain comprising the CDRs of SEQ ID NO: 57, and a light chain variable domain comprising the CDRs of SEQ ID NO: 58. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 57, and comprises a light chain variable region having an amino acid sequence that is at least 95% identical, at least 96% identical, at least 97% identical, at least 98% identical, or at least 99% identical to the sequence set forth in SEQ ID NO: 58. In one embodiment, the invention features an anti-KRAS antibody, or an antigen-binding portion thereof, comprising a heavy chain variable region comprising a CDR3 domain comprising the amino acid as set forth in SEQ ID NO: 245, a CDR2 domain comprising the amino acid sequence as set forth in SEQ ID NO: 244, and a CDR1 domain comprising the amino acid sequence as set forth in SEQ ID NO: 243; and comprising a light chain variable region comprising a CDR3 domain comprising the amino acid as set forth in SEQ ID NO: 248, a CDR2 domain comprising the amino acid sequence as set forth in SEQ ID NO: 247 and a CDR1 domain comprising the amino acid sequence as set forth in SEQ ID NO: 246. The antibody may be an IgG1 or an IgG4 isotype.

In one embodiment, the present invention is directed to an antibody, or an antigen binding fragment thereof, having antigen binding regions of antibody K3-5A10. In one embodiment, the invention provides an antibody, or antigen-binding fragment thereof, comprising a heavy chain variable domain sequence as set forth in SEQ ID NO: 59, and a light chain variable domain sequence as set forth in SEQ ID NO: 60. In one embodiment, the invention is directed to an antibody having a heavy chain variable domain comprising the CDRs of SEQ ID NO: 59, and a light chain variable domain comprising the CDRs of SEQ ID NO: 60. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 59, and comprises a light chain variable region having an amino acid sequence that is at least 95% identical, at least 96% identical, at least 97% identical, at least 98% identical, or at least 99% identical to the sequence set forth in SEQ ID NO: 60. In one embodiment, the invention features an anti-KRAS antibody, or an antigen-binding portion thereof, comprising a heavy chain variable region comprising a CDR3 domain comprising the amino acid as set forth in SEQ ID NO: 251, a CDR2 domain comprising the amino acid sequence as set forth in SEQ ID NO: 250, and a CDR1 domain comprising the amino acid sequence as set forth in SEQ ID NO: 249; and comprising a light chain variable region comprising a CDR3 domain comprising the amino acid as set forth in SEQ ID NO: 254, a CDR2 domain comprising the amino acid sequence as set forth in SEQ ID NO: 253 and a CDR1 domain comprising the amino acid sequence as set forth in SEQ ID NO: 252. The antibody may be an IgG1 or an IgG4 isotype.

In one embodiment, the present invention is directed to an antibody, or an antigen binding fragment thereof, having antigen binding regions of antibody K3-5B12. In one embodiment, the invention provides an antibody, or antigen-binding fragment thereof, comprising a heavy chain variable domain sequence as set forth in SEQ ID NO: 61, and a light chain variable domain sequence as set forth in SEQ ID NO: 62. In one embodiment, the invention is directed to an antibody having a heavy chain variable domain comprising the CDRs of SEQ ID NO: 61, and a light chain variable domain comprising the CDRs of SEQ ID NO: 62. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 61, and comprises a light chain variable region having an amino acid sequence that is at least 95% identical, at least 96% identical, at least 97% identical, at least 98% identical, or at least 99% identical to the sequence set forth in SEQ ID NO: 62. In one embodiment, the invention features an anti-KRAS antibody, or an antigen-binding portion thereof, comprising a heavy chain variable region comprising a CDR3 domain comprising the amino acid as set forth in SEQ ID NO: 257, a CDR2 domain comprising the amino acid sequence as set forth in SEQ ID NO: 256, and a CDR1 domain comprising the amino acid sequence as set forth in SEQ ID NO: 255; and comprising a light chain variable region comprising a CDR3 domain comprising the amino acid as set forth in SEQ ID NO: 260, a CDR2 domain comprising the amino acid sequence as set forth in SEQ ID NO: 259 and a CDR1 domain comprising the amino acid sequence as set forth in SEQ ID NO: 258. The antibody may be an IgG1 or an IgG4 isotype.

In one embodiment, the present invention is directed to an antibody, or an antigen binding fragment thereof, having antigen binding regions of antibody K3-5C5. In one embodiment, the invention provides an antibody, or antigen-binding fragment thereof, comprising a heavy chain variable domain sequence as set forth in SEQ ID NO: 63, and a light chain variable domain sequence as set forth in SEQ ID NO: 64. In one embodiment, the invention is directed to an antibody having a heavy chain variable domain comprising the CDRs of SEQ ID NO: 63, and a light chain variable domain comprising the CDRs of SEQ ID NO: 64. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 63, and comprises a light chain variable region having an amino acid sequence that is at least 95% identical, at least 96% identical, at least 97% identical, at least 98% identical, or at least 99% identical to the sequence set forth in SEQ ID NO: 64. In one embodiment, the invention features an anti-KRAS antibody, or an antigen-binding portion thereof, comprising a heavy chain variable region comprising a CDR3 domain comprising the amino acid as set forth in SEQ ID NO: 263, a CDR2 domain comprising the amino acid sequence as set forth in SEQ ID NO: 262, and a CDR1 domain comprising the amino acid sequence as set forth in SEQ ID NO: 261; and comprising a light chain variable region comprising a CDR3 domain comprising the amino acid as set forth in SEQ ID NO: 266, a CDR2 domain comprising the amino acid sequence as set forth in SEQ ID NO: 265 and a CDR1 domain comprising the amino acid sequence as set forth in SEQ ID NO: 264. The antibody may be an IgG1 or an IgG4 isotype.

In one embodiment, the present invention is directed to an antibody, or an antigen binding fragment thereof, having antigen binding regions of antibody K3-5F6. In one embodiment, the invention provides an antibody, or antigen-binding fragment thereof, comprising a heavy chain variable domain sequence as set forth in SEQ ID NO: 65, and a light chain variable domain sequence as set forth in SEQ ID NO: 66. In one embodiment, the invention is directed to an antibody having a heavy chain variable domain comprising the CDRs of SEQ ID NO: 65, and a light chain variable domain comprising the CDRs of SEQ ID NO: 66. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 65, and comprises a light chain variable region having an amino acid sequence that is at least 95% identical, at least 96% identical, at least 97% identical, at least 98% identical, or at least 99% identical to the sequence set forth in SEQ ID NO: 66. In one embodiment, the invention features an anti-KRAS antibody, or an antigen-binding portion thereof, comprising a heavy chain variable region comprising a CDR3 domain comprising the amino acid as set forth in SEQ ID NO: 269, a CDR2 domain comprising the amino acid sequence as set forth in SEQ ID NO: 268, and a CDR1 domain comprising the amino acid sequence as set forth in SEQ ID NO: 267; and comprising a light chain variable region comprising a CDR3 domain comprising the amino acid as set forth in SEQ ID NO: 272, a CDR2 domain comprising the amino acid sequence as set forth in SEQ ID NO: 271 and a CDR1 domain comprising the amino acid sequence as set forth in SEQ ID NO: 270. The antibody may be an IgG1 or an IgG4 isotype.

In one embodiment, the present invention is directed to an antibody, or an antigen binding fragment thereof, having antigen binding regions of antibody K3-5H4. In one embodiment, the invention provides an antibody, or antigen-binding fragment thereof, comprising a heavy chain variable domain sequence as set forth in SEQ ID NO: 67, and a light chain variable domain sequence as set forth in SEQ ID NO: 68. In one embodiment, the invention is directed to an antibody having a heavy chain variable domain comprising the CDRs of SEQ ID NO: 67, and a light chain variable domain comprising the CDRs of SEQ ID NO: 68. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 67, and comprises a light chain variable region having an amino acid sequence that is at least 95% identical, at least 96% identical, at least 97% identical, at least 98% identical, or at least 99% identical to the sequence set forth in SEQ ID NO: 68. In one embodiment, the invention features an anti-KRAS antibody, or an antigen-binding portion thereof, comprising a heavy chain variable region comprising a CDR3 domain comprising the amino acid as set forth in SEQ ID NO: 275, a CDR2 domain comprising the amino acid sequence as set forth in SEQ ID NO: 274, and a CDR1 domain comprising the amino acid sequence as set forth in SEQ ID NO: 273; and comprising a light chain variable region comprising a CDR3 domain comprising the amino acid as set forth in SEQ ID NO: 278, a CDR2 domain comprising the amino acid sequence as set forth in SEQ ID NO: 277 and a CDR1 domain comprising the amino acid sequence as set forth in SEQ ID NO: 277. The antibody may be an IgG1 or an IgG4 isotype.

In one embodiment, the present invention is directed to an antibody, or an antigen binding fragment thereof, having antigen binding regions of antibody K3-5H1. In one embodiment, the invention provides an antibody, or antigen-binding fragment thereof, comprising a heavy chain variable domain sequence as set forth in SEQ ID NO: 69, and a light chain variable domain sequence as set forth in SEQ ID NO: 70. In one embodiment, the invention is directed to an antibody having a heavy chain variable domain comprising the CDRs of SEQ ID NO: 69, and a light chain variable domain comprising the CDRs of SEQ ID NO: 70. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 69, and comprises a light chain variable region having an amino acid sequence that is at least 95% identical, at least 96% identical, at least 97% identical, at least 98% identical, or at least 99% identical to the sequence set forth in SEQ ID NO: 70. In one embodiment, the invention features an anti-KRAS antibody, or an antigen-binding portion thereof, comprising a heavy chain variable region comprising a CDR3 domain comprising the amino acid as set forth in SEQ ID NO: 281, a CDR2 domain comprising the amino acid sequence as set forth in SEQ ID NO: 280, and a CDR1 domain comprising the amino acid sequence as set forth in SEQ ID NO: 279; and comprising a light chain variable region comprising a CDR3 domain comprising the amino acid as set forth in SEQ ID NO: 284, a CDR2 domain comprising the amino acid sequence as set forth in SEQ ID NO: 283 and a CDR1 domain comprising the amino acid sequence as set forth in SEQ ID NO: 282. The antibody may be an IgG1 or an IgG4 isotype.

In one embodiment, the present invention is directed to an antibody, or an antigen binding fragment thereof, having antigen binding regions of antibody K3-5E2. In one embodiment, the invention provides an antibody, or antigen-binding fragment thereof, comprising a heavy chain variable domain sequence as set forth in SEQ ID NO: 71, and a light chain variable domain sequence as set forth in SEQ ID NO: 72. In one embodiment, the invention is directed to an antibody having a heavy chain variable domain comprising the CDRs of SEQ ID NO: 71, and a light chain variable domain comprising the CDRs of SEQ ID NO: 72. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 71, and comprises a light chain variable region having an amino acid sequence that is at least 95% identical, at least 96% identical, at least 97% identical, at least 98% identical, or at least 99% identical to the sequence set forth in SEQ ID NO: 72. In one embodiment, the invention features an anti-KRAS antibody, or an antigen-binding portion thereof, comprising a heavy chain variable region comprising a CDR3 domain comprising the amino acid as set forth in SEQ ID NO: 287, a CDR2 domain comprising the amino acid sequence as set forth in SEQ ID NO: 286, and a CDR1 domain comprising the amino acid sequence as set forth in SEQ ID NO: 285; and comprising a light chain variable region comprising a CDR3 domain comprising the amino acid as set forth in SEQ ID NO: 290, a CDR2 domain comprising the amino acid sequence as set forth in SEQ ID NO: 289 and a CDR1 domain comprising the amino acid sequence as set forth in SEQ ID NO: 288. The antibody may be an IgG1 or an IgG4 isotype.

In one embodiment, the present invention is directed to an antibody, or an antigen binding fragment thereof, having antigen binding regions of antibody K3-5F2. In one embodiment, the invention provides an antibody, or antigen-binding fragment thereof, comprising a heavy chain variable domain sequence as set forth in SEQ ID NO: 73, and a light chain variable domain sequence as set forth in SEQ ID NO: 74. In one embodiment, the invention is directed to an antibody having a heavy chain variable domain comprising the CDRs of SEQ ID NO: 73, and a light chain variable domain comprising the CDRs of SEQ ID NO: 74. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 73, and comprises a light chain variable region having an amino acid sequence that is at least 95% identical, at least 96% identical, at least 97% identical, at least 98% identical, or at least 99% identical to the sequence set forth in SEQ ID NO: 74. In one embodiment, the invention features an anti-KRAS antibody, or an antigen-binding portion thereof, comprising a heavy chain variable region comprising a CDR3 domain comprising the amino acid as set forth in SEQ ID NO: 293, a CDR2 domain comprising the amino acid sequence as set forth in SEQ ID NO: 292, and a CDR1 domain comprising the amino acid sequence as set forth in SEQ ID NO: 291; and comprising a light chain variable region comprising a CDR3 domain comprising the amino acid as set forth in SEQ ID NO: 296, a CDR2 domain comprising the amino acid sequence as set forth in SEQ ID NO: 295 and a CDR1 domain comprising the amino acid sequence as set forth in SEQ ID NO: 294. The antibody may be an IgG1 or an IgG4 isotype.

Antigen-binding fragments of antigen binding proteins of the invention may be produced by conventional techniques. Examples of such fragments include, but are not limited to, Fab and F(ab')2 fragments.

In certain embodiments, the present disclosure provides a Fab fully human antibody fragment, having a variable domain region from a heavy chain and a variable domain region from a light chain, wherein the heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71 and SEQ ID NO. 73, and that has a light chain variable domain sequence that is at least 95% identical, at least 96% identical, at least 97% identical, at least 98% identical, or at least 99% identical, to the amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72 and SEQ ID NO. 74.

Preferably, the fully human antibody Fab fragment has both a heavy chain variable domain region and a light chain variable domain region wherein the antibody has a heavy chain/light chain variable domain sequence selected from SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO.

29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 151/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72 and SEQ ID NO. 73/SEQ ID NO. 74.

Single chain antibodies may be formed by linking heavy and light chain variable domain (Fv region) fragments via an amino acid bridge (short peptide linker), resulting in a single polypeptide chain Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al. (1997) Prot. Eng. 10:423; Kortt et al. (2001) Biomol. Eng. 18:95-108). By combining different $V_L$ and $V_H$-comprising polypeptides, one can form multimeric scFvs that bind to different epitopes (Kriangkum et al. (2001) Biomol. Eng. 18:31-40). Techniques developed for the production of single chain antibodies include those described in U.S. Pat. No. 4,946,778; Bird (1988) Science 242:423; Huston et al. (1988) Proc. Natl. Acad. Sci. USA 85:5879; Ward et al. (1989) Nature 334:544, de Graaf et al. (2002) Methods Mol. Biol. 178:379-87.

In one embodiment, the present disclosure provides an scFv having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, or at least 99% identical, to the amino acid sequences selected from SEQ ID NO: 1 or SEQ ID NO. 3, and that has a light chain variable domain sequence that is at least 95% identical, at least 96% identical, at least 97% identical, at least 98% identical, or at least 99% identical, to the amino acid sequence selected from SEQ ID NO:2 or SEQ ID NO:4. In one embodiment, the scFv has both a heavy chain variable domain region and a light chain variable domain region, wherein the scFv has a heavy chain/light chain variable domain sequence selected from SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 151/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72 and SEQ ID NO. 73/SEQ ID NO. 74.

In one embodiment, the antibody of the invention is a human IgG1 antibody. In one embodiment, the antibody of the invention is a human IgG4 antibody.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al. (2002) Methods Mol. Biol. 178:303-16). Moreover, if an IgG4 is desired, it may also be desired to introduce a point mutation (CPSCP→CPPCP) (SEQ ID Nos. 143 and 144, respectively) in the hinge region (Bloom et al. (1997) Protein Science 6:407) to alleviate a tendency to form intra-H chain disulfide bonds that can lead to heterogeneity in the IgG4 antibodies.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al. (1993) Biochem. 32: 1180-1187; Kobayashi et al. (1997) Protein Eng. 12(10):879-884; and Burks et al. (1997) Proc. Natl. Acad. Sci. USA 94:412-417). Near et al. (1993) Mol. Immunol. 30:369-377 explains how to impact or not impact binding through site-directed mutagenesis. Near et al. only mutated residues that they thought had a high probability of changing antigen binding. Most had a modest or negative effect on binding affinity (Near et al., Table 3) and binding to different forms of digoxin (Near et al., Table 2).

Thus, the invention also includes, in certain embodiments, an antibody or a fragment thereof comprising light and/or heavy chain variable sequences having at least 95% identity to those sequences disclosed herein, wherein the antibody or fragment retains the characteristics of the parent antibody comprising the light and/or heavy chain variable sequences.

In certain embodiments, an antibody, or antigen-binding fragment thereof, provided herein has a dissociation constant ($K_D$) of $1\times10^{-6}$ M or less; $5\times10^{-7}$ M or less; $1\times10^{-7}$ M or less; $5\times10^{-8}$ M or less; $1\times10^{-8}$ M or less; $5\times10^{-9}$ M or less; or $1\times10^{-9}$ M or less. In one embodiment, the antibody, or antigen-binding fragment thereof, of the invention as a $K_D$ from $1\times10^{-7}$ M to $1\times10^{-10}$ M. In one embodiment, the antibody, or antigen-binding fragment thereof, of the invention as a $K_D$ from $1\times10^{-8}$ M to $1\times10^{-10}$ M.

Those of ordinary skill in the art will appreciate standard methods known for determining the $K_D$ of an antibody, or fragment thereof. For example, in one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al. (1999) J. Mol. Biol. 293:865-881).

According to another embodiment, $K_D$ is measured using a BIACORE surface plasmon resonance assay. The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.).

In particular embodiments, antigen binding proteins of the present invention have a binding affinity ($K_a$) for KRAS of at least $10^6$ M$^{-1}$. In other embodiments, the antigen binding proteins exhibit a $K_a$ of at least $10^7$ M$^{-1}$, at least $10^8$ M$^{-1}$, at least $10^9$ M$^{-1}$, or at least $10^{10}$ M$^{-1}$. In another embodiment, the antigen binding protein exhibits a $K_a$ substantially the same as that of an antibody described herein in the Examples.

In another embodiment, the present disclosure provides an antigen binding protein that has a low dissociation rate from KRAS. In one embodiment, the antigen binding protein has a $K_{off}$ of $1\times10^{-4}$ to sec$^{-1}$ or lower. In another embodiment, the $K_{off}$ is $5\times10^{-5}$ to sec$^{-1}$ or lower. In another embodiment, the $K_{off}$ is substantially the same as an antibody described herein. In another embodiment, the antigen binding protein binds to KRAS with substantially the same $K_{off}$ as an antibody described herein.

In another aspect, the present disclosure provides an antigen binding protein that inhibits an activity of KRAS. In one embodiment, the antigen binding protein has an IC$_{50}$ of 1000 nM or lower. In another embodiment, the IC$_{50}$ is 100 nM or lower; in another embodiment, the IC$_{50}$ is 10 nM or lower. In another embodiment, the IC$_{50}$ is substantially the same as that of an antibody described herein in the Examples. In another embodiment, the antigen binding protein inhibits an activity of KRAS with substantially the same IC$_{50}$ as an antibody described herein.

The present disclosure further provides multi-specific antigen binding proteins, for example, bispecific antigen binding protein, e.g., antigen binding protein that bind to two different epitopes of KRAS, or to an epitope of KRAS and an epitope of another molecule, via two different antigen binding sites or regions. Moreover, bispecific antigen binding protein as disclosed herein can comprise a KRAS binding site from one of the herein-described antibodies and a second KRAS binding region from another of the herein-described antibodies, including those described herein by reference to other publications. Alternatively, a bispecific antigen binding protein may comprise an antigen binding site from one of the herein described antibodies and a second antigen binding site from another KRAS antibody that is known in the art, or from an antibody that is prepared by known methods or the methods described herein.

Numerous methods of preparing bispecific antibodies are known in the art. Such methods include the use of hybridomas as described by Milstein et al. (1983) Nature 305:537, and chemical coupling of antibody fragments (Brennan et al. (1985) Science 229:81; Glennie et al. (1987) J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al. (1992) J. Immunol. 148:1547) or other lock and key interactive domain structures as described in U.S. Pat. No. 5,582,996. Additional useful techniques include those described in U.S. Pat. Nos. 5,959,083 and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Figure 2A:
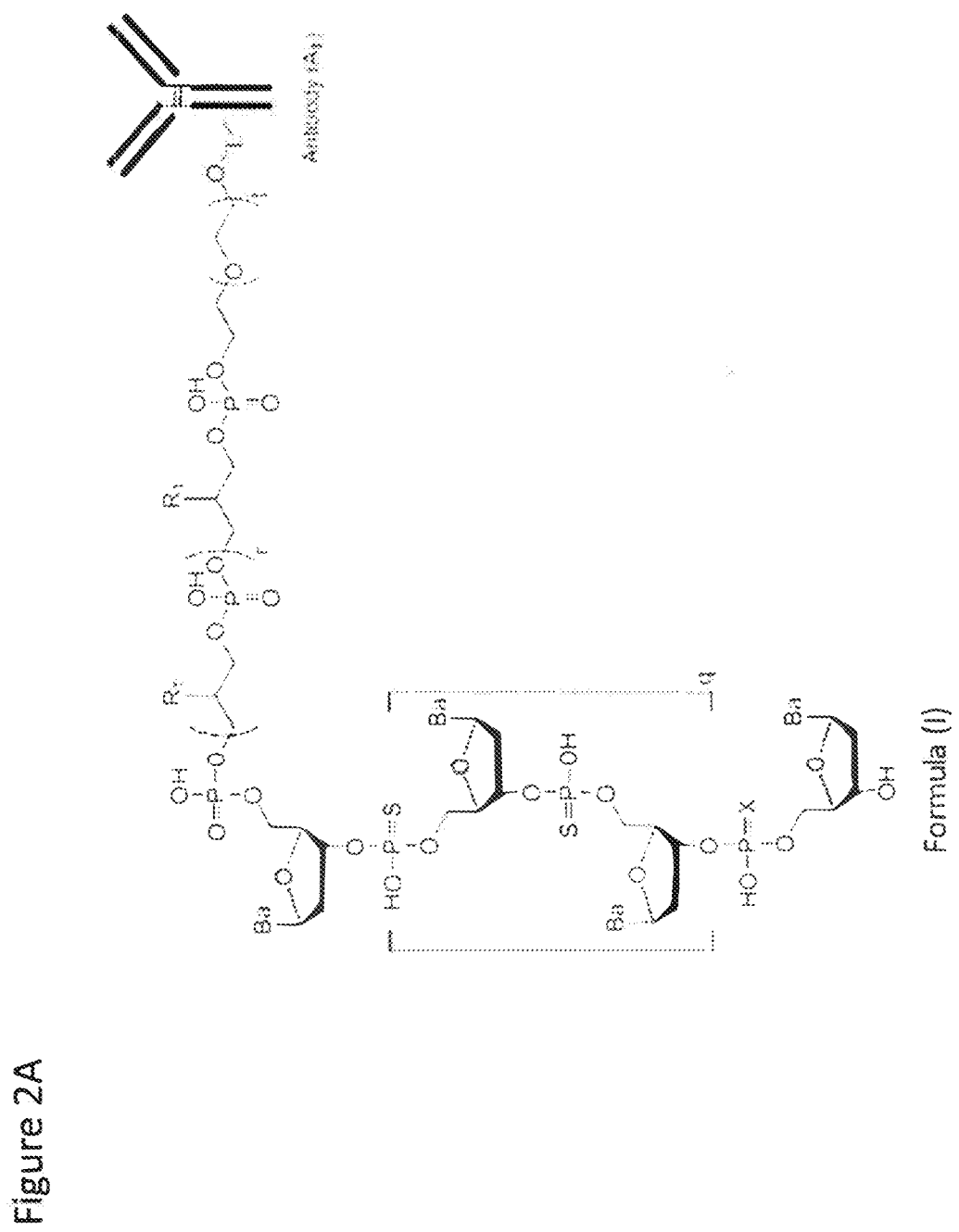
FIG. 2A is a drawing of an exemplary antibody conjugate of the present invention, comprising Formula (I), or a pharmaceutically acceptable salt thereof, wherein each of X, q, Ba, R1, r, t, L, and AT are as defined and described in U.S. Publication No. 20170107289, filed on Oct. 20, 2016; Provisional Appln. No. 62/327,130, filed on Apr. 25, 2016; U.S. Provisional Appln. No. 62/327,132, filed on Apr. 25, 2016; U.S. Provisional Appln. No. 62/327,136, filed on Apr. 25, 2016; and U.S. Provisional Appln. No. 62/327,137, filed on Apr. 25, 2016, each of which are incorporated by reference herein.
Figure 2B:
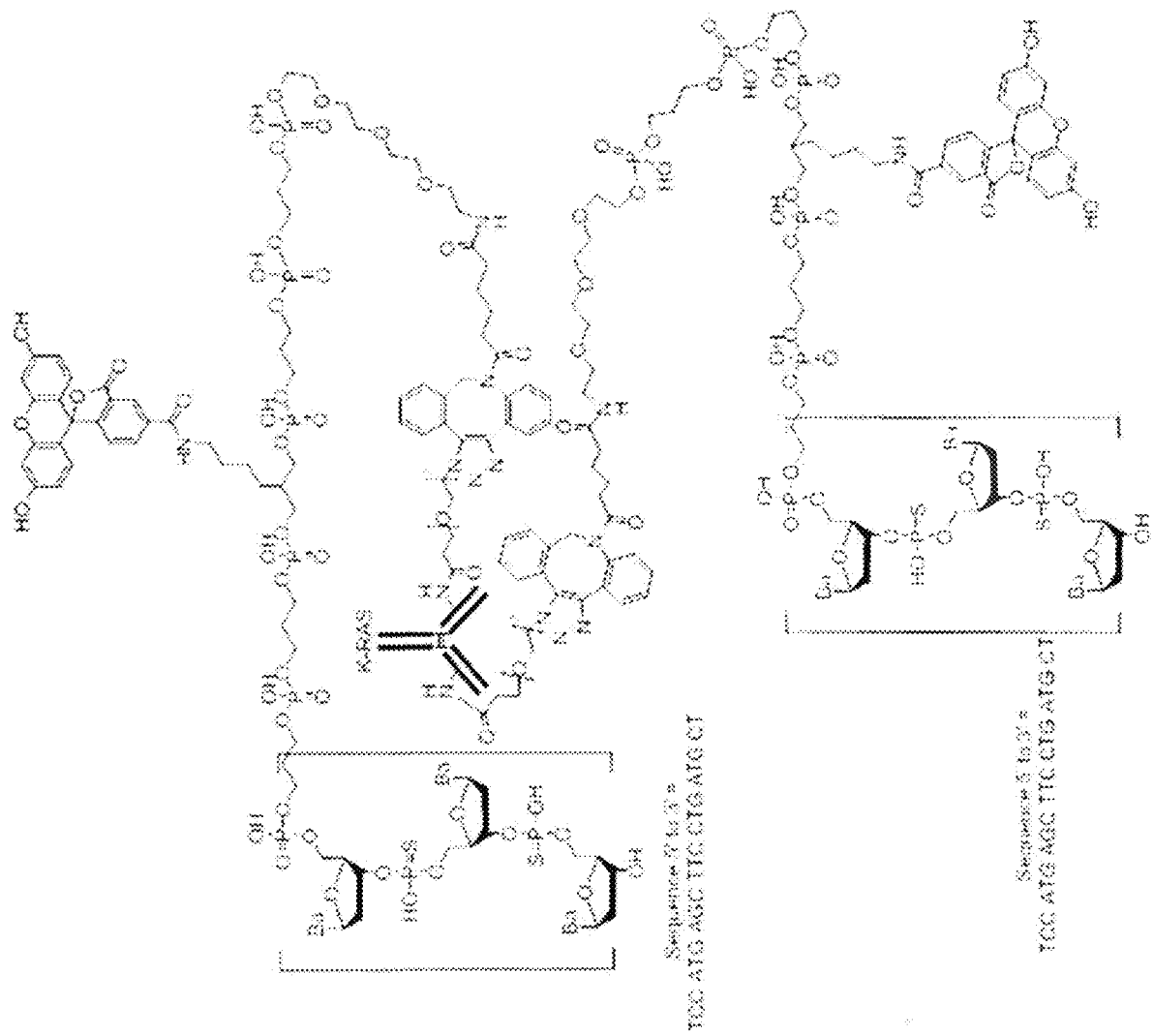
FIG. 2B is a drawing of an embodiment of FIG. 2A, showing an exemplary antibody conjugate of the present invention, where the antibody ($A_T$) is an anti-KRAS antibody and the conjugate is labeled with fluorescein.
Figure 2C:
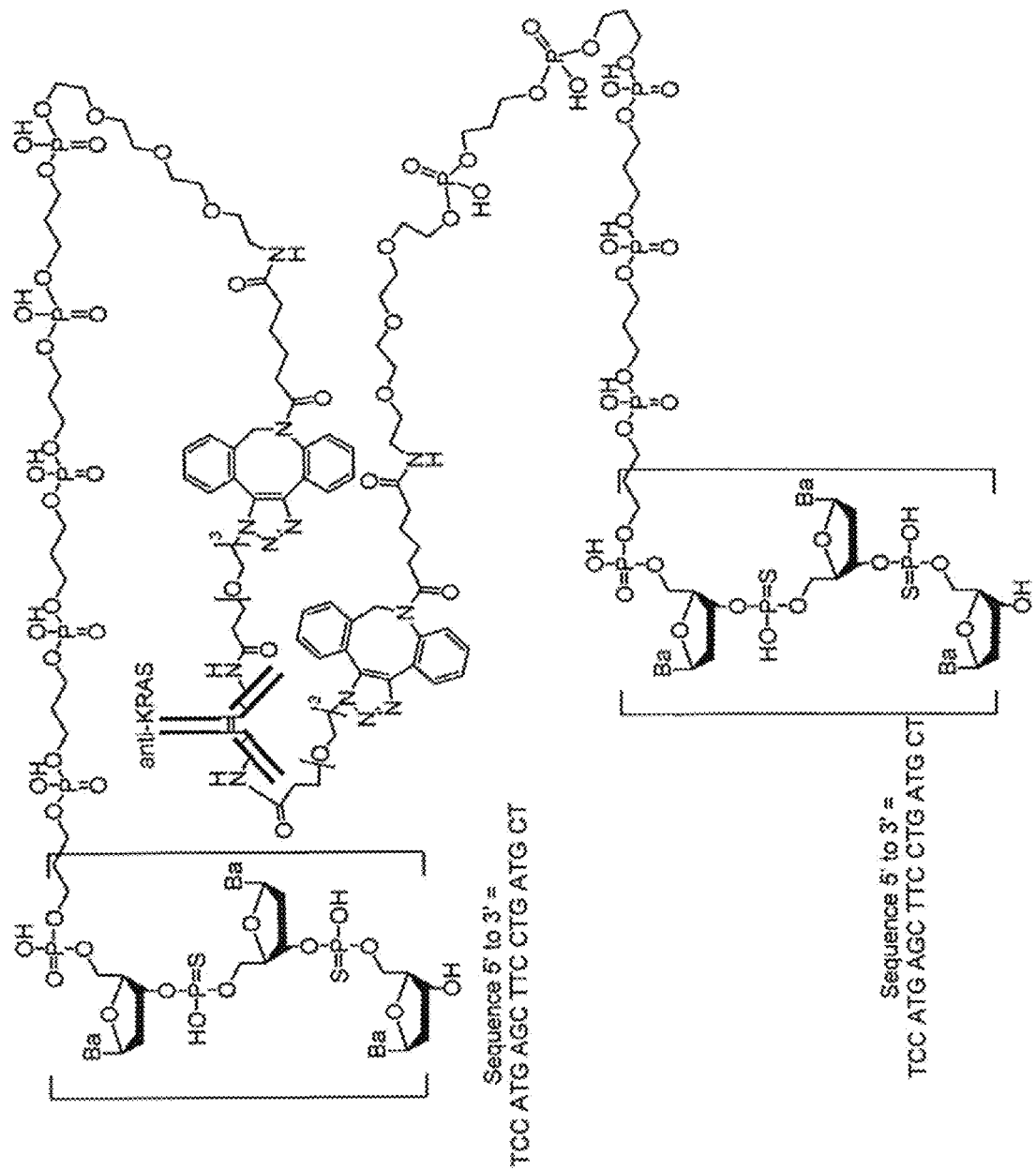
FIG. 2C is a drawing of an embodiment of FIG. 2A, showing an exemplary antibody conjugate of the present invention, where the antibody ($A_T$) is an anti-KRAS antibody, and which is tested in Examples 1-9. In further exemplary embodiments, the antibody ($A_T$) is anti-KRAS G12D 4F10 antibody. This conjugate is termed Compound 1.

In certain embodiments, the anti-KRAS antibody, or an antigen-binding fragment thereof is conjugated to an intracellular delivery compound. In one embodiment, the invention provides the compound of FIG. 2A. In one embodiment, the invention provides the compound of FIG. 2B. In one embodiment, the invention provides the compound of FIG. 2C. FIG. 2A is a drawing of an exemplary antibody conjugate of the present invention, comprising Formula (I), or a pharmaceutically acceptable salt thereof, wherein each of X, q, Ba, R1, r, t, L, and A$_T$ are as defined and described in U.S. Provisional Appln. No. 62/327,130, filed on Apr. 25, 2016, U.S. Provisional Appln. No. 62/327,132, filed on Apr. 25, 2016, U.S. Provisional Appln. No. 62/327,136, filed on Apr. 25, 2016, U.S. Provisional Appln. No. 62/327,137, filed on Apr. 25, 2016; and U.S. Publication No. 2017/0107289, filed on Oct. 20, 2016. FIG. 2B is a drawing of an embodiment of FIG. 2A, showing an exemplary antibody conjugate of the present invention, where the antibody (A$_T$) is an anti-KRAS antibody and the conjugate is labeled with fluorescein. FIG. 2C is a drawing of an embodiment of FIG. 2A, showing an exemplary antibody conjugate of the present invention, where the antibody (A$_T$) is an anti-KRAS antibody, and which is tested in Examples 1-9. In further exemplary embodiments, the antibody (A$_T$) is anti-KRAS G12D 4F10 antibody. This conjugate is termed Compound 1.

Oligomers that contain one or more antigen binding proteins may be employed as KRAS antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have KRAS binding activity.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al. (1988) Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al. (1994) FEBS Letters 344:191. The use of a modified leucine zipper that allows for stable trimerization of a heterologous protein fused thereto is described in Fanslow et al. (1994) Semin. Immunol. 6:267-78. In one approach, recombinant fusion proteins comprising an anti-KRAS antibody fragment or derivative fused to a leucine zipper peptide are expressed in suitable host cells, and the soluble oligomeric anti-KRAS antibody fragments or derivatives that form are recovered from the culture supernatant.

Antigen binding proteins directed against KRAS can be used, for example, in assays to detect the presence of KRAS polypeptides, either in vitro or in vivo. The antigen binding proteins also may be employed in purifying KRAS proteins by immunoaffinity chromatography. Blocking antigen binding proteins can be used in the methods disclosed herein. Such antigen binding proteins that function as KRAS antagonists may be employed in treating any KRAS-induced condition, including but not limited to various cancers.

Antigen binding proteins may be employed in an in vitro procedure, or administered in vivo to inhibit KRAS-induced biological activity. Disorders that would benefit (directly or indirectly) from activation of KRAS, examples of which are provided herein, thus may be treated. In one embodiment, the present invention provides a therapeutic method comprising in vivo administration of a KRAS blocking antigen binding protein to a mammal in need thereof in an amount effective for reducing a KRAS-induced biological activity.

In certain embodiments of the invention, antigen binding proteins include fully human monoclonal antibodies that inhibit a biological activity of KRAS.

Antigen binding proteins, including antibodies and antibody fragments described herein, may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides, including antibodies and antibody fragments described herein, of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al. (1981) Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al. (1991) EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of KRAS bound thereto. Polypeptides contemplated for use herein include substantially homogeneous recombinant mammalian anti-KRAS antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-KRAS antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Polypeptides of the present disclosure can be produced using any standard methods known in the art. In one example, the polypeptides are produced by recombinant DNA methods by inserting a nucleic acid sequence (a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for E. coli and other bacteria, as well as mammalian cells, plant cells, yeast cells and insect cells.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers (1988) *Bio/Technology* 6:47). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

KRAS-binding polypeptides can also be produced by chemical synthesis (such as by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the present disclosure provides monoclonal antibodies that bind to KRAS. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen-binding fragments of antigen binding proteins of the invention may be produced by conventional techniques known in the art.

Post-Translational Modifications of Antibodies

In certain embodiments, the antibodies (or fragments thereof) of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See Raju et al. (2001) *Biochem.* 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. No. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$—CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al. (1995) *Bioconjugate Chem.* 6:62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life (t$_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half-life, such as the half-life of the protein in the serum or other bodily fluid of an animal Therapeutic Methods, Formulations and Modes of Administration Any of the anti-KRAS antibodies or antigen binding fragments disclosed herein may be used in such therapeutic methods. Examples of anti-KRAS antibodies and antigen binding fragments that may be used in the therapeutic methods and compositions of the invention are described above.

In one embodiment, the anti-KRAS antibodies and antibody fragments of the invention are used to treat cancer, particularly cancer associated with detrimental. In one embodiment, the anti-KRAS antibodies and antibody fragments of the invention are used to treat pancreatic cancer. In one embodiment, the anti-KRAS antibodies and antibody fragments of the invention are used to treat lung cancer. In one embodiment, the anti-KRAS antibodies and antibody fragments of the invention are used to treat colorectal cancer.

The present disclosure further provides a method for treating cancer, comprising administering an anti-KRAS antibody or antigen-binding fragment, disclosed herein, including antibodies or fragments comprising the variable regions or CDRs of the heavy and light chains described in Table 4. In one embodiment, the invention provides a method of treating cancer by administering an anti-human KRAS antibody to a subject in need thereof.

Mutant RAS oncogenes have been implicated in about 30 percent of human cancers, and KRAS is its most prominent and aggressive member. Mutant KRAS drives particularly hard-to-treat cancers, including pancreatic, lung, and colorectal cancers. Accordingly, anti-KRAS antibodies and antibody fragments of the invention may be used to treat a subject having cancer which is associated with a KRAS mutation, e.g., a KRAS G12D mutation.

Additional types of cancer that may be treated using anti-KRAS antibodies and fragments of the invention, include, but are not limited to, pancreatic cancer, lung cancer, including non-small cell lung cancer, colorectal cancer, prostate cancer, breast cancer, ovarian cancer, head and neck cancer, bladder cancer, melanoma, colorectal cancer, leiomyoma, leiomyosarcoma, glioma, glioblastoma, esophageal cancer, liver cancer, kidney cancer, stomach cancer, colon cancer, cervical cancer, uterine cancer, liver cancer and a hematological cancer.

In one embodiment, the anti-KRAS antibodies or fragments thereof of the invention are used to treating a subject having pancreatic cancer. Pancreatic cancer is a malignant neoplasm originating from transformed cells arising in tissues forming the pancreas. Pancreatic cancer is one of the most common causes of cancer-related deaths in the world. Due to the absence of specific symptoms, the lack of early detection techniques, and highly aggressive phenotypes, pancreatic cancer is usually diagnosed at an advanced-incurable and metastatic stages. Oncogenic KRAS mutation is the signature genetic event in the progression and growth of pancreatic ductal adenocarcinoma (PDAC), an almost universally fatal disease. Although oncogenic KRAS was first associated with PDAC decades ago, exome sequencing established that KRAS is the most frequently mutated gene in PDAC (95%), the predominant form of pancreatic cancer (90%). The frequency and specific substitutions show cancer type differences, with 98% of KRAS mutations in PDAC occurring at position G12. Of the eight different substitutions found at this position, the predominant substitution is G12D.

In one embodiment, the anti-KRAS antibodies or fragments thereof of the invention are used to treating a subject having lung cancer. In further embodiments, the lung cancer is non small cell lung cancer. Approximately 15-25% of patients with lung adenocarcinoma have tumor associated KRAS mutations. KRAS mutations are uncommon in lung squamous cell carcinoma (Brose et al. (2002) Cancer Res. 62(23):6997-7000). In the majority of cases, these mutations are missense mutations which introduce an amino acid substitution at position 12, 13, or 61. The result of these mutations is constitutive activation of KRAS signaling pathways. In the vast majority of cases, KRAS mutations are found in tumors wild type for EGFR or ALK; in other words, they are non-overlapping with other oncogenic mutations found in NSCLC. Therefore, KRAS mutation defines a distinct molecular subset of the disease.

In one embodiment, the anti-KRAS antibodies or fragments thereof of the invention are used to treating a subject having colorectal cancer. Colorectal cancer (CRC) is the second leading cause of cancer-related death in the United States. The development of CRC is a multistep process characterized by accumulation of genetic alterations that have long been considered to occur in a stepwise process. Along the progression from normal colonic epithelial cells, small adenoma, advanced adenoma, and finally to carcinoma, the KRAS oncogene mutation has a role in a significant proportion of CRCs. KRAS has been reported to be mutated in about 30% of colorectal adenomas and 30% to 50% of CRCs (Russo et al. (2005) Ann Oncol. 16(suppl 4):iv44-iv49; Nosho et al. (2008) PLoS One. 3:e3698).

In one embodiment, the anti-KRAS antibodies or fragments thereof of the invention are used to treating a subject having a precursor lesion. In one embodiment, the anti-KRAS antibodies or fragments thereof of the invention are used to treating a subject having metastatic cancer, including metastatic forms of the aforementioned cancers.

Anti-KRAS antibodies and antibody fragments of the invention can be administered alone or in combination with one or more additional therapies such as chemotherapy radiotherapy, immunotherapy, surgical intervention, for the treatment of cancer. Long-term therapy is equally possible as is adjuvant therapy in the context of other treatment strategies.

Additional agents for treatment can be administered, together (simultaneously) or at different times (sequentially) to the anti-KRAS antibody or antigen binding fragment thereof.

The present disclosure also provides a method of inhibiting growth of a tumor in a subject where an anti-KRAS antibody, or antigen-binding fragment thereof, of the invention is administered to a subject having a tumor.

Further, antibodies and antibody fragments to KRAS described herein can be combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In certain embodiments, an anti-KRAS antibody or antibody fragment disclosed herein may be combined with a vaccination protocol. Many experimental strategies for vaccination against tumors have been devised. In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg (1999) Immunity 10: 281-7). In many cases, these tumor specific antigens are differentiation antigens expressed in the tumors and in the cell from which the tumor arose, for example melanocyte antigens gp100, MAGE antigens, and Trp-2. Many of these antigens can be shown to be the targets of tumor specific T cells found in the host. An anti-KRAS antibody or antibody fragment disclosed herein can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). (These somatic tissues may be protected from immune attack by various means). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with an anti-KRAS antibody or antibody fragment disclosed herein is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with KRAS blockade to activate more potent anti-tumor responses.

An anti-KRAS antibody or antibody fragment disclosed herein can also be combined with other cancer treatments. An anti-KRAS antibody or antibody fragment disclosed herein can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-KRAS antibody in combination with decarbazine for the treatment of melanoma. Another example of such a combination is an anti-KRAS antibody in combination with interleukin-2 (IL-2) for the treatment of melanoma. The scientific rationale behind the combined use of KRAS blockade and chemotherapy is that cell death, that is a consequence of the cytotoxic action of most chemotherapeutic compounds, should result in increased levels of tumor antigen in the antigen presentation pathway. Other combination therapies that may result in synergy with an anti-KRAS antibody or antibody fragment disclosed herein through cell death are radiation, surgery, and hormone deprivation. Each of these protocols creates a source of tumor antigen in the host. Angiogenesis inhibitors can also be combined with an anti-KRAS antibody or antibody fragment disclosed herein. Inhibition of angiogenesis often leads to tumor cell death which may feed tumor antigens into host antigen presentation pathways.

In some embodiments, the anti-KRAS antibodies and antibody fragments of the invention may be administered in conjunction with a chemotherapy or chemotherapeutic agent. In some embodiments, the anti-KRAS antibodies and antibody fragments of the invention may be administered in conjunction with a radiation therapy or radiotherapeutic agent. In some embodiments, the anti-KRAS antibodies and antibody fragments of the invention may be administered in conjunction with a targeted therapy or targeted therapeutic agent. In some embodiments, the anti-KRAS antibodies and antibody fragments of the invention may be administered in conjunction with an immunotherapy or immunotherapeutic agent, for example a monoclonal antibody.

In certain embodiments of such methods, one or more anti-KRAS antibodies and antibody fragments of the invention can be administered, together (simultaneously) or at different times (sequentially). In addition, anti-KRAS antibodies and antibody fragments of the invention can be administered with another type of compound(s) for treating cancer or for inhibiting angiogenesis.

The disclosed human anti-KRAS antibodies can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of the anti-KRAS antibodies and antibody fragments of the invention, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the use of an anti-KRAS antibody or antibody fragment disclosed herein. Alternatively, antigen may be delivered directly to DCs by the use of bispecific antibodies which bind to tumor antigen and a dendritic cell specific cell surface marker.

Anti-KRAS antibodies or antibody fragments disclosed herein can also be used in combination with bispecific antibodies that target, for example, Fcα or Fcγ receptor-expressing effectors cells to tumor cells (U.S. Pat. Nos. 5,922,845 and 5,837,243).

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-KRAS antibodies and antibody fragments described herein to counteract the effects of the immunosuppressive agent and favor tumor immune responses by the host.

Suitable routes of administering the antibody compositions described herein (e.g., human monoclonal antibodies, multispecific and bispecific molecules and immunoconjugates) are in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

Techniques and dosages for administration vary depending on the type of specific binding protein and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions comprising the antigen binding proteins of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

Thus, an anti-KRAS antibody, or antigen binding portion thereof, of the invention can be incorporated into a pharmaceutical composition suitable for parenteral administration. Preferably, the anti-KRAS antibody, or antigen binding portion thereof, will be prepared as an injectable solution containing 0.1-250 mg/ml antibody. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, an anti-KRAS antibody, or antigen binding portion thereof, described herein is administered by intravenous infusion or injection. In another preferred embodiment, an anti-KRAS antibody, or antigen binding portion thereof, is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The anti-KRAS antibody, or antigen binding portion thereof, of the present invention can be administered by a variety of methods known in the art, although for many therapeutic applications, the preferred route/mode of administration is subcutaneous injection, intravenous injection, or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., (Marcel Dekker, Inc., New York, 1978).

A therapeutically effective dose refers to a dose that produces the therapeutic effects for which it is administered. The exact dose will depend on the disorder to be treated, and may be ascertained by one skilled in the art using known techniques. In general, the anti-KRAS antibody, or fragment thereof, is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

In certain embodiments, the subject anti-KRAS antibodies or antibody fragments of the invention can be used alone.

Diagnostics and Kits

In certain embodiments, any of the anti-KRAS antibodies (or fragments) provided herein are useful for detecting the presence of KRAS in vitro, e.g., in a biological sample, or in vivo. Such detection methods using the anti-KRAS antibodies (or fragments) disclosed herein may be used for diagnostic purpose. Exemplary disorders that may be diagnosed using an antibody of the invention include cancer.

The antibodies and fragments of the invention may be used to detect the presence of KRAS in a biological sample. In certain embodiments, the method comprises contacting the biological sample with an anti-KRAS antibody (or fragment) as described herein under conditions permissive for binding of the anti-KRAS antibody to KRAS, and detecting whether a complex is formed between the anti-KRAS antibody and KRAS. Such method may be an in vitro or in vivo method. In one embodiment, an anti-KRAS antibody is used to select subjects eligible for therapy with an anti-KRAS antibody, e.g. where KRAS is a biomarker for selection of patients. A biological sample may be a cell or tissue, such as a sample of a tumor (e.g., pancreatic, lung or colorectal).

In certain embodiments, the binding polypeptides of fragments thereof can be labeled or unlabeled for diagnostic purposes. Typically, diagnostic assays entail detecting the formation of a complex resulting from the binding of an antibody or fragment to KRAS. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present disclosure can be utilized in enzyme immunoassays, wherein the subject polypeptides are conjugated to an enzyme. When a biological sample comprising a KRAS protein is combined with the subject binding polypeptides, binding occurs between the binding polypeptides and the KRAS protein. In one embodiment, a sample containing cells expressing a KRAS protein (e.g., endothelial cells) is combined with the subject antibodies, and binding occurs between the binding polypeptides and cells bearing a KRAS protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a KRAS protein in a biological sample using the antibodies or fragments thereof of the invention can also be prepared. Such kits will include a KRAS binding polypeptide, e.g., antibodies or fragments thereof, which binds to a KRAS protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin) For example, the binding polypeptides and/or antibodies can be provided as a lyophilized mixture with the adjunct ingredients, or the adjunct ingredients can be separately provided for combination by the user. Generally, these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Other embodiments are described in the following non-limiting Examples.

EXAMPLES

Example 1. Identification of Human Anti-KRAS Antibodies

Recombinant human antibodies specific for human KRAS were identified and selected for therapeutic characteristics, including specificity for human KRAS and a high affinity for KRAS (e.g., at least $10^{-6}$ M). Affinity data for antibodies 1E3, 4E10, 5C5 and 5F8 are shown below in Table 1.

TABLE 1

|      | ka (1/Ms) | kd (1/s) | KD (M)   | Rmax (RU) | Chi$^2$ (RU$^2$) | U-value |
|------|-----------|----------|----------|-----------|------------------|---------|
| 1E3  | 2.69E+05  | 0.00113  | 4.20E−09 | 9.971     | 0.525            | 7       |
| 4E10 | 1.35E+05  | 0.001299 | 9.60E−09 | 10.14     | 0.232            | 5       |
| 5C5  | 1.66E+05  | 0.001099 | 6.63E−09 | 9.389     | 0.74             | 9       |
| 5F8  | 1.82E+05  | 0.002285 | 1.26E−08 | 11.98     | 0.287            | 4       |

The amino acid sequences of the heavy and light chain variable domains of the identified anti-KRAS antibodies, and their complementarity determining regions (CDRs), are described in Table 2, below.

TABLE 2

Antibody Amino Acid Sequences

| | Heavy chain variable domain regions | Light chain variable domain regions |
|---|---|---|
| K3-1F4 | EVQLVQSGGGVVQPGRSLRLSCAAS<u>GFTS SNYGMH</u>WVRQAPGKGLEWVA<u>VISHDGSKK YYADSVKG</u>RFTISRDNSKNTLFVQLSSLR PEDTAVYYCAT<u>SLYSSMDL</u>WGQGTTVTVS S<br>SEQ ID NO. 1 | QSVVTQPPSVSAAPGQKVTISC<u>SGSNSNI GKNYVS</u>WFQQVPGTAPKLLIF<u>EDNQRPSG</u> IPDRFSASKSGTSASLAISGLQSEDEADY YC<u>AAWDDSLNAHWV</u>FGGGTKLTVL<br>SEQ ID NO. 2 |
| K3-1F4 | HC CDR1<br>GFTSSNYGMH<br>SEQ ID NO. 75<br>HC CDR2<br>VISHDGSKKYYADSVKG<br>SEQ ID NO. 76<br>HC CDR3<br>SLYSSMDL<br>SEQ ID NO. 77 | LC CDR1<br>SGSNSNIGKNYVS<br>SEQ ID NO. 78<br>LC CDR2<br>EDNQRPS<br>SEQ ID NO. 79<br>LC CDR3<br>AAWDDSLNAHWV<br>SEQ ID NO. 80 |
| K3-1A7 | QVQLVESGGGVVQPGRSLRLSCTNS<u>GFSF SGYAMH</u>WVRQAPGKGLEWVA<u>VISFDGSHK YYADSVKG</u>RFTISRDNSKNTLYLHMNSLR AEDTAVYYCAS<u>GGNYYGSGTIVSHGLDF</u>W GQGTTVTVSS<br>SEQ ID NO. 3 | DIVMTQSPSTLSASVGDRVTITC<u>RASQSI SSWLA</u>WYQQKPGKAPKVLIY<u>KASSLESGV</u> PSRFSGSGSGTEFTLTISSLQPDDFAAYY CQ<u>HYNSYPYT</u>FGQGTKLEIK<br>SEQ ID NO. 4 |
| K3-1A7 | HC CDR1<br>GFSFSGYAMH<br>SEQ ID NO. 81<br>HC CDR2<br>VISFDGSHKYYADSVKG<br>SEQ ID NO. 82<br>HC CDR3<br>GGNYYGSGTIVSHGLDF<br>SEQ ID NO. 83 | LC CDR1<br>RASQSISSWLA<br>SEQ ID NO. 84<br>LC CDR2<br>KASSLES<br>SEQ ID NO. 85<br>LC CDR3<br>QHYNSYPYT<br>SEQ ID NO. 86 |
| K3-2B2 | QVQLVESGGGVVQPGRSLRLSCTNS<u>GFSF SGYAMH</u>WVRQAPGKGLEWVA<u>VISFDGSHK YYADSVKG</u>RFTISRDNSKNTLYLHMNSLR AEDTAVYYCAS<u>GGNYYGSGTIVSHGMDV</u>W GQGTTVTVSS<br>SEQ ID NO. 5 | SSELTQDPAVSVALGQTVRITC<u>QGDSLRS YYAS</u>WYQQKPGQAPVLVIY<u>GKNNRPS</u>GIP DRFSGSSSGNTASLTITGAQAEDEADYYC <u>NSRDSSGNH</u>RGGGTKLTVL<br>SEQ ID NO. 6 |
| K3-2B2 | HC CDR1<br>GFSFSGYAMH<br>SEQ ID NO. 87<br>HC CDR2<br>VISFDGSHKYYADSVKG<br>SEQ ID NO. 88<br>HC CDR3<br>GGNYYGSGTIVSHGMDV<br>SEQ ID NO. 89 | LC CDR1<br>QGDSLRSYYAS<br>SEQ ID NO. 90<br>LC CDR2<br>GKNNRPS<br>SEQ ID NO. 91<br>LC CDR3<br>NSRDSSGNH<br>SEQ ID NO. 92 |

TABLE 2-continued

Antibody Amino Acid Sequences

| | Heavy chain variable domain regions | Light chain variable domain regions |
|---|---|---|
| K3-2C2 | QVQLVESGGGVVQPGRSLRLSCSNS<u>GFSF</u><br><u>SGYTMH</u>WVRQAPGKGLEWVA<u>VISFDGSHK</u><br><u>YYADSVKG</u>RFTISRDNSKNTLYLHMNSLR<br>AEDTAVYYCAK<u>KMHYGSGAYHFDL</u>WGQGT<br>LVTVSS<br>SEQ ID NO. 7 | DIVMTQSPSSLSASVGDRVTITC<u>RASQSI</u><br><u>SNYLN</u>WYQQKPGKAPKLLIY<u>AASSLQS</u>GV<br>PSRFSGSGSGTDFTLTISSLQPEDFATYY<br>C<u>QQSYSSPFT</u>FGPGTKVDIK<br>SEQ ID NO. 8 |
| K3-2C2 | HC CDR1<br>GFSFSGYTMH<br>SEQ ID NO. 93<br>HC CDR2<br>VISFDGSHKYYADSVKG<br>SEQ ID NO. 94<br>HC CDR3<br>KMHYGSGAYHFDL<br>SEQ ID NO. 95 | LC CDR1<br>RASQSISNYLN<br>SEQ ID NO. 96<br>LC CDR2<br>AASSLQS<br>SEQ ID NO. 97<br>LC CDR3<br>QQSYSSPFT<br>SEQ ID NO. 98 |
| K3-2H8 | EVQLLESGGGVVQPGRSLRLSCTNS<u>GFSF</u><br><u>SGYAMH</u>WVRQAPGKGLEWVA<u>VISFDGSHK</u><br><u>YYADSVKG</u>RFTISRDNSKNTLYLHMNSLT<br>AEDTAVYYCAS<u>GGNYYGSGTIVSHGMDV</u>W<br>GQGTTVTVSS<br>SEQ ID NO. 9 | QSVLTQPASVSGSPGQSITISC<u>TGTSSDV</u><br><u>GGYNYVS</u>WYQQHPGKAPKLMIY<u>DVSNRPS</u><br>GVSNRFSGSKSGNTASLTISGLQAEDEAD<br>YYC<u>SSYTSSSTLVV</u>FGGGTKLTVL<br>SEQ ID NO. 10 |
| K3-2H8 | HC CDR1<br>GFSFSGYAMH<br>SEQ ID NO. 99<br>HC CDR2<br>VISFDGSHKYYADSVKG<br>SEQ ID NO. 100<br>HC CDR3<br>GGNYYGSGTIVSHGMDV<br>SEQ ID NO. 101 | LC CDR1<br>TGTSSDVGGYNYVS<br>SEQ ID NO. 102<br>LC CDR2<br>DVSNRPS<br>SEQ ID NO. 103<br>LC CDR3<br>SSYTSSSTLVV<br>SEQ ID NO. 104 |
| K3-3E8 | EVQLLEPGGGVVQPGRSLRLSCTNS<u>GFSF</u><br><u>SGYAMH</u>WVRQAPGKGLEWVA<u>VISFDGSHK</u><br><u>YYADSVKG</u>RFTISRDNSKNTLYLHMNSLR<br>AEDTAVYYCAS<u>GGNYYGSGTIVSHGMDV</u>W<br>GQGTTVTVSS<br>SEQ ID NO. 11 | QSALTQPRSVSGSPGQSVTISC<u>TGTSSNV</u><br><u>GGYNHVS</u>WYQQHPGKAPKVIIY<u>DVNKRPS</u><br>GVSHRFSGSKSANTASLTISGLQAEDEAD<br>YYC<u>SSYTTSSTYV</u>FGTGTKLTVL<br>SEQ ID NO. 12 |
| K3-3E8 | HC CDR1<br>GFSFSGYAMH<br>SEQ ID NO. 105<br>HC CDR2<br>VISFDGSHKYYADSVKG<br>SEQ ID NO. 106<br>HC CDR3<br>GGNYYGSGTIVSHGMDV<br>SEQ ID NO. 107 | LC CDR1<br>TGTSSNVGGYNHVS<br>SEQ ID NO. 108<br>LC CDR2<br>DVNKRPS<br>SEQ ID NO. 109<br>LC CDR3<br>SSYTTSSTYV<br>SEQ ID NO. 110 |
| K3-4D9 | QVQLVESAGGVVQPGRSLRLSCTNS<u>GFSF</u><br><u>SGYAMH</u>WVRQAPGKGLEWVA<u>VISFDGSHK</u><br><u>YYADSVKG</u>RFTISRDNSKNTLYLHMNSLT<br>AEDTAVYYCAS<u>GGNYYGSGTIVSHGMDV</u>W<br>GQGTTVTVSS<br>SEQ ID NO. 13 | QSVLTQPASVSGSPGQSITISC<u>TGTSSDV</u><br><u>GGYKYVS</u>WYQQYPGKAPKLMIY<u>DVSKRPS</u><br>GVSNRFSGSKSGNTASLTISGLQAEDEAD<br>YYC<u>NSYTSSRIYV</u>FGTGTKLTVL<br>SEQ ID NO. 14 |
| K3-4D9 | HC CDR1<br>GFSFSGYAMH<br>SEQ ID NO. 111<br>HC CDR2<br>VISFDGSHKYYADSVKG<br>SEQ ID NO. 112<br>HC CDR3<br>GGNYYGSGTIVSHGMDV<br>SEQ ID NO. 113 | LC CDR1<br>TGTSSDVGGYKYVS<br>SEQ ID NO. 114<br>LC CDR2<br>DVSKRPS<br>SEQ ID NO. 115<br>LC CDR3<br>NSYTSSRIYV<br>SEQ ID NO. 116 |
| K3-4F10 | EVQLLEPGGGVVQPGRSLRLSCTNS<u>GFSF</u><br><u>SGYAMH</u>WVRQAPGKGLEWVA<u>VISFDGSHK</u><br><u>YYADSVKG</u>RFTISRDNSKNTLYLHMNSLR<br>AEDTAVYYCAS<u>GGNYYGSGTIVSHGMDV</u>W<br>GQGTTVTVSS<br>SEQ ID NO. 15 | QSVLTQPASVSGSPGQSITISC<u>TGTSNDI</u><br><u>GAYNYVS</u>WYQQHPGKAPKLMIY<u>DVNNRPS</u><br>GVPDRFSGSKSGNMASLTISGLQAEDDAD<br>YYC<u>SSYTSSSTLVV</u>FGGGTKLTVL<br>SEQ ID NO. 16 |

TABLE 2-continued

Antibody Amino Acid Sequences

| | Heavy chain variable domain regions | Light chain variable domain regions |
|---|---|---|
| K3-4F10 | HC CDR1<br>GFSFSGYAMH<br>SEQ ID NO. 117<br>HC CDR2<br>VISFDGSHKYYADSVKG<br>SEQ ID NO. 118<br>HC CDR3<br>GGNYYGSGTIVSHGMDV<br>SEQ ID NO. 119 | LC CDR1<br>TGTSNDIGAYNYVS<br>SEQ ID NO. 120<br>LC CDR2<br>DVNNRPS<br>SEQ ID NO. 121<br>LC CDR3<br>SSYTSSSTLVV<br>SEQ ID NO. 122 |
| K3-5H6 | QVQLVQSGGGVVQPGRSLRLSCTNS<u>GFSF</u><br><u>SGYAMH</u>WVRQAPGKGLEWVA<u>VISFDGSHK</u><br><u>YYADSVK</u>GRFTISRDNSKNTLYLHMNSVR<br>AEDTAVYYCAS<u>GGNHYGSGTIVSHGMDVR</u><br>GQGTTVTVSS<br>SEQ ID NO. 17 | QSVLTQPASVSGSPGQSITISC<u>TGTSSDI</u><br><u>GGSNWVS</u>WYQQHPGKAPKLMIY<u>DVSKRPS</u><br>GVSNRFSGSKSGNTASLTISGLQAEDEAD<br>YYC<u>SSYTSSSTYV</u>FGTGTKLTVL<br>SEQ ID NO. 18 |
| K3-5H6 | HC CDR1<br>GFSFSGYAMH<br>SEQ ID NO. 123<br>HC CDR2<br>VISFDGSHKYYADSVKG<br>SEQ ID NO. 124<br>HC CDR3<br>GGNHYGSGTIVSHGMDV<br>SEQ ID NO. 125 | LC CDR1<br>TGTSSDIGGSNWVS<br>SEQ ID NO. 126<br>LC CDR2<br>DVSKRPS<br>SEQ ID NO. 127<br>LC CDR3<br>SSYTSSSTYV<br>SEQ ID NO. 128 |
| K5-1F12 | QVQLVESGGGLVQPGGSLRLSCAAS<u>GFTF</u><br><u>SSYWMS</u>WVRQAPGKGLEWVG<u>FIRSKAYGG</u><br><u>TTEYAASVK</u>GRFTISRDDSKSIAYLQMNS<br>LKTEDTAVYYCTR<u>DGGSYFDY</u>WGQGTLVT<br>VSS<br>SEQ ID NO. 19 | QAGLTQPASVSGSPGQSITISC<u>TGTSSDV</u><br><u>GGYNYVS</u>WYQQHPGKAPKLMIY<u>DVSKRPS</u><br>GVSNRFSGSKSGNTASLTISGLQAEDEAD<br>YYC<u>SSYTSSSTYV</u>FGTGTKVTVL<br>SEQ ID NO. 20 |
| K5-1F12 | HC CDR1<br>GFTFSSYWMS<br>SEQ ID NO. 129<br>HC CDR2<br>FIRSKAYGGTTEYAASVKG<br>SEQ ID NO. 130<br>HC CDR3<br>DGGSYFDY<br>SEQ ID NO. 131 | LC CDR1<br>TGTSSDVGGYNYVS<br>SEQ ID NO. 132<br>LC CDR2<br>DVSKRPS<br>SEQ ID NO. 133<br>LC CDR3<br>SSYTSSSTYV<br>SEQ ID NO. 134 |

Example 2. Affinity Maturation

Affinity maturation was performed on the anti-hKRAS antibodies described in Example 1. The amino acid sequences of the heavy and light chain variable domains of the affinity matured anti-KRAS antibodies, and their CDRs, are described in Table 3. To improve the affinity of the anti-KRAS antibodies, affinity maturation was carried out using site specific random mutagenesis. A germline hotspot mutagenesis method was used, using PCR and phage display, as described in. Ho and Pastan, (2009) *Methods Mol Biol.* 525:293-30, incorporated by reference in its entirety herein. Briefly, the steps were as follows:

1—Sequence analysis of clone K3-1F4 was performed to determine germline hotspot(s). Germline hotspots were identified in the heavy chain CDR1 (HCDR1) and the light chain CDR3 (LCDR);

2—Overlap PCR was performed to randomize residues in HCDR1(FTS XXX GMH) and LCDR3 (WDD XXXX HWV) with the following oligonucleotides:

SfiI-VH-F
5'-cgcggcccagccggccatggcagagGTGCA-3'

VL-SfiI-R
5'-CCAGGCCCCCGAGGCCCAGGACGGTCAGCT-3'

HCDR1-NNK-R
5'-GACCCAATGCATGCCMNNMNNMNNGGAGGTGAAT-3'

HCDR1-F
5'-GGCATGCATTGGGTCCGCCA-3'

LCDR3-R
5'-GTCATCCCATGCTGCACAGT-3'

LCDR3-NNK-F
5'-GCAGCATGGGATGACnnknnknnknnkCATTGGGTGT-3'

3—The PCR product was digested with restriction enzyme Sfi I and ligated into the pCGMT3 vector;
4—The recombinant vector was ransformed into SS320 electroporation-competent *E. coli* cells;
5—The resulting library size was 6×10$^6$; and
6—Five (5) rounds of panning were performed.

Another library was made for affinity maturation, where some residues in the heavy chain CDR3 (HCDR3) were randomized with the following oligonucleotides:

```
HCDR3-R
5'-TGTCGCACAGTAATACACAGCCGTGTCCTC-3'
```

```
HCDR3-NNK-F
5'-TATTACTGTGCGACAnnknnknnknnknnkATGGACCTCT-3'
```

The resultant library size was 3×10⁷. From this library, 3 clones were identified: (1F4_5H1, 1F4_5E2 and 1F4_5F2) and their sequences provided in Table 3.

TABLE 3

|  | Heavy chain variable domain regions | Light chain variable domain regions |
|---|---|---|
| 1F4_1H2 | EVQLVQSGGGVVQPGRSLRLSCAAS<u>GFTS SLNGMH</u>WVRQAPGKGLEWVA<u>VISHDGSKK YYADSVKG</u>RFTISRDNSKNTLFVQLSSLR PEDTAVYYCAT<u>SLYSSMDL</u>WGQGTTVTVS S<br>SEQ ID NO. 21 | QSVVTQPPSVSAAPGQKVTISC<u>SGSNSNI GKNYVS</u>WFQQVPGTAPKLLIF<u>EDNQRPSG</u> IPDRFSASKSGTSASLAISGLQSEDEADY YC<u>AAWDDYGSTHWV</u>FGGGTKLTVL<br>SEQ ID NO. 22 |
| 1F4_1H2 | HC CDR1<br>GFTSSLNGMH<br>SEQ ID NO. 135<br>HC CDR2<br>VISHDGSKKYYADSVKG<br>SEQ ID NO. 136<br>HC CDR3<br>SLYSSMDL<br>SEQ ID NO. 137 | LC CDR1<br>SGSNSNIGKNYVS<br>SEQ ID NO. 138<br>LC CDR2<br>EDNQRPS<br>SEQ ID NO. 139<br>LC CDR3<br>AAWDDYGSTHWV<br>SEQ ID NO. 140 |
| 1F4_1C3 | EVQLVQSGGGVVQPGRSLRLSCAAS<u>GFTS RQYGMH</u>WVRQAPGKGLEWVA<u>VISHDGSKK YYADSVKG</u>RFTISRDNSKNTLFVQLSSLR PEDTAVYYCAT<u>SLYSSMDL</u>WGQGTTVTVS S<br>SEQ ID NO. 23 | QSVVTQPPSVSAAPGQKVTISC<u>SGSNSNI GKNYVS</u>WFQQVPGTAPKLLIF<u>EDNQRPS</u> IPDRFSASKSGTSASLAISGLQSEDEADY YC<u>AAWDDGRKVHWV</u>FGGGTKLTVL<br>SEQ ID NO. 24 |
| 1F4_1C3 | HC CDR1<br>GFTSRQYGMH<br>SEQ ID NO. 141<br>HC CDR2<br>VISHDGSKKYYADSVKG<br>SEQ ID NO. 142<br>HC CDR3<br>SLYSSMDL<br>SEQ ID NO. 143 | LC CDR1<br>SGSNSNIGKNYVS<br>SEQ ID NO. 144<br>LC CDR2<br>EDNQRPS<br>SEQ ID NO. 145<br>LC CDR3<br>AAWDDGRKVHWV<br>SEQ ID NO. 146 |
| 1F4_1D3 | EVQLVQSGGGVVQPGRSLRLSCAAS<u>GFTS STYGMH</u>WVRQAPGKGLEWVA<u>VISHDGSKK YYADSVKG</u>RFTISRDNSKNTLFVQLSSLR PEDTAVYYCAT<u>SLYSSMDL</u>WGQGTTVTVS S<br>SEQ ID NO. 25 | QSVVTQPPSVSAAPGQKVTISC<u>SGSNSNI GKNYVS</u>WFQQVPGTAPKLLIF<u>EDNQRPSG</u> IPDRFSASKSGTSASLAISGLQSEDEADY YC<u>AAWDDSRTTHWV</u>FGGGTKLTVL<br>SEQ ID NO. 26 |
| 1F4_1D3 | HC CDR1<br>GFTSSTYGMH<br>SEQ ID NO. 147<br>HC CDR2<br>VISHDGSKKYYADSVKG<br>SEQ ID NO. 148<br>HC CDR3<br>SLYSSMDL<br>SEQ ID NO. 149 | LC CDR1<br>SGSNSNIGKNYVS<br>SEQ ID NO. 150<br>LC CDR2<br>EDNQRPS<br>SEQ ID NO. 151<br>LC CDR3<br>AAWDDSRTTHWV<br>SEQ ID NO. 152 |
| 1F4_1E6 | EVQLVQSGGGVVQPGRSLRLSCAAS<u>GFTS RPYGMH</u>WVRQAPGKGLEWVA<u>VISHDGSKK YYADSVKG</u>RFTISRDNSKNTLFVQLSSLR PEDTAVYYCAT<u>SLYSSMDL</u>WGQGTTVTVS S<br>SEQ ID NO. 27 | QSVVTQPPSVSAAPGQKVTISC<u>SGSNSNI GKNYVS</u>WFQQVPGTAPKLLIF<u>EDNQRPSG</u> IPDRFSASKSGTSASLAISGLQSEDEADY YC<u>AAWDDFHSEHWV</u>FGGGTKLTVL<br>SEQ ID NO. 28 |
| 1F4_1E6 | HC CDR1<br>GFTSRPYGMH<br>SEQ ID NO. 153<br>HC CDR2<br>VISHDGSKKYYADSVKG<br>SEQ ID NO. 154<br>HC CDR3<br>SLYSSMDL<br>SEQ ID NO. 155 | LC CDR1<br>SGSNSNIGKNYVS<br>SEQ ID NO. 156<br>LC CDR2<br>EDNQRPS<br>SEQ ID NO. 157<br>LC CDR3<br>AAWDDFHSEHWV<br>SEQ ID NO. 158 |

TABLE 3-continued

| | Heavy chain variable domain regions | Light chain variable domain regions |
|---|---|---|
| 1F4_1F6 | EVQLVQSGGGVVQPGRSLRLSCAAS<u>GFTSATYGMH</u>WVRQAPGKGLEWVA<u>VISHDGSKKYYADSVKG</u>RFTISRDNSKNTLFVQLSSLRPEDTAVYYCAT<u>SLYSSMDL</u>WGQGTTVTVSS<br>SEQ ID NO. 29 | QSVVTQPPSVSAAPGQKVTISC<u>SGSNSNIGKNYVS</u>WFQQVPGTAPKLLIF<u>EDNQRPS</u>GIPDRFSASKSGTSASLAISGLQSEDEADYYC<u>AAWDDSSDTHWV</u>FGGGTKLTVL<br>SEQ ID NO. 30 |
| 1F4_1F6 | HC CDR1<br>GFTSATYGMH<br>SEQ ID NO. 159<br>HC CDR2<br>VISHDGSKKYYADSVKG<br>SEQ ID NO. 160<br>HC CDR3<br>SLYSSMDL<br>SEQ ID NO. 161 | LC CDR1<br>SGSNSNIGKNYVS<br>SEQ ID NO. 162<br>LC CDR2<br>EDNQRPS<br>SEQ ID NO. 163<br>LC CDR3<br>AAWDDSSDTHWV<br>SEQ ID NO. 164 |
| 1F4_1G6 | EVQLVQSGGGVVQPGRSLRLSCAAS<u>GFTSSFHGMH</u>WVRQAPGKGLEWVA<u>VISHDGSKKYYADSVKG</u>RFTISRDNSKNTLFVQLSSLRPEDTAVYYCAT<u>SLYSSMDL</u>WGQGTTVTVSS<br>SEQ ID NO. 31 | QSVVTQPPSVSAAPGQKVTISC<u>SGSNSNIGKNYVS</u>WFQQVPGTAPKLLIF<u>EDNQRPS</u>GIPDRFSASKSGTSASLAISGLQSEDEADYYC<u>AAWDDSGDVHWV</u>FGGGTKLTVL<br>SEQ ID NO. 32 |
| 1F4_1G6 | HC CDR1<br>GFTSSFHGMH<br>SEQ ID NO. 165<br>HC CDR2<br>VISHDGSKKYYADSVKG<br>SEQ ID NO. 166<br>HC CDR3<br>SLYSSMDL<br>SEQ ID NO. 167 | LC CDR1<br>SGSNSNIGKNYVS<br>SEQ ID NO. 168<br>LC CDR2<br>EDNQRPS<br>SEQ ID NO. 169<br>LC CDR3<br>AAWDDSGDVHWV<br>SEQ ID NO. 170 |
| 1F4_1E3 | EVQLVQSGGGVVQPGRSLRLSCAAS<u>GFTSRHPGMH</u>WVRQAPGKGLEWVA<u>VISHDGSKKYYADSVKG</u>RFTISRDNSKNTLFVQLSSLRPEDTAVYYCAT<u>SLYSSMDL</u>WGQGTTVTVSS<br>SEQ ID NO. 33 | QSVVTQPPSVSAAPGQKVTISC<u>SGSNSNIGKNYVS</u>WFQQVPGTAPKLLIF<u>EDNQRPS</u>GIPDRFSASKSGTSASLAISGLQSEDEADYYC<u>AAWDDYRGPHWV</u>FGGGTKLTVL<br>SEQ ID NO. 34 |
| 1F4_1E3 | HC CDR1<br>GFTSRHPGMH<br>SEQ ID NO. 171<br>HC CDR2<br>VISHDGSKKYYADSVKG<br>SEQ ID NO. 172<br>HC CDR3<br>SLYSSMDL<br>SEQ ID NO. 173 | LC CDR1<br>SGSNSNIGKNYVS<br>SEQ ID NO. 174<br>LC CDR2<br>EDNQRPS<br>SEQ ID NO. 175<br>LC CDR3<br>AAWDDYRGPHWV<br>SEQ ID NO. 176 |
| 1F4_3D11 | EVQLVQSGGGVVQPGRSLRLSCAAS<u>GFTSRHPGMH</u>WVRQAPGKGLEWVA<u>VISHDGSKKYYADSVKG</u>RFTISRDNSKNTLFVQLSSLRPEDTAVYYCAT<u>SLYSSMDL</u>WGQGTTVTVSS<br>SEQ ID NO. 35 | QSVVTQPPSVSAAPGQKVTISC<u>SGSNSNIGKNYVS</u>WFQQVPGTAPKLLIF<u>EDNQRPS</u>GIPDRFSASKSGTSASLAISGLQSEDEADYYC<u>AAWDDYRGPHWV</u>FGGGTKLTVL<br>SEQ ID NO. 36 |
| 1F4_3D11 | HC CDR1<br>GFTSRHPGMH<br>SEQ ID NO. 177<br>HC CDR2<br>VISHDGSKKYYADSVKG<br>SEQ ID NO. 178<br>HC CDR3<br>SLYSSMDL<br>SEQ ID NO. 179 | LC CDR1<br>SGSNSNIGKNYVS<br>SEQ ID NO. 180<br>LC CDR2<br>EDNQRPS<br>SEQ ID NO. 181<br>LC CDR3<br>AAWDDYRGPHWV<br>SEQ ID NO. 182 |
| 1F4_4E10 | EVQLVQSGGGVVQPGRSLRLSCAAS<u>GFTSRAPGMH</u>WVRQAPGKGLEWVA<u>VISHDGSKKYYADSVKG</u>RFTISRDNSKNTLFVQLSSLRPEDTAVYYCAT<u>SLYSSMDL</u>WGQGTTVTVSS<br>SEQ ID NO. 37 | QSVVTQPPSVSAAPGQKVTISC<u>SGSNSNIGKNYVS</u>WFQQVPGTAPKLLIF<u>EDNQRPS</u>GIPDRFSASKSGTSASLAISGLQSEDEADYYC<u>AAWDDHNGEHWV</u>FGGGTKLTVL<br>SEQ ID NO. 38 |

TABLE 3-continued

|  | Heavy chain variable domain regions | Light chain variable domain regions |
|---|---|---|
| 1F4_4E10 | HC CDR1<br>GFTSRAPGMH<br>SEQ ID NO. 183<br>HC CDR2<br>VISHDGSKKYYADSVKG<br>SEQ ID NO. 184<br>HC CDR3<br>SLYSSMDL<br>SEQ ID NO. 185 | LC CDR1<br>SGSNSNIGKNYVS<br>SEQ ID NO. 186<br>LC CDR2<br>EDNQRPS<br>SEQ ID NO. 187<br>LC CDR3<br>AAWDDHNGEHWV<br>SEQ ID NO. 188 |
| 1F4_4F10 | EVQLVQSGGGVVQPGRSLRLSCAAS<u>GFTS</u><br><u>RHPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 39 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDKFGVHWV</u>FGGGTKLTVL<br>SEQ ID NO. 40 |
| 1F4_4F10 | HC CDR1<br>GFTSRHPGMH<br>SEQ ID NO. 189<br>HC CDR2<br>VISHDGSKKYYADSVKG<br>SEQ ID NO. 190<br>HC CDR3<br>SLYSSMDL<br>SEQ ID NO. 191 | LC CDR1<br>SGSNSNIGKNYVS<br>SEQ ID NO. 192<br>LC CDR2<br>EDNQRPS<br>SEQ ID NO. 193<br>LC CDR3<br>AAWDDKFGVHWV<br>SEQ ID NO. 194 |
| 1F4_4A12 | EVQLVQSGGGVVQPGRSLRLSCAAS<u>GFTS</u><br><u>RKYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 41 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSPTIHWV</u>FGGGTKLTVL<br>SEQ ID NO. 42 |
| 1F4_4A12 | HC CDR1<br>GFTSRKYGMH<br>SEQ ID NO. 195<br>HC CDR2<br>VISHDGSKKYYADSVKG<br>SEQ ID NO. 196<br>HC CDR3<br>SLYSSMDL<br>SEQ ID NO. 197 | LC CDR1<br>SGSNSNIGKNYVS<br>SEQ ID NO. 198<br>LC CDR2<br>EDNQRPS<br>SEQ ID NO. 199<br>LC CDR3<br>AAWDDSPTIHWV<br>SEQ ID NO. 200 |
| 1F4_4D12 | EVQLVQSGGGVVQPGRSLRLSCAAS<u>GFTS</u><br><u>HNKGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 43 | QSVVTQPPSVSAAPGQKVTISCSGSNFNI<br>GKNYVSWFQQVPGTAPKLLIF<u>EDNQRPSG</u><br>IPDRFSASKSGTSASLAISGLQSEDEADY<br>YC<u>AAWDDFAGVHWV</u>FGGGTKLTVL<br>SEQ ID NO. 44 |
| 1F4_4D12 | HC CDR1<br>GFTSHNKGMH<br>SEQ ID NO. 201<br>HC CDR2<br>VISHDGSKKYYADSVKG<br>SEQ ID NO. 202<br>HC CDR3<br>SLYSSMDL<br>SEQ ID NO. 203 | LC CDR1<br>SGSNFNIGKNYVS<br>SEQ ID NO. 204<br>LC CDR2<br>EDNQRPS<br>SEQ ID NO. 205<br>LC CDR3<br>AAWDDFAGVHWV<br>SEQ ID NO.206 |
| 1F4_4E12 | EVQLVQSGGGVVQPGRSLRLSCAAS<u>GFTS</u><br><u>YKYGMH</u>WVRQAPGKGLEWVA<u>VISHDGSKK</u><br><u>YYADSVKG</u>RFTISRDNSKNTLFVQLSSLR<br>PEDTAVYYCAS<u>SLYSSMDL</u>WGQGTTVTVS<br>S<br>SEQ ID NO. 45 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSFSEHWV</u>FGGGTKLTVL<br>SEQ ID NO. 46 |
| 1F4_4E12 | HC CDR1<br>GFTSYKYGMH<br>SEQ ID NO. 207<br>HC CDR2<br>VISHDGSKKYYADSVKG<br>SEQ ID NO. 208<br>HC CDR3<br>SLYSSMDL<br>SEQ ID NO. 209 | LC CDR1<br>SGSNSNIGKNYVS<br>SEQ ID NO. 210<br>LC CDR2<br>EDNQRPS<br>SEQ ID NO. 211<br>LC CDR3<br>AAWDDSFSEHWV<br>SEQ ID NO. 212 |

TABLE 3-continued

| | Heavy chain variable domain regions | Light chain variable domain regions |
|---|---|---|
| 1F4_5C4 | EVQLVQSGGGVVQPGRSLRLSCAAS<u>GFTS</u><br><u>RAPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 47 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDQNGVHWV</u>FGGGTKLTVL<br>SEQ ID NO. 48 |
| 1F4_5C4 | HC CDR1<br>GFTSRAPGMH<br>SEQ ID NO. 213<br>HC CDR2<br>VISHDGSKKYYADSVKG<br>SEQ ID NO. 214<br>HC CDR3<br>SLYSSMDL<br>SEQ ID NO. 215 | LC CDR1<br>SGSNSNIGKNYVS<br>SEQ ID NO. 216<br>LC CDR2<br>EDNQRPS<br>SEQ ID NO. 217<br>LC CDR3<br>AAWDDQNGVHWV<br>SEQ ID NO. 218 |
| 1F4_5A4 | EVQLVQSGGGVVQPGRSLRLSCAAS<u>GFTS</u><br><u>RSPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 49 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDLRGVHWV</u>FGGGTKLTVL<br>SEQ ID NO. 50 |
| 1F4_5A4 | HC CDR1<br>GFTSRSPGMH<br>SEQ ID NO. 219<br>HC CDR2<br>VISHDGSKKYYADSVKG<br>SEQ ID NO. 220<br>HC CDR3<br>SLYSSMDL<br>SEQ ID NO. 221 | LC CDR1<br>SGSNSNIGKNYVS<br>SEQ ID NO. 222<br>LC CDR2<br>EDNQRPS<br>SEQ ID NO. 223<br>LC CDR3<br>AAWDDLRGVHWV<br>SEQ ID NO. 224 |
| 1F4_5B7 | EVQLVQSGGGVVQPGRSLRLSCAAS<u>GFTS</u><br><u>RHHGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 51 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDRHGTHWV</u>FGGGTKLTVL<br>SEQ ID NO. 52 |
| 1F4_5B7 | HC CDR1<br>GFTSRHHGMH<br>SEQ ID NO. 225<br>HC CDR2<br>VISHDGSKKYYADSVKG<br>SEQ ID NO. 226<br>HC CDR3<br>SLYSSMDL<br>SEQ ID NO.227 | LC CDR1<br>SGSNSNIGKNYVS<br>SEQ ID NO. 228<br>LC CDR2<br>EDNQRPS<br>SEQ ID NO. 229<br>LC CDR3<br>AAWDDRHGTHWV<br>SEQ ID NO. 230 |
| 1F4_5F8 | EVQLVQSGGGVVQPGRSLRLSCAAS<u>GFTS</u><br><u>RNPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 53 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSTGVHWV</u>FGGGTKLTVL<br>SEQ ID NO. 54 |
| 1F4_5F8 | HC CDR1<br>GFTSRNPGMH<br>SEQ ID NO. 231<br>HC CDR2<br>VISHDGSKKYYADSVKG<br>SEQ ID NO. 232<br>HC CDR3<br>SLYSSMDL<br>SEQ ID NO. 233 | LC CDR1<br>SGSNSNIGKNYVS<br>SEQ ID NO. 234<br>LC CDR2<br>EDNQRPS<br>SEQ ID NO. 235<br>LC CDR3<br>AAWDDSTGVHWV<br>SEQ ID NO. 236 |
| 1F4_5D3 | EVQLVQSGGGVVQPGRSLRLSCAAS<u>GFTS</u><br><u>RTYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 55 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDLPTDHWV</u>FGGGTKLTVL<br>SEQ ID NO. 56 |

TABLE 3-continued

|   | Heavy chain variable domain regions | Light chain variable domain regions |
|---|---|---|
| 1F4_5D3 | HC CDR1<br>GFTSRTYGMH<br>SEQ ID NO. 237<br>HC CDR2<br>VISHDGSKKYYADSVKG<br>SEQ ID NO. 238<br>HC CDR3<br>SLYSSMDL<br>SEQ ID NO. 239 | LC CDR1<br>SGSNSNIGKNYVS<br>SEQ ID NO. 240<br>LC CDR2<br>EDNQRPS<br>SEQ ID NO. 241<br>LC CDR3<br>AAWDDLPTDHWV<br>SEQ ID NO. 242 |
| 1F4_5G5 | EVQLVQSGGGVVQPGRSLRLSCAASGFTS<br>RQYGMHWVRQAPGKGLEWVAVISHDGSKK<br>YYADSVKGRFTISRDNSKNTLFVQLSSLR<br>PEDTAVYYCATSLYSSMDLWGQGTTVTVS<br>S<br>SEQ ID NO. 57 | QSVVTQPPSVSAAPGQKVTISCSGSNSNI<br>GKNYVSWFQQVPGTAPKLLIFEDNQRPSG<br>IPDRFSASKSGTSASLAISGLQSEDEADY<br>YCAAWDDYSGVHWVFGGGTKLTVL<br>SEQ ID NO. 58 |
| 1F4_5G5 | HC CDR1<br>GFTSRQYGMH<br>SEQ ID NO. 243<br>HC CDR2<br>VISHDGSKKYYADSVKG<br>SEQ ID NO. 244<br>HC CDR3<br>SLYSSMDL<br>SEQ ID NO. 245 | LC CDR1<br>SGSNSNIGKNYVS<br>SEQ ID NO. 246<br>LC CDR2<br>EDNQRPS<br>SEQ ID NO. 247<br>LC CDR3<br>AAWDDYSGVHWV<br>SEQ ID NO. 248 |
| 1F4_5A10 | EVQLVQSGGGVVQPGRSLRLSCAASGFTS<br>SPYGMHWVRQAPGKGLEWVAVISHDGSKK<br>YYADSVKGRFTISRDNSKNTLFVQLSSLR<br>PEDTAVYYCATSLYSSMDLWGQGTTVTVS<br>S<br>SEQ ID NO. 59 | QSVVTQPPSVSAAPGQKVTISCSGSNSNI<br>GKNYVSWFQQVPGTAPKLLIFEDNQRPSG<br>IPDRFSASKSGTSASLAISGLQSEDEADY<br>YCAAWDDNPRDHWVFGGGTKLTVL<br>SEQ ID NO. 60 |
| 1F4_5A10 | HC CDR1<br>GFTSSPYGMH<br>SEQ ID NO. 249<br>HC CDR2<br>VISHDGSKKYYADSVKG<br>SEQ ID NO. 250<br>HC CDR3<br>SLYSSMDL<br>SEQ ID NO. 251 | LC CDR1<br>SGSNSNIGKNYVS<br>SEQ ID NO. 252<br>LC CDR2<br>EDNQRPS<br>SEQ ID NO. 253<br>LC CDR3<br>AAWDDNPRDHWV<br>SEQ ID NO. 254 |
| 1F4_5B12 | EVQLVQSGGGVVQPGRSLRLSCAASGFTS<br>SKPGMHWVRQAPGKGLEWVAVISHDGSKK<br>YYADSVKGRFTISRDNSKNTLFVQLSSLR<br>PEDTAVYYCATSLYSSMDLWGQGTTVTVS<br>S<br>SEQ ID NO. 61 | QSVVTQPPSVSAAPGQKVTISCSGSNSNI<br>GKNYVSWFQQVPGTAPKLLIFEDNQRPSG<br>IPDRFSASKSGTSASLAISGLQSEDEADY<br>YCAAWDDLRGVHWVFGGGTKLTVL<br>SEQ ID NO. 62 |
| 1F4_5B12 | HC CDR1<br>GFTSSKPGMH<br>SEQ ID NO. 255<br>HC CDR2<br>VISHDGSKKYYADSVKG<br>SEQ ID NO. 256<br>HC CDR3<br>SLYSSMDL<br>SEQ ID NO. 257 | LC CDR1<br>SGSNSNIGKNYVS<br>SEQ ID NO. 258<br>LC CDR2<br>EDNQRPS<br>SEQ ID NO. 259<br>LC CDR3<br>AAWDDLRGVHWV<br>SEQ ID NO. 260 |
| 1F4_5C5 | EVQLVQSGGGVVQPGRSLRLSCAASGFTS<br>KKYGMHWVRQAPGKGLEWVAVISHDGSKK<br>YYADSVKGRFTISRDNSKNTLFVQLSSLR<br>PEDTAVYYCATSLYSSMDLWGQGTTVTVS<br>S<br>SEQ ID NO. 63 | QSVVTQPPSVSAAPGQKVTISCSGSNSNI<br>GKNYVSWFQQVPGTAPKLLIFEDNQRPSG<br>IPDRFSASKSGTSASLAISGLQSEDEADY<br>YCAAWDDLGGDHWVFGGGTKLTVL<br>SEQ ID NO. 64 |
| 1F4_5C5 | HC CDR1<br>GFTSKKYGMH<br>SEQ ID NO. 261<br>HC CDR2<br>VISHDGSKKYYADSVKG<br>SEQ ID NO. 262<br>HC CDR3<br>SLYSSMDL<br>SEQ ID NO. 263 | LC CDR1<br>SGSNSNIGKNYVS<br>SEQ ID NO. 264<br>LC CDR2<br>EDNQRPS<br>SEQ ID NO. 265<br>LC CDR3<br>AAWDDLGGDHWV<br>SEQ ID NO. 266 |

TABLE 3-continued

| | Heavy chain variable domain regions | Light chain variable domain regions |
|---|---|---|
| 1F4_5F6 | EVQLVQSGGGVVQPGRSLRLSCAAS<u>GFTS</u><br><u>TLPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 65 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSAGVHWV</u>FGGGTKLTVL<br>SEQ ID NO. 66 |
| 1F4_5F6 | HC CDR1<br>GFTSTLPGMH<br>SEQ ID NO. 267<br>HC CDR2<br>VISHDGSKKYYADSVKG<br>SEQ ID NO. 268<br>HC CDR3<br>SLYSSMDL<br>SEQ ID NO. 269 | LC CDR1<br>SGSNSNIGKNYVS<br>SEQ ID NO. 270<br>LC CDR2<br>EDNQRPS<br>SEQ ID NO. 271<br>LC CDR3<br>AAWDDSAGVHWV<br>SEQ ID NO. 272 |
| 1F4_5H4 | EVQLVQSGGGVVQPGRSLRLSCAAS<u>GFTS</u><br><u>KMPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 67 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDEHGVHWV</u>FGGGTKLTVL<br>SEQ ID NO. 68 |
| 1F4_5H4 | HC CDR1<br>GFTSKMPGMH<br>SEQ ID NO. 273<br>HC CDR2<br>VISHDGSKKYYADSVKG<br>SEQ ID NO. 274<br>HC CDR3<br>SLYSSMDL<br>SEQ ID NO. 275 | LC CDR1<br>SGSNSNIGKNYVS<br>SEQ ID NO. 276<br>LC CDR2<br>EDNQRPS<br>SEQ ID NO. 277<br>LC CDR3<br>AAWDDEHGVHWV<br>SEQ ID NO. 278 |
| 1F4_5H1 | EVQLVQSGGGVVQPGRSLRLSCAAS<u>GFTS</u><br><u>SNYGMH</u>WVRQAPGKGLEWVA<u>VISHDGSKK</u><br><u>YYADSVKG</u>RFTISRDNSKNTLFVQLSSLR<br>PEDTAVYYCAA<u>SLYSSMDL</u>WGQGTTVTVS<br>S<br>SEQ ID NO. 69 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSLSAHWV</u>FGGGTKLTVL<br>SEQ ID NO. 70 |
| 1F4_5H1 | HC CDR1<br>GFTSSNYGMH<br>SEQ ID NO. 279<br>HC CDR2<br>VISHDGSKKYYADSVKG<br>SEQ ID NO. 280<br>HC CDR3<br>SLYSSMDL<br>SEQ ID NO. 281 | LC CDR1<br>SGSNSNIGKNYVS<br>SEQ ID NO. 282<br>LC CDR2<br>EDNQRPS<br>SEQ ID NO. 283<br>LC CDR3<br>AAWDDSLSAHWV<br>SEQ ID NO. 284 |
| 1F4_5E2 | EVQLVQSGGGVVQPGRSLRLSCAAS<u>GFTS</u><br><u>SNYGMH</u>WVRQAPGKGLEWVA<u>VISHDGSKK</u><br><u>YYADSVKG</u>RFTISRDNSKNTLFVQLSSLR<br>PEDTAVYYCATSMVSSMDLWGQGTTVTVS<br>S<br>SEQ ID NO. 71 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSLSTHWV</u>FGGGTKLTVL<br>SEQ ID NO. 72 |
| 1F4_5E2 | HC CDR1<br>GFTSSNYGMH<br>SEQ ID NO. 285<br>HC CDR2<br>VISHDGSKKYYADSVKG<br>SEQ ID NO. 286<br>HC CDR3<br>SMVSSMDL<br>SEQ ID NO. 287 | LC CDR1<br>SGSNSNIGKNYVS<br>SEQ ID NO. 288<br>LC CDR2<br>EDNQRPS<br>SEQ ID NO. 289<br>LC CDR3<br>AAWDDSLSTHWV<br>SEQ ID NO. 290 |
| 1F4_5F2 | EVQLVQSGGGVVQPGRSLRLSCAAS<u>GFTS</u><br><u>SNYGMH</u>WVRQAPGKGLEWVA<u>VISHDGSKK</u><br><u>YYADSVKG</u>RFTISRDNSKNTLFVQLSSLR<br>PEDTAVYYCATSMRSSMDLWGQGTTVTVS<br>S<br>SEQ ID NO. 73 | QSVVTQPPSVSAAPGQKVTISC<u>SGSNSNI</u><br><u>SNYGMH</u>WFQQVPGTAPKLLIF<u>EDNQRPSG</u><br>IPDRFSASKSGTSASLAISGLQSEDEADY<br>YC<u>AAWDDSLSAHWV</u>FGGGTKLTVL<br>SEQ ID NO. 74 |

TABLE 3-continued

| | Heavy chain variable domain regions | Light chain variable domain regions |
|---|---|---|
| 1F4 5F2 | HC CDR1<br>GFTSSNYGMH<br>SEQ ID NO. 291<br>HC CDR2<br>VISHDGSKKYYADSVKG<br>SEQ ID NO. 292<br>HC CDR3<br>SMRSSMDL<br>SEQ ID NO. 293 | LC CDR1<br>SGSNSNIGKNYVS<br>SEQ ID NO. 294<br>LC CDR2<br>EDNQRPS<br>SEQ ID NO. 295<br>LC CDR3<br>AAWDDSLSAHWV<br>SEQ ID NO. 296 |
| LN-97S | EVQLVQSGGGVVQPGRSLRLSCAAS<u>GFTS</u><br><u>SNYGMH</u>WVRQAPGKGLEWVA<u>VISHDGSKK</u><br><u>YYADSVK</u>GRFTISRDNSKNTLFVQLSSLR<br>PEDTAVYYCAT<u>SLYSSMDL</u>WGQGTTVTVS<br>S<br>SEQ ID NO. 297 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSLSAHWV</u>FGGGTKLTVL<br><br>SEQ ID NO. 298 |
| LN-97S | HC CDR1<br>GFTSSNYGMH<br>SEQ ID NO. 299<br>HC CDR2<br>VISHDGSKKYYADSVKG<br>SEQ ID NO. 300<br>HC CDR3<br>SLYSSMDL<br>SEQ ID NO. 301 | LC CDR1<br>SGSNSNIGKNYVS<br>SEQ ID NO. 302<br>LC CDR2<br>EDNQRPS<br>SEQ ID NO. 303<br>LC CDR3<br>AAWDDSLSAHWV<br>SEQ ID NO. 304 |

Example 3. Specificity of Anti-KRAS Antibodies to Cellular Targets

Specificity of the anti-KRAS antibodies described in Tables 2 and 3 were tested for their specificity to human cells expressing wild type KRAS or mutant versions of KRAS associated with cancer. Specifically, binding of human anti-KRAS antibodies 1E3, 4F10, and LN97S to cellular targets in KRAS G12D over-expressing pancreatic tumor cells (ASPC-1), U2OS human osteosarcoma cells (KRAS wild-type), and A549 human lung adenocarcinoma epithelial cells (KRASG12S expressing cells) was tested. The G12S mutation results in an amino acid substitution at position 12 in KRAS, from a glycine (G) to a serine (S). The G12 D mutation results in in an amino acid substitution at position 12 in KRAS, from a glycine (G) to an aspartic acid (D).

Binding of anti-KRAS antibodies to cellular human KRAS proteins was measured by high content screening (HCS) microscopic assay. Briefly, cells were seeded in complete media (10% FBS DMEM, F12-K, RPMI, DMEM respectively) overnight in a black-walled 96-well plate. The next day, the antibody clones were added to the permeabilized cells and incubated overnight. Goat anti-Human IgG conjugated to Alexa488 (green fluorophore) was then added to the wells. Green signals were visualized by HCS confocal microscopy, then the cumulative mean fluorescence intensity was analyzed by ImageXpress software.

The results of the study are shown in FIG. 1, where binding of the antibody is shown as fold change relative to wild type. Anti-KRAS antibodies 1E3, 4F10 and LN97S showed enhanced binding to cellular proteins in KRAS G12D-overexpressing pancreatic tumor cells. LN97S also showed enhanced binding to KRAS G12S-overexpressing cells.

Example 4. Selection of Anti-KRAS G12D Antibody 4F10

In vitro affinity maturation of antibody 1F4 was carried out to increase antibody affinity to antigen and functional activity, as described in Example 2. Antibody 1F4 is specific for KRAS G12D. After screening for antibodies that showed improved binding affinity to recombinant proteins as well as cellular targets compared to parental antibody clone 1F4, anti-KRAS G12D antibody 4F10 was selected for further functionality evaluation. The additional experiments are described below in Examples 5-9, including anti-KRAS G12D antibody or KRAS G12D iTAbs comprising the 4F10 antibody. In the below examples, as controls fully human IgGs specific for bacterial proteins were produced and modified with the same procedure as KRAS iTAbs, then included as experimental control iTAbs. The sequences of antibody 4F10 are provided in SEQ ID Nos: 15 (heavy chain variable region), 16 (light chain variable region), 117-119 (CDRs of heavy chain variable region), and 120-122 (CDRs of light chain variable region).

Example 5. Anti-KRAS G12D Antibody Binding Activity to KRAS Proteins

The binding of anti-KRAS G12D antibody 4F10 to KRAS wild type and mutant proteins was determined using ELISA. An anti-h-Fc-HRP antibody was used as a control. Briefly, diluted anti-KRAS G12D clone 4F10 antibodies were incubated in a plate coated with recombinant human KRAS proteins. After incubation, a goat anti-human IgG Fc mAb conjugated to horse radish peroxidase (HRP) (secondary antibody) was added and bound to the Fc region of anti-KRAS mAbs. The Fc bound secondary antibodies were detected by addition of chromogen substrate. The color intensity developed was proportional to the amount of anti-KRAS antibody in the sample. A summary of the binding characteristics of 4F10 is provided in FIG. 3A, which provides results showing that antibody 4F10 preferentially bound to the mutant form of KRAS G12D and showed little to no binding to wild type or KRAS G12C.

HCS confocal microscopy was also used to measure 4F10 antibody binding to cellular proteins. Cells were seeded onto a collagen-coated 96-well plate overnight. The next day, cells were fixed, permeabilized, and blocked with ImagIT Image Enhancer for 30 minutes. Cells were stained with anti-KRAS antibodies overnight at 4° C. Cells were washed and incubated with anti-Human Alexa 488 and imaged using HCS confocal microscope. U2OS are osteosarcoma cells expressing wild-type KRAS. A549 are human lung cancer cells with KRAS G12S. ASPC-1 are human pancreatic cancer cells with KRAS G12D mutation. The results are described in FIG. 3B.

Figure 3A:
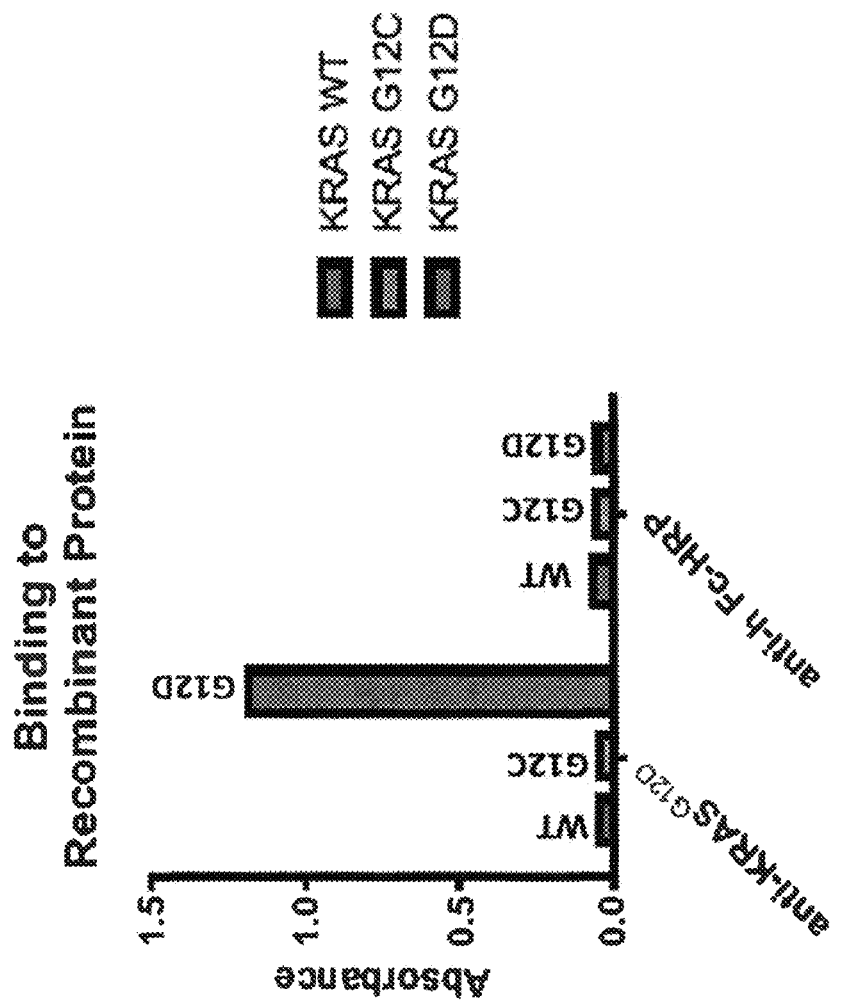
FIG. 3A is a graph that shows the results of a direct ELISA using recombinant KRAS wild type and mutant proteins (wild type, mutant KRAS G12C, and mutant KRAS G12D). The results provided in FIG. 3A show that anti-KRAS G12D antibody 4F10 is specific for KRAS G12D. Anti-human IgG-Fc-HRP was used as a control.
Figure 3B:
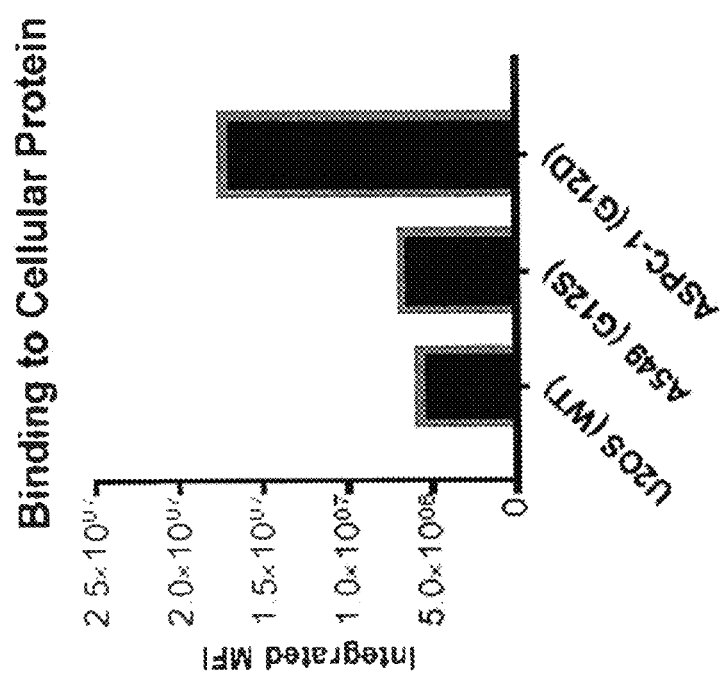
FIG. 3B is a graph that shows the results of high content screening (HCS) confocal microscopy to measure antibody binding to cellular proteins. U2OS are osteosarcoma cells expressing wild-type KRAS. A549 are human lung cancer cells expressing KRAS G12S. ASPC-1 are human pancreatic cancer cells with KRAS G12D mutation.

The results from FIG. 3A and FIG. 3B show that the anti-KRAS G12D 4F10 antibody binds selectively to KRAS G12D mutant proteins.

Example 6. Binding Activity of KRAS G12D 4F10 Antibody Conjugate

Figure 4:
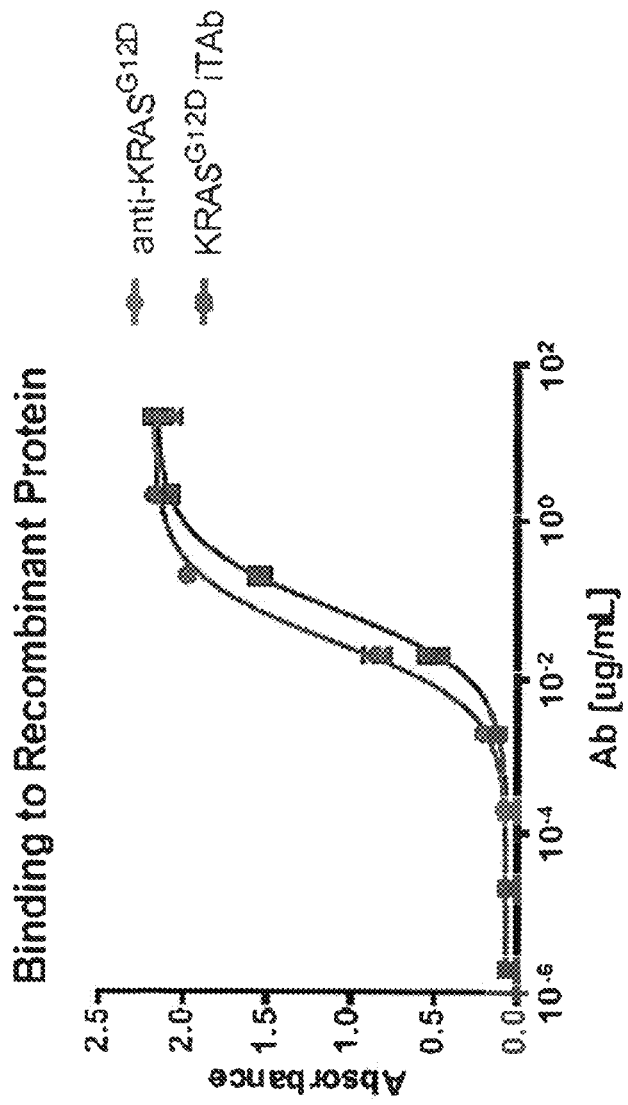
FIG. 4 is a graph that shows the results of an ELISA assay that compared the binding activity of an anti-KRAS G12D antibody 4F10 conjugate ($KRAS^{G12D}$ iTAb (Compound 1)) and an anti-KRAS G12D 4F10 monoclonal antibody (anti-$KRAS^{G12D}$). Antibody and antibody conjugate concentration is shown on the x-axis and absorbance is on the y-axis.

The binding activity of an anti-KRAS G12D 4F10 antibody conjugate (Compound 1) was examined Conjugated 4F10 was made according to the methods described herein. Briefly, diluted anti-KRAS G12D 4F10 antibody or conjugated 4F10 antibody (KRAS G12D iTAb (Compound 1)) were each incubated in a plate coated with recombinant human KRAS proteins. After incubation, goat anti-human IgG Fc mAb conjugated to horse radish peroxidase (HRP) (secondary antibody) was added and bound to the Fc region of anti-KRAS mAbs. The Fc bound secondary antibodies were detected by the addition of chromogen substrate. The color intensity developed was proportional to the amount of anti-KRAS mAb in the sample. FIG. 4 shows the results of these experiments, comparing the binding activity of the unconjugated anti-KRAS G12D 4F10 antibody and the anti-KRAS G12D 4F10 antibody conjugate (Compound 1) by ELISA. As shown in FIG. 4, modification (i.e., conjugation) of the anti-KRAS 4F10 antibody did not substantially affect the binding activity between the antibody and its antigen.

Example 7. KRAS G12D Antibody Conjugate Accumulation within Tumor Cells

Experiments were performed to examine the accumulation of the KRAS G12D 4F10 antibody conjugate (Compound 1) in tumor cells. Briefly, ASPC-1 human pancreatic tumor cells, which are positive for KRAS G12D, were incubated with the KRAS G12D clone 4F10 antibody conjugate (Compound 1). Nuclei were visualized by blue fluorescence, cell membrane was visualized by green fluorescence, and the antibody was visualized by red fluorescence. The KRAS G12D 4F10 antibody conjugate (Compound 1) was able to internalize into KRAS G12D expressing cancer cells (ASPC-1), seen by red colored antibodies inside the identifiable cell boundaries stained with WGA (wheat germ agglutinin; green) (data not shown).

Figure 5A:
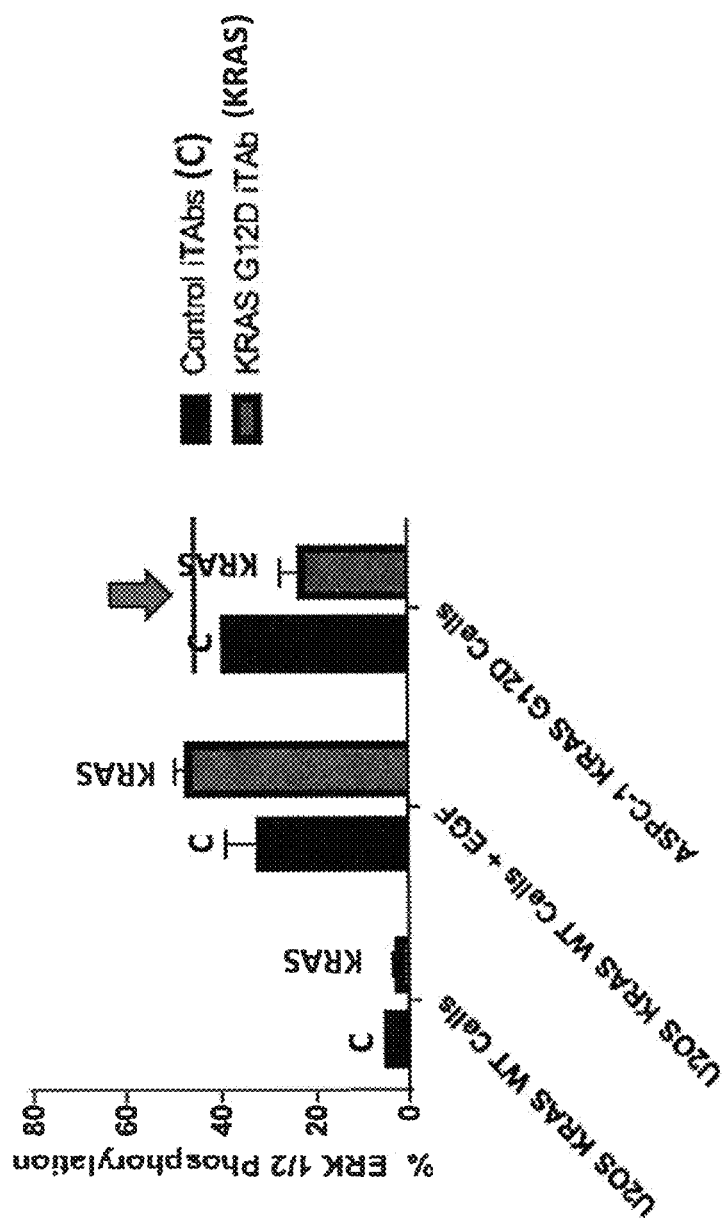
FIG. 5A is a graph that shows the level of ERK 1/2 phosphorylation in U2OS KRAS wild type cells, in U2OS KRAS wild type cells stimulated with EGF, and in ASPC-1 cells with a KRAS G12D mutation after treatment with a control antibody conjugate (Control iTAbs) or treatment with anti-KRAS G12D 4F10 antibody conjugate (KRAS G12D iTAb (Compound 1)). Fully human IgGs against bacterial proteins were produced and modified with the same procedure as the anti-KRAS G12D antibody conjugates, then included as experimental control antibody conjugates.
Figure 5B:
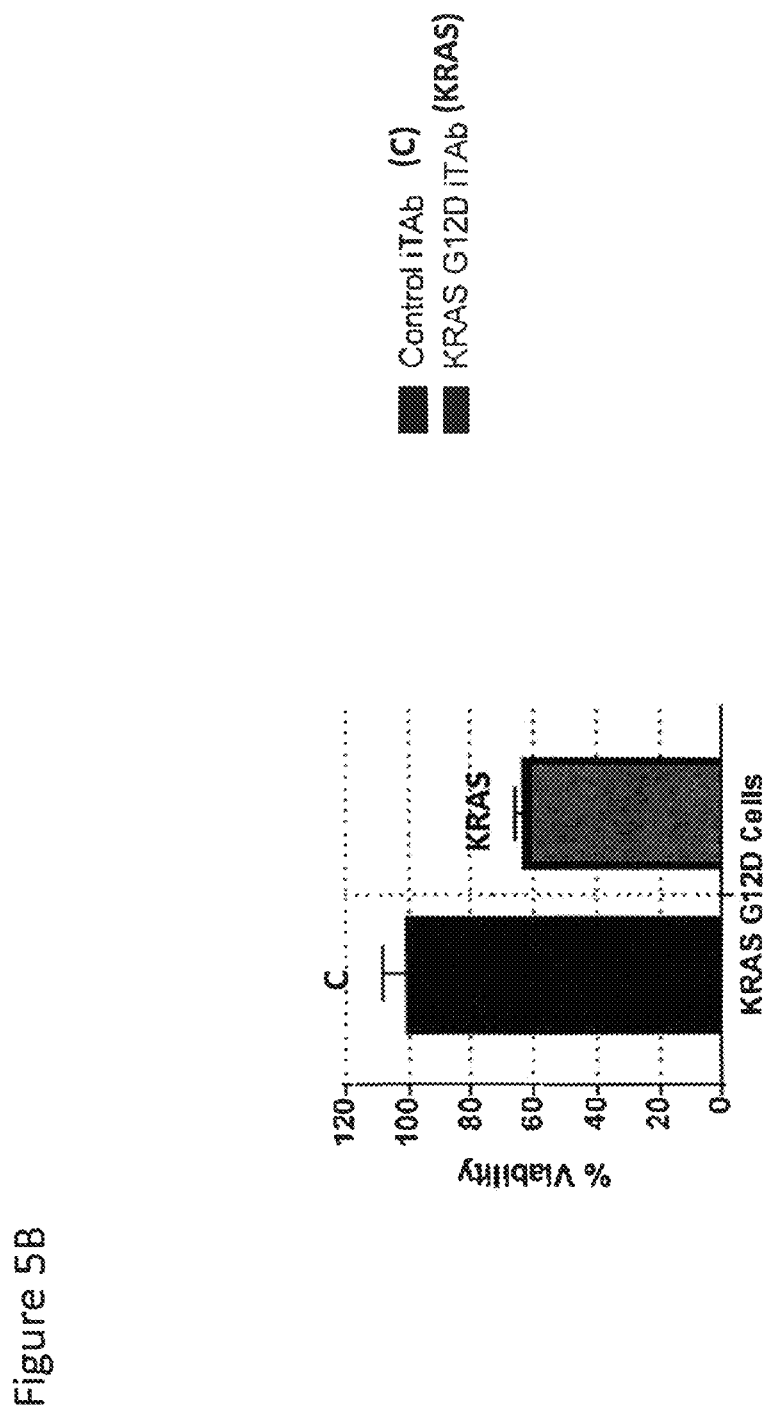
FIG. 5B is a graph that shows the percent viability of the KRAS G12D cells after treatment with a control antibody conjugate (Control iTAbs) or treatment with an anti-KRAS G12D 4F10 antibody conjugate (KRAS G12D iTAb (Compound 1)). Fully human IgGs against bacterial proteins were produced and modified with the same procedure as the anti-KRAS G12D antibody conjugates, then included as experimental control antibody conjugates.

Example 8. Internalized Anti-KRAS G12D Antibody Conjugates Attenuate Oncogenic Signaling in Human Pancreatic Cancer Cells Expressing KRAS G12D The effect of internalized anti-KRAS G12D antibodies on oncogenic signaling was examined in ASPC-1 human pancreatic cancer cells expressing KRAS G12D. U2OS osteosarcoma cells expressing wild-type KRAS were used as a control. FIG. 5A shows the level of ERK 1/2 phosphorylation in U2OS KRAS wild type cells, in U2OS KRAS wild type cells stimulated with EGF, and in ASPC-1 cells with a KRAS G12D mutation after treatment with a control antibody conjugates (Control iTAbs) or treatment with anti-KRAS G12D clone 4F10 antibody conjugates (KRAS G12D iTAb (Compound 1)). As shown in FIG. 5A, the anti-KRAS G12D clone 4F10 antibody conjugates (Compound 1) inhibited level of ERK 1/2 phosphorylation. FIG. 5B shows the percent viability of the KRAS G12D cells after treatment with the control antibody conjugates (Control iTAbs) or the anti-KRAS G12D clone 4F10 antibody conjugates (KRAS G12D iTAb (Compound 1)). FIG. 5B shows that the anti-KRAS G12D clone 4F10 antibody conjugates decrease cell viability.

Figure 6A:
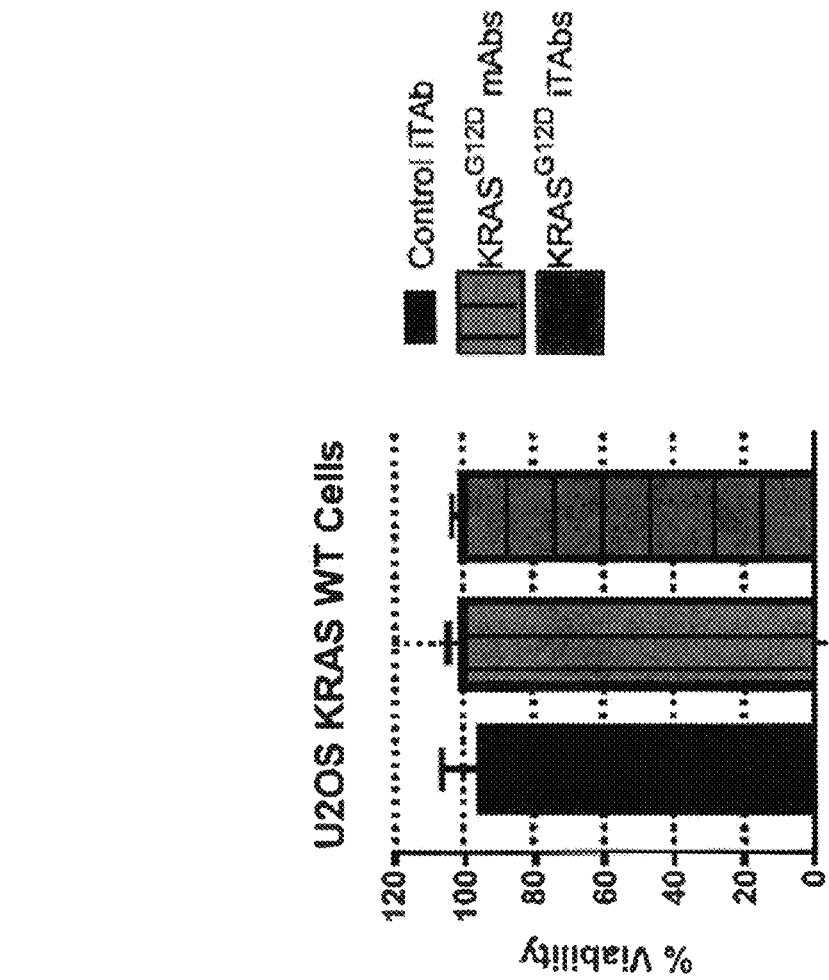
FIG. 6A is a graph showing that the anti-KRAS G12D 4F10 antibody conjugate (Compound 1) did not affect viability of U2OS cells. Control antibody conjugate (Control iTAb), anti-KRAS G12D 4F10 monoclonal antibody (KRAS$^{G12D}$ mAb) and anti-KRAS G12D 4F10 antibody conjugate (KRAS$^{G12D}$ iTAb (Compound 1)) were each tested. Percent viability is shown on the y-axis.
Figure 6B:
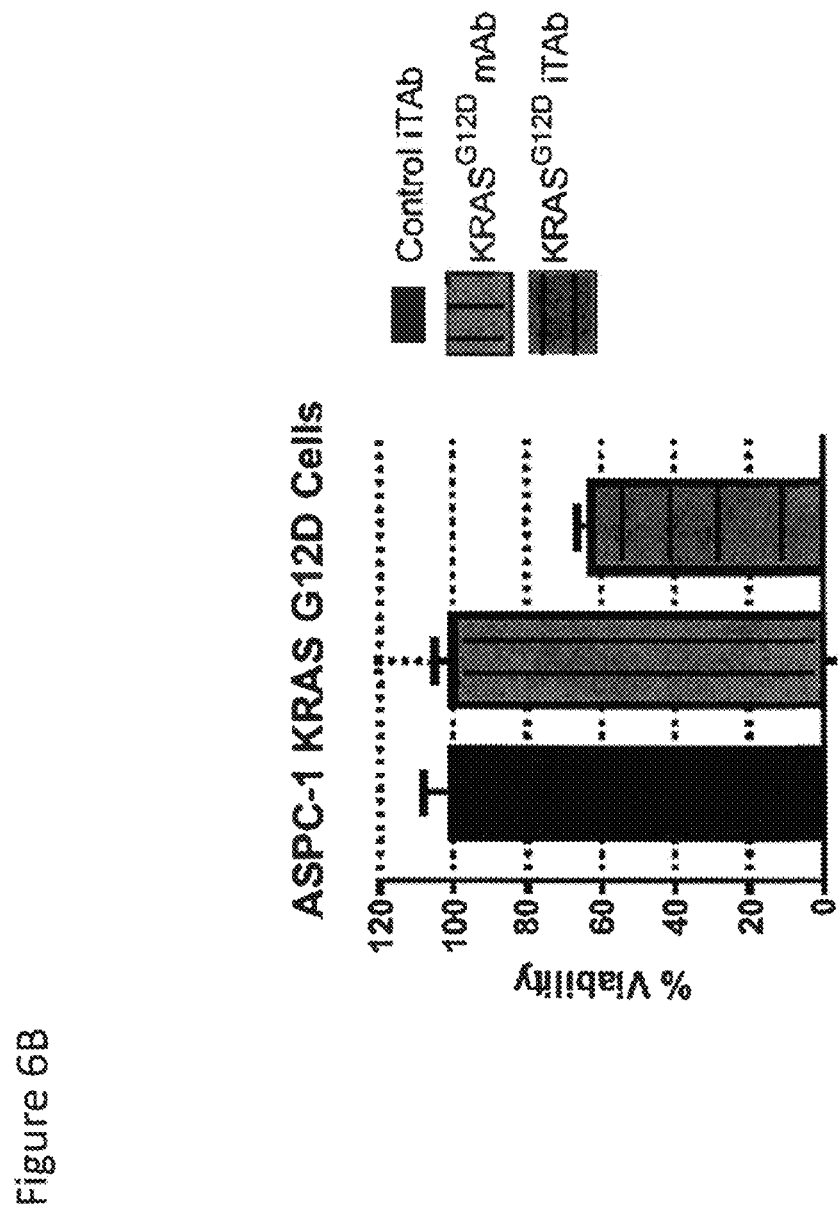
FIG. 6B is a graph that shows that the anti-KRAS G12D 4F10 antibody conjugate (Compound 1) had cytotoxic activity in ASPC-1 cells. Control antibody conjugate (Control iTAb), anti-KRAS G12D monoclonal antibody (KRAS$^{G12D}$ mAb) and anti-KRAS G12D 4F10 antibody conjugate (KRAS$^{G12D}$ iTAb (Compound 1)) were each tested. Percent viability is shown on the y-axis.

Example 9. Drug Sensitivity to KRAS G12D Antibody Conjugate in a 2D Tumor Growth Assay The drug sensitivity to KRAS G12D 4F10 antibody conjugate (Compound 1) was tested in a 2-dimensional tumor growth assay in U2OS osteosarcoma cells expressing wild-type KRAS (a control) and ASPC-1 human pancreatic cancer cells expressing the KRAS G12D mutation. Control antibody conjugate (Control iTAb), anti-KRAS G12D 4F10 monoclonal antibody (KRAS$^{G12D}$ mAb) and anti-KRAS G12D 4F10 antibody conjugate (KRAS$^{G12D}$ iTAb (Compound 1)) were each tested for their effect on U2OS and ASPC-1 cells. A CellTiter-Glo (CTG) assay was performed to determine cell viability. The results are shown in FIG. 6A for U2OS KRAS wild type cells and in FIG. 6B for ASPC-1 KRAS G12D expressing human pancreatic cancer cells. As shown in FIG. 6A and FIG. 6B, anti-KRAS G12D 4F10 antibody conjugates (Compound 1) showed cytotoxic activity in ASPC-1 cells, but not U2OS cells.

TABLE 4

Antibody Amino Acid Sequences

| | Heavy chain variable domain regions | Light chain variable domain regions |
|---|---|---|
| K3-1F4 | EVQLVQSGGGVVQPGRSLRLSCAAS<u>GFTS</u> <u>SNYGMH</u>WVRQAPGKGLEWVAV<u>ISHDGSKK</u> <u>YYADSVKG</u>RFTISRDNSKNTLFVQLSSLR PEDTAVYYCAT<u>SLYSSMDL</u>WGQGTTVTVS S<br>SEQ ID NO. 1 | QSVVTQPPSVSAAPGQKVTISC<u>SGSNSNI</u> <u>GKNYVS</u>WFQQVPGTAPKLLIF<u>EDNQRPSG</u> IPDRFSASKSGTSASLAISGLQSEDEADY YC<u>AAWDDSLNAHWV</u>FGGGTKLTVL<br>SEQ ID NO. 2 |
| K3-1F4 | HC CDR1<br>GFTSSNYGMH<br>SEQ ID NO. 75<br>HC CDR2<br>VISHDGSKKYYADSVKG<br>SEQ ID NO. 76 | LC CDR1<br>SGSNSNIGKNYVS<br>SEQ ID NO. 78<br>LC CDR2<br>EDNQRPS<br>SEQ ID NO. 79 |

TABLE 4-continued

Antibody Amino Acid Sequences

| | Heavy chain variable domain regions | Light chain variable domain regions |
|---|---|---|
| | HC CDR3<br>SLYSSMDL<br>SEQ ID NO. 77 | LC CDR3<br>AAWDDSLNAHWV<br>SEQ ID NO. 80 |
| K3-1A7 | QVQLVESGGGVVQPGRSLRLSCTNS<u>GFSF</u><br><u>SGYAMH</u>WVRQAPGKGLEWVA<u>VISFDGSHK</u><br><u>YYADSVKG</u>RFTISRDNSKNTLYLHMNSLR<br>AEDTAVYYCAS<u>GGNYYGSGTIVSHGLDF</u>W<br>GQGTTVTVSS<br>SEQ ID NO. 3 | DIVMTQSPSTLSASVGDRVTITC<u>RASQSI</u><br><u>SSWLA</u>WYQQKPGKAPKVLIY<u>KASSLES</u>GV<br>PSRFSGSGSGTEFTLTISSLQPDDFAAYY<br>C<u>QHYNSYPYT</u>FGQGTKLEIK<br>SEQ ID NO. 4 |
| K3-1A7 | HC CDR1<br>GFSFSGYAMH<br>SEQ ID NO. 81<br>HC CDR2<br>VISFDGSHKYYADSVKG<br>SEQ ID NO. 82<br>HC CDR3<br>GGNYYGSGTIVSHGLDF<br>SEQ ID NO. 83 | LC CDR1<br>RASQSISSWLA<br>SEQ ID NO. 84<br>LC CDR2<br>KASSLES<br>SEQ ID NO. 85<br>LC CDR3<br>QHYNSYPYT<br>SEQ ID NO. 86 |
| K3-2B2 | QVQLVESGGGVVQPGRSLRLSCTNS<u>GFSF</u><br><u>SGYAMH</u>WVRQAPGKGLEWVA<u>VISFDGSHK</u><br><u>YYADSVKG</u>RFTISRDNSKNTLYLHMNSLR<br>AEDTAVYYCAS<u>GGNYYGSGTIVSHGMDV</u>W<br>GQGTTVTVSS<br>SEQ ID NO. 5 | SSELTQDPAVSVALGQTVRITC<u>QGDSLRS</u><br><u>YYAS</u>WYQQKPGQAPVLVIY<u>GKNNRPS</u>GIP<br>DRFSGSSSGNTASLTITGAQAEDEADYYC<br><u>NSRDSSGNH</u>RGGGTKLTVL<br>SEQ ID NO. 6 |
| K3-2B2 | HC CDR1<br>GFSFSGYAMH<br>SEQ ID NO. 87<br>HC CDR2<br>VISFDGSHKYYADSVKG<br>SEQ ID NO. 88<br>HC CDR3<br>GGNYYGSGTIVSHGMDV<br>SEQ ID NO. 89 | LC CDR1<br>QGDSLRSYYAS<br>SEQ ID NO. 90<br>LC CDR2<br>GKNNRPS<br>SEQ ID NO. 91<br>LC CDR3<br>NSRDSSGNH<br>SEQ ID NO. 92 |
| K3-2C2 | QVQLVESGGGVVQPGRSLRLSCSNS<u>GFSF</u><br><u>SGYTMH</u>WVRQAPGKGLEWVA<u>VISFDGSHK</u><br><u>YYADSVKG</u>RFTISRDNSKNTLYLHMNSLR<br>AEDTAVYYCAK<u>KMHYGSGAYHFDL</u>WGQGT<br>LVTVSS<br>SEQ ID NO. 7 | DIVMTQSPSSLSASVGDRVTITC<u>RASQSI</u><br><u>SNYLN</u>WYQQKPGKAPKLLIY<u>AASSLQS</u>GV<br>PSRFSGSGSGDFTLTISSLQPEDFATYY<br>C<u>QQSYSSPFT</u>FGPGTKVDIK<br>SEQ ID NO. 8 |
| K3-2C2 | HC CDR1<br>GFSFSGYTMH<br>SEQ ID NO. 93<br>HC CDR2<br>VISFDGSHKYYADSVKG<br>SEQ ID NO. 94<br>HC CDR3<br>KMHYGSGAYHFDL<br>SEQ ID NO. 95 | LC CDR1<br>RASQSISNYLN<br>SEQ ID NO. 96<br>LC CDR2<br>AASSLQS<br>SEQ ID NO. 97<br>LC CDR3<br>QQSYSSPFT<br>SEQ ID NO. 98 |
| K3-2H8 | EVQLLESGGGVVQPGRSLRLSCTNS<u>GFSF</u><br><u>SGYAMH</u>WVRQAPGKGLEWVA<u>VISFDGSHK</u><br><u>YYADSVKG</u>RFTISRDNSKNTLYLHMNSLT<br>AEDTAVYYCAS<u>GGNYYGSGTIVSHGMDV</u>W<br>GQGTTVTVSS<br>SEQ ID NO. 9 | QSVLTQPASVSGSPGQSITISC<u>TGTSSDV</u><br><u>GGYNYVS</u>WYQQHPGKAPKLMIY<u>DVSNRPS</u><br>GVSNRFSGSKSGNTASLTISGLQAEDEAD<br>YYC<u>SSYTSSSTLVV</u>FGGGTKLTVL<br>SEQ ID NO. 10 |
| K3-2H8 | HC CDR1<br>GFSFSGYAMH<br>SEQ ID NO. 99<br>HC CDR2<br>VISFDGSHKYYADSVKG<br>SEQ ID NO. 100<br>HC CDR3<br>GGNYYGSGTIVSHGMDV<br>SEQ ID NO. 101 | LC CDR1<br>TGTSSDVGGYNYVS<br>SEQ ID NO. 102<br>LC CDR2<br>DVSNRPS<br>SEQ ID NO. 103<br>LC CDR3<br>SSYTSSSTLVV<br>SEQ ID NO. 104 |
| K3-3E8 | EVQLLEPGGGVVQPGRSLRLSCTNS<u>GFSF</u><br><u>SGYAMH</u>WVRQAPGKGLEWVA<u>VISFDGSHK</u><br><u>YYADSVKG</u>RFTISRDNSKNTLYLHMNSLR | QSALTQPRSVSGSPGQSVTISC<u>TGTSSNV</u><br><u>GGYNHVS</u>WYQQHPGKAPKVIIY<u>DVNKRPS</u><br>GVSHRFSGSKSANTASLTISGLQAEDEAD |

TABLE 4-continued

Antibody Amino Acid Sequences

| Heavy chain variable domain regions | Light chain variable domain regions |
|---|---|
| AEDTAVYYCAS<u>GGNYYGSGTIVSHGMDV</u>W GQGTTVTVSS<br>SEQ ID NO. 11 | YYC<u>SSYTTSSTYV</u>FGTGTKLTVL<br>SEQ ID NO. 12 |

K3-3E8
| HC CDR1<br>GFSFSGYAMH<br>SEQ ID NO. 105<br>HC CDR2<br>VISFDGSHKYYADSVKG<br>SEQ ID NO. 106<br>HC CDR3<br>GGNYYGSGTIVSHGMDV<br>SEQ ID NO. 107 | LC CDR1<br>TGTSSNVGGYNHVS<br>SEQ ID NO. 108<br>LC CDR2<br>DVNKRPS<br>SEQ ID NO. 109<br>LC CDR3<br>SSYTTSSTYV<br>SEQ ID NO. 110 |

K3-4D9
| QVQLVESAGGVVQPGRSLRLSCTNS<u>GFSF SGYAMH</u>WVRQAPGKGLEWVA<u>VISFDGSHK YYADSVKG</u>RFTISRDNSKNTLYLHMNSLT AEDTAVYYCAS<u>GGNYYGSGTIVSHGMDV</u>W GQGTTVTVSS<br>SEQ ID NO. 13 | QSVLTQPASVSGSPGQSITISC<u>TGTSSDV GGYKYVS</u>WYQQYPGKAPKLMIY<u>DVSKRPS</u> GVSNRFSGSKSGNTASLTISGLQAEDEAD YYC<u>NSYTSSRIYV</u>FGTGTKLTVL<br>SEQ ID NO. 14 |

K3-4D9
| HC CDR1<br>GFSFSGYAMH<br>SEQ ID NO. 111<br>HC CDR2<br>VISFDGSHKYYADSVKG<br>SEQ ID NO. 112<br>HC CDR3<br>GGNYYGSGTIVSHGMDV<br>SEQ ID NO. 113 | LC CDR1<br>TGTSSDVGGYKYVS<br>SEQ ID NO. 114<br>LC CDR2<br>DVSKRPS<br>SEQ ID NO. 115<br>LC CDR3<br>NSYTSSRIYV<br>SEQ ID NO. 116 |

K3-4F10
| EVQLLEPGGGVVQPGRSLRLSCTNS<u>GFSF SGYAMH</u>WVRQAPGKGLEWVA<u>VISFDGSHK YYADSVKG</u>RFTISRDNSKNTLYLHMNSLR AEDTAVYYCAS<u>GGNYYGSGTIVSHGMDV</u>W GQGTTVTVSS<br>SEQ ID NO. 15 | QSVLTQPASVSGSPGQSITISC<u>TGTSNDI GAYNYVS</u>WYQQHPGKAPKLMIY<u>DVNNRPS</u> GVPDRFSGSKSGNMASLTISGLQAEDDAD YYC<u>SSYTSSSTLVV</u>FGGGTKLTVL<br>SEQ ID NO. 16 |

K3-4F10
| HC CDR1<br>GFSFSGYAMH<br>SEQ ID NO. 117<br>HC CDR2<br>VISFDGSHKYYADSVKG<br>SEQ ID NO. 118<br>HC CDR3<br>GGNYYGSGTIVSHGMDV<br>SEQ ID NO. 119 | LC CDR1<br>TGTSNDIGAYNYVS<br>SEQ ID NO. 120<br>LC CDR2<br>DVNNRPS<br>SEQ ID NO. 121<br>LC CDR3<br>SSYTSSSTLVV<br>SEQ ID NO. 122 |

K3-5H6
| QVQLVQSGGGVVQPGRSLRLSCTNS<u>GFSF SGYAMH</u>WVRQAPGKGLEWVA<u>VISFDGSHK YYADSVKG</u>RFTISRDNSKNTLYLHMNSVR AEDTAVYYCAS<u>GGNHYGSGTIVSHGMDV</u>R GQGTTVTVSS<br>SEQ ID NO. 17 | QSVLTQPASVSGSPGQSITISC<u>TGTSSDI GGSNWVS</u>WYQQHPGKAPKLMIY<u>DVSKRPS</u> GVSNRFSGSKSGNTASLTISGLQAEDEAD YYC<u>SSYTSSSTYV</u>FGTGTKLTVL<br>SEQ ID NO. 18 |

K3-5H6
| HC CDR1<br>GFSFSGYAMH<br>SEQ ID NO. 123<br>HC CDR2<br>VISFDGSHKYYADSVKG<br>SEQ ID NO. 124<br>HC CDR3<br>GGNHYGSGTIVSHGMDV<br>SEQ ID NO. 125 | LC CDR1<br>TGTSSDIGGSNWVS<br>SEQ ID NO. 126<br>LC CDR2<br>DVSKRPS<br>SEQ ID NO. 127<br>LC CDR3<br>SSYTSSSTYV<br>SEQ ID NO. 128 |

K5-1F12
| QVQLVESGGGLVQPGGSLRLSCAAS<u>GFTF SSYWMS</u>WVRQAPGKGLEWVG<u>FIRSKAYGG TTEYAASVKG</u>RFTISRDDSKSIAYLQMNS LKTEDTAVYYCTR<u>DGGSYFDY</u>WGQGTLVT VSS<br>SEQ ID NO. 19 | QAGLTQPASVSGSPGQSITISC<u>TGTSSDV GGYNYVS</u>WYQQHPGKAPKLMIY<u>DVSKRPS</u> GVSNRFSGSKSGNTASLTISGLQAEDEAD YYC<u>SSYTSSSTYV</u>FGTGTKVTVL<br>SEQ ID NO. 20 |

TABLE 4-continued

Antibody Amino Acid Sequences

| | Heavy chain variable domain regions | Light chain variable domain regions |
|---|---|---|
| K5-1F12 | HC CDR1<br>GFTFSSYWMS<br>SEQ ID NO. 129<br>HC CDR2<br>FIRSKAYGGTTEYAASVKG<br>SEQ ID NO. 130<br>HC CDR3<br>DGGSYFDY<br>SEQ ID NO. 131 | LC CDR1<br>TGTSSDVGGYNYVS<br>SEQ ID NO. 132<br>LC CDR2<br>DVSKRPS<br>SEQ ID NO. 133<br>LC CDR3<br>SSYTSSSTYV<br>SEQ ID NO. 134 |
| 1F4_1H2 | EVQLVQSGGGVVQPGRSLRLSCAAS<u>GFTS</u><br><u>SLNGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 21 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDYGSTHWV</u>FGGGTKLTVL<br>SEQ ID NO. 22 |
| 1F4_1H2 | HC CDR1<br>GFTSSLNGMH<br>SEQ ID NO. 135<br>HC CDR2<br>VISHDGSKKYYADSVKG<br>SEQ ID NO. 136<br>HC CDR3<br>SLYSSMDL<br>SEQ ID NO. 137 | LC CDR1<br>SGSNSNIGKNYVS<br>SEQ ID NO. 138<br>LC CDR2<br>EDNQRPS<br>SEQ ID NO. 139<br>LC CDR3<br>AAWDDYGSTHWV<br>SEQ ID NO. 140 |
| 1F4_1C3 | EVQLVQSGGGVVQPGRSLRLSCAAS<u>GFTS</u><br><u>RQYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 23 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDGRKVHWV</u>FGGGTKLTVL<br>SEQ ID NO. 24 |
| 1F4_1C3 | HC CDR1<br>GFTSRQYGMH<br>SEQ ID NO. 141<br>HC CDR2<br>VISHDGSKKYYADSVKG<br>SEQ ID NO. 142<br>HC CDR3<br>SLYSSMDL<br>SEQ ID NO. 143 | LC CDR1<br>SGSNSNIGKNYVS<br>SEQ ID NO. 144<br>LC CDR2<br>EDNQRPS<br>SEQ ID NO. 145<br>LC CDR3<br>AAWDDGRKVHWV<br>SEQ ID NO. 146 |
| 1F4_1D3 | EVQLVQSGGGVVQPGRSLRLSCAAS<u>GFTS</u><br><u>STYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 25 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSRTTHWV</u>FGGGTKLTVL<br>SEQ ID NO. 26 |
| 1F4_1D3 | HC CDR1<br>GFTSSTYGMH<br>SEQ ID NO. 147<br>HC CDR2<br>VISHDGSKKYYADSVKG<br>SEQ ID NO. 148<br>HC CDR3<br>SLYSSMDL<br>SEQ ID NO. 149 | LC CDR1<br>SGSNSNIGKNYVS<br>SEQ ID NO. 150<br>LC CDR2<br>EDNQRPS<br>SEQ ID NO. 151<br>LC CDR3<br>AAWDDSRTTHWV<br>SEQ ID NO. 152 |
| 1F4_1E6 | EVQLVQSGGGVVQPGRSLRLSCAAS<u>GFTS</u><br><u>RPYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 27 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDFHSEHWV</u>FGGGTKLTVL<br>SEQ ID NO. 28 |

TABLE 4-continued

Antibody Amino Acid Sequences

| | Heavy chain variable domain regions | Light chain variable domain regions |
|---|---|---|
| 1F4_1E6 | HC CDR1<br>GFTSRPYGMH<br>SEQ ID NO. 153<br>HC CDR2<br>VISHDGSKKYYADSVKG<br>SEQ ID NO. 154<br>HC CDR3<br>SLYSSMDL<br>SEQ ID NO. 155 | LC CDR1<br>SGSNSNIGKNYVS<br>SEQ ID NO. 156<br>LC CDR2<br>EDNQRPS<br>SEQ ID NO. 157<br>LC CDR3<br>AAWDDFHSEHWV<br>SEQ ID NO. 158 |
| 1F4_1F6 | EVQLVQSGGGVVQPGRSLRLSCAAS<u>GFTS</u><br><u>ATYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 29 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDSSDTHWV</u>FGGGTKLTVL<br>SEQ ID NO. 30 |
| 1F4_1F6 | HC CDR1<br>GFTSATYGMH<br>SEQ ID NO. 159<br>HC CDR2<br>VISHDGSKKYYADSVKG<br>SEQ ID NO. 160<br>HC CDR3<br>SLYSSMDL<br>SEQ ID NO. 161 | LC CDR1<br>SGSNSNIGKNYVS<br>SEQ ID NO. 162<br>LC CDR2<br>EDNQRPS<br>SEQ ID NO. 163<br>LC CDR3<br>AAWDDSSDTHWV<br>SEQ ID NO. 164 |
| 1F4_1G6 | EVQLVQSGGGVVQPGRSLRLSCAAS<u>GFTS</u><br><u>SFHGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 31 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDSGDVHWV</u>FGGGTKLTVL<br>SEQ ID NO. 32 |
| 1F4_1G6 | HC CDR1<br>GFTSSFHGMH<br>SEQ ID NO. 165<br>HC CDR2<br>VISHDGSKKYYADSVKG<br>SEQ ID NO. 166<br>HC CDR3<br>SLYSSMDL<br>SEQ ID NO. 167 | LC CDR1<br>SGSNSNIGKNYVS<br>SEQ ID NO. 168<br>LC CDR2<br>EDNQRPS<br>SEQ ID NO. 169<br>LC CDR3<br>AAWDDSGDVHWV<br>SEQ ID NO. 170 |
| 1F4_1E3 | EVQLVQSGGGVVQPGRSLRLSCAAS<u>GFTS</u><br><u>RHPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 33 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDYRGPHWV</u>FGGGTKLTVL<br>SEQ ID NO. 34 |
| 1F4_1E3 | HC CDR1<br>GFTSRHPGMH<br>SEQ ID NO. 171<br>HC CDR2<br>VISHDGSKKYYADSVKG<br>SEQ ID NO. 172<br>HC CDR3<br>SLYSSMDL<br>SEQ ID NO. 173 | LC CDR1<br>SGSNSNIGKNYVS<br>SEQ ID NO. 174<br>LC CDR2<br>EDNQRPS<br>SEQ ID NO. 175<br>LC CDR3<br>AAWDDYRGPHWV<br>SEQ ID NO. 176 |
| 1F4_3D11 | EVQLVQSGGGVVQPGRSLRLSCAAS<u>GFTS</u><br><u>RHPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 35 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDYRGPHWV</u>FGGGTKLTVL<br>SEQ ID NO. 36 |

TABLE 4-continued

Antibody Amino Acid Sequences

| | Heavy chain variable domain regions | Light chain variable domain regions |
|---|---|---|
| 1F4_3D11 | HC CDR1<br>GFTSRHPGMH<br>SEQ ID NO. 177<br>HC CDR2<br>VISHDGSKKYYADSVKG<br>SEQ ID NO. 178<br>HC CDR3<br>SLYSSMDL<br>SEQ ID NO. 179 | LC CDR1<br>SGSNSNIGKNYVS<br>SEQ ID NO. 180<br>LC CDR2<br>EDNQRPS<br>SEQ ID NO. 181<br>LC CDR3<br>AAWDDYRGPHWV<br>SEQ ID NO. 182 |
| 1F4_4E10 | EVQLVQSGGGVVQPGRSLRLSCAAS<u>GFTS</u><br><u>RAPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 37 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDHNGEHWV</u>FGGGTKLTVL<br>SEQ ID NO. 38 |
| 1F4_4E10 | HC CDR1<br>GFTSRAPGMH<br>SEQ ID NO. 183<br>HC CDR2<br>VISHDGSKKYYADSVKG<br>SEQ ID NO. 184<br>HC CDR3<br>SLYSSMDL<br>SEQ ID NO. 185 | LC CDR1<br>SGSNSNIGKNYVS<br>SEQ ID NO. 186<br>LC CDR2<br>EDNQRPS<br>SEQ ID NO. 187<br>LC CDR3<br>AAWDDHNGEHWV<br>SEQ ID NO. 188 |
| 1F4_4F10 | EVQLVQSGGGVVQPGRSLRLSCAAS<u>GFTS</u><br><u>RHPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 39 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDKFGVHWV</u>FGGGTKLTVL<br>SEQ ID NO. 40 |
| 1F4_4F10 | HC CDR1<br>GFTSRHPGMH<br>SEQ ID NO. 189<br>HC CDR2<br>VISHDGSKKYYADSVKG<br>SEQ ID NO. 190<br>HC CDR3<br>SLYSSMDL<br>SEQ ID NO. 191 | LC CDR1<br>SGSNSNIGKNYVS<br>SEQ ID NO. 192<br>LC CDR2<br>EDNQRPS<br>SEQ ID NO. 193<br>LC CDR3<br>AAWDDKFGVHWV<br>SEQ ID NO. 194 |
| 1F4_4A12 | EVQLVQSGGGVVQPGRSLRLSCAAS<u>GFTS</u><br><u>RKYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 41 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSPTIHWV</u>FGGGTKLTVL<br>SEQ ID NO. 42 |
| 1F4_4A12 | HC CDR1<br>GFTSRKYGMH<br>SEQ ID NO. 195<br>HC CDR2<br>VISHDGSKKYYADSVKG<br>SEQ ID NO. 196<br>HC CDR3<br>SLYSSMDL<br>SEQ ID NO. 197 | LC CDR1<br>SGSNSNIGKNYVS<br>SEQ ID NO. 198<br>LC CDR2<br>EDNQRPS<br>SEQ ID NO. 199<br>LC CDR3<br>AAWDDSPTIHWV<br>SEQ ID NO. 200 |
| 1F4_4D12 | EVQLVQSGGGVVQPGRSLRLSCAAS<u>GFTS</u><br><u>HNKGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 43 | QSVVTQPPSVSAAPGQKVTISC<u>SGSNFNI</u><br><u>GKNYVS</u>WFQQVPGTAPKLLIF<u>EDNQRPSG</u><br>IPDRFSASKSGTSASLAISGLQSEDEADY<br>YC<u>AAWDDFAGVHWV</u>FGGGTKLTVL<br>SEQ ID NO. 44 |

TABLE 4-continued

Antibody Amino Acid Sequences

| | Heavy chain variable domain regions | Light chain variable domain regions |
|---|---|---|
| 1F4_4D12 | HC CDR1<br>GFTSHNKGMH<br>SEQ ID NO. 201<br>HC CDR2<br>VISHDGSKKYYADSVKG<br>SEQ ID NO. 202<br>HC CDR3<br>SLYSSMDL<br>SEQ ID NO. 203 | LC CDR1<br>SGSNFNIGKNYVS<br>SEQ ID NO. 204<br>LC CDR2<br>EDNQRPS<br>SEQ ID NO. 205<br>LC CDR3<br>AAWDDFAGVHWV<br>SEQ ID NO. 206 |
| 1F4_4E12 | EVQLVQSGGGVVQPGRSLRLSCAAS<u>GFTS</u><br><u>YKYGMH</u>WVRQAPGKGLEWVA<u>VISHDGSKK</u><br><u>YYADSVKG</u>RFTISRDNSKNTLFVQLSSLR<br>PEDTAVYYCAS<u>SLYSSMDL</u>WGQGTTVTVS<br>S<br>SEQ ID NO. 45 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSFSEHWV</u>FGGGTKLTVL<br>SEQ ID NO. 46 |
| 1F4_4E12 | HC CDR1<br>GFTSYKYGMH<br>SEQ ID NO. 207<br>HC CDR2<br>VISHDGSKKYYADSVKG<br>SEQ ID NO. 208<br>HC CDR3<br>SLYSSMDL<br>SEQ ID NO. 209 | LC CDR1<br>SGSNSNIGKNYVS<br>SEQ ID NO. 210<br>LC CDR2<br>EDNQRPS<br>SEQ ID NO. 211<br>LC CDR3<br>AAWDDSFSEHWV<br>SEQ ID NO. 212 |
| 1F4_5C4 | EVQLVQSGGGVVQPGRSLRLSCAAS<u>GFTS</u><br><u>RAPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 47 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDQNGVHWV</u>FGGGTKLTVL<br>SEQ ID NO. 48 |
| 1F4_5C4 | HC CDR1<br>GFTSRAPGMH<br>SEQ ID NO. 213<br>HC CDR2<br>VISHDGSKKYYADSVKG<br>SEQ ID NO. 214<br>HC CDR3<br>SLYSSMDL<br>SEQ ID NO. 215 | LC CDR1<br>SGSNSNIGKNYVS<br>SEQ ID NO. 216<br>LC CDR2<br>EDNQRPS<br>SEQ ID NO. 217<br>LC CDR3<br>AAWDDQNGVHWV<br>SEQ ID NO. 218 |
| 1F4_5A4 | EVQLVQSGGGVVQPGRSLRLSCAAS<u>GFTS</u><br><u>RSPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 49 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDLRGVHWV</u>FGGGTKLTVL<br>SEQ ID NO. 50 |
| 1F4_5A4 | HC CDR1<br>GFTSRSPGMH<br>SEQ ID NO. 219<br>HC CDR2<br>VISHDGSKKYYADSVKG<br>SEQ ID NO. 220<br>HC CDR3<br>SLYSSMDL<br>SEQ ID NO. 221 | LC CDR1<br>SGSNSNIGKNYVS<br>SEQ ID NO. 222<br>LC CDR2<br>EDNQRPS<br>SEQ ID NO. 223<br>LC CDR3<br>AAWDDLRGVHWV<br>SEQ ID NO. 224 |
| 1F4_5B7 | EVQLVQSGGGVVQPGRSLRLSCAAS<u>GFTS</u><br><u>RHHGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 51 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDRHGTHWV</u>FGGGTKLTVL<br>SEQ ID NO. 52 |

TABLE 4-continued

Antibody Amino Acid Sequences

| | Heavy chain variable domain regions | Light chain variable domain regions |
|---|---|---|
| 1F4_5B7 | HC CDR1<br>GFTSRHHGMH<br>SEQ ID NO. 225<br>HC CDR2<br>VISHDGSKKYYADSVKG<br>SEQ ID NO. 226<br>HC CDR3<br>SLYSSMDL<br>SEQ ID NO.227 | LC CDR1<br>SGSNSNIGKNYVS<br>SEQ ID NO. 228<br>LC CDR2<br>EDNQRPS<br>SEQ ID NO. 229<br>LC CDR3<br>AAWDDRHGTHWV<br>SEQ ID NO. 230 |
| 1F4_5F8 | EVQLVQSGGGVVQPGRSLRLSCAAS<u>GFTS</u><br><u>RNPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 53 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDSTGVHWV</u>FGGGTKLTVL<br>SEQ ID NO. 54 |
| 1F4_5F8 | HC CDR1<br>GFTSRNPGMH<br>SEQ ID NO. 231<br>HC CDR2<br>VISHDGSKKYYADSVKG<br>SEQ ID NO. 232<br>HC CDR3<br>SLYSSMDL<br>SEQ ID NO. 233 | LC CDR1<br>SGSNSNIGKNYVS<br>SEQ ID NO. 234<br>LC CDR2<br>EDNQRPS<br>SEQ ID NO. 235<br>LC CDR3<br>AAWDDSTGVHWV<br>SEQ ID NO. 236 |
| 1F4_5D3 | EVQLVQSGGGVVQPGRSLRLSCAAS<u>GFTS</u><br><u>RTYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 55 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDLPTDHWV</u>FGGGTKLTVL<br>SEQ ID NO. 56 |
| 1F4_5D3 | HC CDR1<br>GFTSRTYGMH<br>SEQ ID NO. 237<br>HC CDR2<br>VISHDGSKKYYADSVKG<br>SEQ ID NO. 238<br>HC CDR3<br>SLYSSMDL<br>SEQ ID NO. 239 | LC CDR1<br>SGSNSNIGKNYVS<br>SEQ ID NO. 240<br>LC CDR2<br>EDNQRPS<br>SEQ ID NO. 241<br>LC CDR3<br>AAWDDLPTDHWV<br>SEQ ID NO. 242 |
| 1F4_5G5 | EVQLVQSGGGVVQPGRSLRLSCAAS<u>GFTS</u><br><u>RQYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 57 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDYSGVHWV</u>FGGGTKLTVL<br>SEQ ID NO. 58 |
| 1F4_5G5 | HC CDR1<br>GFTSRQYGMH<br>SEQ ID NO. 243<br>HC CDR2<br>VISHDGSKKYYADSVKG<br>SEQ ID NO. 244<br>HC CDR3<br>SLYSSMDL<br>SEQ ID NO. 245 | LC CDR1<br>SGSNSNIGKNYVS<br>SEQ ID NO. 246<br>LC CDR2<br>EDNQRPS<br>SEQ ID NO. 247<br>LC CDR3<br>AAWDDYSGVHWV<br>SEQ ID NO. 248 |
| 1F4_5A10 | EVQLVQSGGGVVQPGRSLRLSCAAS<u>GFTS</u><br><u>SPYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 59 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDNPRDHWV</u>FGGGTKLTVL<br>SEQ ID NO. 60 |

TABLE 4-continued

Antibody Amino Acid Sequences

| | Heavy chain variable domain regions | Light chain variable domain regions |
|---|---|---|
| 1F4_5A10 | HC CDR1<br>GFTSSPYGMH<br>SEQ ID NO. 249<br>HC CDR2<br>VISHDGSKKYYADSVKG<br>SEQ ID NO. 250<br>HC CDR3<br>SLYSSMDL<br>SEQ ID NO. 251 | LC CDR1<br>SGSNSNIGKNYVS<br>SEQ ID NO. 252<br>LC CDR2<br>EDNQRPS<br>SEQ ID NO. 253<br>LC CDR3<br>AAWDDNPRDHWV<br>SEQ ID NO. 254 |
| 1F4_5B12 | EVQLVQSGGGVVQPGRSLRLSCAAS<u>GFTS</u><br><u>SKPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 61 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDLRGVHWV</u>FGGGTKLTVL<br>SEQ ID NO. 62 |
| 1F4_5B12 | HC CDR1<br>GFTSSKPGMH<br>SEQ ID NO. 255<br>HC CDR2<br>VISHDGSKKYYADSVKG<br>SEQ ID NO. 256<br>HC CDR3<br>SLYSSMDL<br>SEQ ID NO. 257 | LC CDR1<br>SGSNSNIGKNYVS<br>SEQ ID NO. 258<br>LC CDR2<br>EDNQRPS<br>SEQ ID NO. 259<br>LC CDR3<br>AAWDDLRGVHWV<br>SEQ ID NO. 260 |
| 1F4_5C5 | EVQLVQSGGGVVQPGRSLRLSCAAS<u>GFTS</u><br><u>KKYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 63 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDLGGDHWV</u>FGGGTKLTVL<br>SEQ ID NO. 64 |
| 1F4_5C5 | HC CDR1<br>GFTSKKYGMH<br>SEQ ID NO. 261<br>HC CDR2<br>VISHDGSKKYYADSVKG<br>SEQ ID NO. 262<br>HC CDR3<br>SLYSSMDL<br>SEQ ID NO. 263 | LC CDR1<br>SGSNSNIGKNYVS<br>SEQ ID NO. 264<br>LC CDR2<br>EDNQRPS<br>SEQ ID NO. 265<br>LC CDR3<br>AAWDDLGGDHWV<br>SEQ ID NO. 266 |
| 1F4_5F6 | EVQLVQSGGGVVQPGRSLRLSCAAS<u>GFTS</u><br><u>TLPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 65 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDSAGVHWV</u>FGGGTKLTVL<br>SEQ ID NO. 66 |
| 1F4_5F6 | HC CDR1<br>GFTSTLPGMH<br>SEQ ID NO. 267<br>HC CDR2<br>VISHDGSKKYYADSVKG<br>SEQ ID NO. 268<br>HC CDR3<br>SLYSSMDL<br>SEQ ID NO. 269 | LC CDR1<br>SGSNSNIGKNYVS<br>SEQ ID NO. 270<br>LC CDR2<br>EDNQRPS<br>SEQ ID NO. 271<br>LC CDR3<br>AAWDDSAGVHWV<br>SEQ ID NO. 272 |
| 1F4_5H4 | EVQLVQSGGGVVQPGRSLRLSCAAS<u>GFTS</u><br><u>KMPGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 67 | QSVVTQPPSVSAAPGQKVTISC<u>SGSNSNI</u><br><u>GKNYVS</u>WFQQVPGTAPKLLIF<u>EDNQRPS</u>G<br>IPDRFSASKSGTSASLAISGLQSEDEADY<br>YC<u>AAWDDEHGVHWV</u>FGGGTKLTVL<br>SEQ ID NO. 68 |

TABLE 4-continued

Antibody Amino Acid Sequences

| | Heavy chain variable domain regions | Light chain variable domain regions |
|---|---|---|
| 1F4_5H4 | HC CDR1<br>GFTSKMPGMH<br>SEQ ID NO. 273<br>HC CDR2<br>VISHDGSKKYYADSVKG<br>SEQ ID NO. 274<br>HC CDR3<br>SLYSSMDL<br>SEQ ID NO. 275 | LC CDR1<br>SGSNSNIGKNYVS<br>SEQ ID NO. 276<br>LC CDR2<br>EDNQRPS<br>SEQ ID NO. 277<br>LC CDR3<br>AAWDDEHGVHWV<br>SEQ ID NO. 278 |
| 1F4_5H1 | EVQLVQSGGGVVQPGRSLRLSCAAS<u>GFTS</u><br><u>SNYGMH</u>WVRQAPGKGLEWVA<u>VISHDGSKK</u><br><u>YYADSVKG</u>RFTISRDNSKNTLFVQLSSLR<br>PEDTAVYYCAA<u>SLYSSMDL</u>WGQGTTVTVS<br>S<br>SEQ ID NO. 69 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSLSAHWV</u>FGGGTKLTVL<br>SEQ ID NO. 70 |
| 1F4_5H1 | HC CDR1<br>GFTSSNYGMH<br>SEQ ID NO. 279<br>HC CDR2<br>VISHDGSKKYYADSVKG<br>SEQ ID NO. 280<br>HC CDR3<br>SLYSSMDL<br>SEQ ID NO. 281 | LC CDR1<br>SGSNSNIGKNYVS<br>SEQ ID NO. 282<br>LC CDR2<br>EDNQRPS<br>SEQ ID NO. 283<br>LC CDR3<br>AAWDDSLSAHWV<br>SEQ ID NO. 284 |
| 1F4_5E2 | EVQLVQSGGGVVQPGRSLRLSCAAS<u>GFTS</u><br><u>SNYGMH</u>WVRQAPGKGLEWVA<u>VISHDGSKK</u><br><u>YYADSVKG</u>RFTISRDNSKNTLFVQLSSLR<br>PEDTAVYYCAT<u>SMVSSMDL</u>WGQGTTVTVS<br>S<br>SEQ ID NO. 71 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSLSTHWV</u>FGGGTKLTVL<br>SEQ ID NO. 72 |
| 1F4_5E2 | HC CDR1<br>GFTSSNYGMH<br>SEQ ID NO. 285<br>HC CDR2<br>VISHDGSKKYYADSVKG<br>SEQ ID NO. 286<br>HC CDR3<br>SMVSSMDL<br>SEQ ID NO. 287 | LC CDR1<br>SGSNSNIGKNYVS<br>SEQ ID NO. 288<br>LC CDR2<br>EDNQRPS<br>SEQ ID NO. 289<br>LC CDR3<br>AAWDDSLSTHWV<br>SEQ ID NO. 290 |
| 1F4_5F2 | EVQLVQSGGGVVQPGRSLRLSCAAS<u>GFTS</u><br><u>SNYGMH</u>WVRQAPGKGLEWVA<u>VISHDGSKK</u><br><u>YYADSVKG</u>RFTISRDNSKNTLFVQLSSLR<br>PEDTAVYYCAT<u>SMRSSMDL</u>WGQGTTVTVS<br>S<br>SEQ ID NO. 73 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSLSAHWV</u>FGGGTKLTVL<br>SEQ ID NO. 74 |
| 1F4_5F2 | HC CDR1<br>GFTSSNYGMH<br>SEQ ID NO. 291<br>HC CDR2<br>VISHDGSKKYYADSVKG<br>SEQ ID NO. 292<br>HC CDR3<br>SMRSSMDL<br>SEQ ID NO. 293 | LC CDR1<br>SGSNSNIGKNYVS<br>SEQ ID NO. 294<br>LC CDR2<br>EDNQRPS<br>SEQ ID NO. 295<br>LC CDR3<br>AAWDDSLSAHWV<br>SEQ ID NO. 296 |
| LN-97S | EVQLVQSGGGVVQPGRSLRLSCAAS<u>GFTS</u><br><u>SNYGMH</u>WVRQAPGKGLEWVA<u>VISHDGSKK</u><br><u>YYADSVKG</u>RFTISRDNSKNTLFVQLSSLR<br>PEDTAVYYCAT<u>SLYSSMDL</u>WGQGTTVTVS<br>S<br>SEQ ID NO. 297 | QSVVTQPPSVSAAPGQKVTISC<u>SGSNSNI</u><br><u>GKNYVS</u>WFQQVPGTAPKLLIF<u>EDNQRPSG</u><br>IPDRFSASKSGTSASLAISGLQSEDEADY<br>YC<u>AAWDDSLSAHWV</u>FGGGTKLTVL<br>SEQ ID NO. 298 |

TABLE 4-continued

| Antibody Amino Acid Sequences | | |
|---|---|---|
| | Heavy chain variable domain regions | Light chain variable domain regions |
| LN-97S | HC CDR1<br>GFTSSNYGMH<br>SEQ ID NO. 299<br>HC CDR2<br>VISHDGSKKYYADSVKG<br>SEQ ID NO. 300<br>HC CDR3<br>SLYSSMDL<br>SEQ ID NO. 301 | LC CDR1<br>SGSNSNIGKNYVS<br>SEQ ID NO. 302<br>LC CDR2<br>EDNQRPS<br>SEQ ID NO. 303<br>LC CDR3<br>AAWDDSLSAHWV<br>SEQ ID NO. 304 |

We claim:

1. An anti-KRAS antibody, or an antigen-binding fragment thereof, comprising:
   (a) a heavy chain variable domain comprising the sequence of SEQ ID NO: 33 and a light chain variable domain comprising the sequence of SEQ ID NO: 34;
   (b) a heavy chain variable domain comprising the sequence of SEQ ID NO: 63 and a light chain variable domain comprising the sequence of SEQ ID NO: 64;
   (c) a heavy chain variable domain comprising the sequence of SEQ ID NO: 53 and a light chain variable domain comprising the sequence of SEQ ID NO: 54; or
   (d) a heavy chain variable domain comprising the sequence of SEQ ID NO: 39 and a light chain variable domain comprising the sequence of SEQ ID NO: 40.

2. The anti-KRAS antibody or antigen-binding fragment thereof of claim 1, comprising the heavy chain variable domain comprising the sequence of SEQ ID NO: 33 and the light chain variable domain comprising the sequence of SEQ ID NO: 34.

3. The anti-KRAS antibody or antigen-binding fragment thereof of claim 1, comprising the heavy chain variable domain comprising the sequence of SEQ ID NO: 63 and the light chain variable domain comprising the sequence of SEQ ID NO: 64.

4. The anti-KRAS antibody or antigen-binding fragment thereof of claim 1, comprising the heavy chain variable domain comprising the sequence of SEQ ID NO: 53 and the light chain variable domain comprising the sequence of SEQ ID NO: 54.

5. The anti-KRAS antibody or antigen-binding fragment thereof of claim 1, comprising the heavy chain variable domain comprising the sequence of SEQ ID NO: 39 and the light chain variable domain comprising the sequence of SEQ ID NO: 40.

6. The anti-KRAS antibody of claim 1, wherein the antibody is a human antibody and/or an IgG antibody.

7. The anti-KRAS antigen-binding fragment of claim 1, wherein the antigen-binding fragment is a Fab fragment or an scFv.

8. The anti-KRAS antibody or antigen-binding fragment thereof of claim 1, which is conjugated to an intracellular delivery compound.

9. A pharmaceutical composition comprising the anti-KRAS antibody or antibody fragment thereof of claim 1 and a pharmaceutically acceptable carrier.

10. A method for treating a subject having cancer that expresses KRAS comprising administering the anti-KRAS antibody or antigen-binding fragment thereof of claim 1 to the subject.

11. The method of claim 10, wherein the cancer is a cancer associated with a KRAS mutation.

12. The method of claim 11, wherein the KRAS mutation is G12D mutation.

13. The method of claim 10, wherein the cancer is pancreatic cancer, lung cancer, non-small cell lung cancer, colorectal cancer, prostate cancer, breast cancer, ovarian cancer, head and neck cancer, bladder cancer, melanoma, colorectal cancer, leiomyoma, leiomyosarcoma, glioma, glioblastoma, esophageal cancer, liver cancer, kidney cancer, stomach cancer, colon cancer, cervical cancer, uterine cancer, liver cancer, or a hematological cancer.

14. A nucleic acid encoding an anti-KRAS antibody, or an antigen-binding fragment thereof, comprising:
  (a) a heavy chain variable domain comprising the sequence of SEQ ID NO: 33 and a light chain variable domain comprising the sequence of SEQ ID NO: 34;
  (b) a heavy chain variable domain comprising the sequence of SEQ ID NO: 63 and a light chain variable domain comprising the sequence of SEQ ID NO: 64;
  (c) a heavy chain variable domain comprising the sequence of SEQ ID NO: 53 and a light chain variable domain comprising the sequence of SEQ ID NO: 54; or
  (d) a heavy chain variable domain comprising the sequence of SEQ ID NO: 39 and a light chain variable domain comprising the sequence of SEQ ID NO: 40.

15. A vector comprising the nucleic acid of claim 14.

16. A host cell comprising the nucleic acid of claim 14 or a vector comprising said nucleic acid.

17. An anti-KRAS antibody, or an antigen-binding fragment thereof, comprising:
  (a) a heavy chain variable domain comprising a heavy chain CDR set (CDR1, CDR2, and CDR3) of the sequences of SEQ ID NO: 171, 172, and 173, and a light chain variable domain comprising a light chain CDR set (CDR1, CDR2, and CDR3) of the sequences of SEQ ID NO: 174, 175, and 176;
  (b) a heavy chain variable domain comprising a heavy chain CDR set (CDR1, CDR2, and CDR3) of the sequences of SEQ ID NO: 261, 262, or 263, and a light chain variable domain comprising a light chain CDR set (CDR1, CDR2, and CDR3) of the sequences of SEQ ID NO: 264, 265, and 266;
  (c) a heavy chain variable domain comprising a heavy chain CDR set (CDR1, CDR2, and CDR3) of the sequences of SEQ ID NO: 231, 232, and 233, and a light chain variable domain comprising a light chain CDR set (CDR1, CDR2, and CDR3) of the sequences of SEQ ID NO: 234, 235, and 236; or
  (d) a heavy chain variable domain comprising a heavy chain CDR set (CDR1, CDR2, and CDR3) of the sequences of SEQ ID NO: 189, 190, and 191, and a light chain variable domain comprising a light chain CDR set (CDR1, CDR2, and CDR3) of the sequences of SEQ ID NO: 192, 193, and 194.

18. The anti-KRAS antibody or antigen-binding fragment thereof of claim 17, wherein the anti-KRAS antibody or antigen-binding fragment thereof comprises a heavy chain variable domain comprising a heavy chain CDR set (CDR1, CDR2, and CDR3) of the sequences of SEQ ID NO: 189, 190, and 191, and a light chain variable domain comprising a light chain CDR set (CDR1, CDR2, and CDR3) of the sequences of SEQ ID NO: 192, 193, and 194.

19. The anti-KRAS antibody or antigen-binding fragment thereof of claim 17, wherein the anti-KRAS antibody or antigen-binding fragment thereof comprises:
  (a) a heavy chain variable domain comprising a sequence with at least 95% identity to SEQ ID NO: 33 and a light chain variable domain comprising a sequence with at least 95% identity to SEQ ID NO: 34;
  (b) a heavy chain variable domain comprising a sequence with at least 95% identity to SEQ ID NO: 63 and a light chain variable domain comprising a sequence with at least 95% identity to SEQ ID NO: 64;
  (c) a heavy chain variable domain comprising a sequence with at least 95% identity to SEQ ID NO: 53 and a light chain variable domain comprising a sequence with at least 95% identity to SEQ ID NO: 54; or
  (d) a heavy chain variable domain comprising a sequence with at least 95% identity to SEQ ID NO: 39 and a light chain variable domain comprising a sequence with at least 95% identity to SEQ ID NO: 40.

20. The anti-KRAS antibody or antigen-binding fragment thereof of claim 17, wherein the anti-KRAS antibody or antigen-binding fragment thereof comprises:
  a heavy chain variable domain comprising a heavy chain CDR set (CDR1, CDR2, and CDR3) of the sequences of SEQ ID NO: 189, 190, and 191;
  a light chain variable domain comprising a light chain CDR set (CDR1, CDR2, and CDR3) of the sequences of SEQ ID NO: 192, 193, and 194;
  a heavy chain variable domain comprising a sequence with at least 95% identity to SEQ ID NO: 39; and
  a light chain variable domain comprising a sequence with at least 95% identity to SEQ ID NO: 40.

* * * * *

SEQUENCE LISTING

<160> NUMBER OF SEQ ID NOS: 318

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Asn Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

```
Ala Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Ala His Trp Val Phe Gly Gly Gly Thr Lys Leu Thr Val Leu
            100                 105                 110

<210> SEQ ID NO 3
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Glu Ser Gly Gly Gly Val Val Gln Pro Gly Arg
 1               5                  10                  15

Ser Leu Arg Leu Ser Cys Thr Asn Ser Gly Phe Ser Phe Ser Gly Tyr
                 20                  25                  30

Ala Met His Trp Val Arg Gln Ala Pro Gly Lys Gly Leu Glu Trp Val
            35                  40                  45

Ala Val Ile Ser Phe Asp Gly Ser His Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu His Met Asn Ser Leu Arg Ala Glu Asp Thr Ala Val Tyr Tyr Cys
                 85                  90                  95

Ala Ser Gly Gly Asn Tyr Tyr Gly Ser Gly Thr Ile Val Ser His Gly
            100                 105                 110

Leu Asp Phe Trp Gly Gln Gly Thr Thr Val Thr Val Ser Ser
        115                 120                 125

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Val Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Asp Asp Phe Ala Ala Tyr Tyr Cys Gln His Tyr Asn Ser Tyr Pro Tyr
                 85                  90                  95

Thr Phe Gly Gln Gly Thr Lys Leu Glu Ile Lys
            100                 105

<210> SEQ ID NO 5
```

<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Glu Ser Gly Gly Gly Val Val Gln Pro Gly Arg
1               5                   10                  15

Ser Leu Arg Leu Ser Cys Thr Asn Ser Gly Phe Ser Phe Ser Gly Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Ser Gly Gly Asn Tyr Tyr Gly Ser Gly Thr Ile Val Ser His Gly
            100                 105                 110

Met Asp Val Trp Gly Gln Gly Thr Thr Val Thr Val Ser Ser
        115                 120                 125

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Arg Gly Gly Gly Thr Lys Leu Thr Val Leu
            100                 105

<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ser Asn Ser Gly Phe Ser Phe Ser Gly Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Lys Met His Tyr Gly Ser Gly Ala Tyr His Phe Asp Leu Trp
            100                 105                 110

Gly Gln Gly Thr Leu Val Thr Val Ser Ser
            115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Phe
                85                  90                  95

Thr Phe Gly Pro Gly Thr Lys Val Asp Ile Lys
            100                 105

<210> SEQ ID NO 9
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Leu Glu Ser Gly Gly Val Val Gln Pro Gly Arg
1               5                   10                  15

Ser Leu Arg Leu Ser Cys Thr Asn Ser Gly Phe Ser Phe Ser Gly Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu His Met Asn Ser Leu Thr Ala Glu Asp Thr Ala Val Tyr Tyr Cys
                85                  90                  95

Ala Ser Gly Gly Asn Tyr Tyr Gly Ser Gly Thr Ile Val Ser His Gly
            100                 105                 110

Met Asp Val Trp Gly Gln Gly Thr Thr Val Thr Val Ser Ser
        115                 120                 125

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu
            100                 105                 110

<210> SEQ ID NO 11
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Leu Glu Pro Gly Gly Val Val Gln Pro Gly Arg
1               5                   10                  15

Ser Leu Arg Leu Ser Cys Thr Asn Ser Gly Phe Ser Phe Ser Gly Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Ser Gly Gly Asn Tyr Tyr Gly Ser Gly Thr Ile Val Ser His Gly
            100                 105                 110

Met Asp Val Trp Gly Gln Gly Thr Thr Val Thr Val Ser Ser
        115                 120                 125

<210> SEQ ID NO 12
<211> LENGTH: 110
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asn Val Gly Gly Tyr
            20                  25                  30

Asn His Val Ser Trp Tyr Gln Gln His Pro Gly Lys Ala Pro Lys Val
        35                  40                  45

Ile Ile Tyr Asp Val Asn Lys Arg Pro Ser Gly Val Ser His Arg Phe
    50                  55                  60

Ser Gly Ser Lys Ser Ala Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Ser Thr Tyr Val Phe Gly Thr Gly Thr Lys Leu Thr Val Leu
            100                 105                 110

<210> SEQ ID NO 13
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Ala Gly Gly Val Val Gln Pro Gly Arg
1               5                   10                  15

Ser Leu Arg Leu Ser Cys Thr Asn Ser Gly Phe Ser Phe Ser Gly Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Thr Ala Glu Asp Thr Ala Val Tyr Tyr Cys
                85                  90                  95

Ala Ser Gly Gly Asn Tyr Tyr Gly Ser Gly Thr Ile Val Ser His Gly
            100                 105                 110

Met Asp Val Trp Gly Gln Gly Thr Thr Val Thr Val Ser Ser
        115                 120                 125

<210> SEQ ID NO 14
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
```

```
                 20                  25                  30

Lys Tyr Val Ser Trp Tyr Gln Gln Tyr Pro Gly Lys Ala Pro Lys Leu
                 35                  40                  45

Met Ile Tyr Asp Val Ser Lys Arg Pro Ser Gly Val Ser Asn Arg Phe
             50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Asn Ser Tyr Thr Ser Ser
                 85                  90                  95

Arg Ile Tyr Val Phe Gly Thr Gly Thr Lys Leu Thr Val Leu
                100                 105                 110

<210> SEQ ID NO 15
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Leu Glu Pro Gly Gly Gly Val Val Gln Pro Gly Arg
 1               5                  10                  15

Ser Leu Arg Leu Ser Cys Thr Asn Ser Gly Phe Ser Phe Ser Gly Tyr
                 20                  25                  30

Ala Met His Trp Val Arg Gln Ala Pro Gly Lys Gly Leu Glu Trp Val
             35                  40                  45

Ala Val Ile Ser Phe Asp Gly Ser His Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu His Met Asn Ser Leu Arg Ala Glu Asp Thr Ala Val Tyr Tyr Cys
                 85                  90                  95

Ala Ser Gly Gly Asn Tyr Tyr Gly Ser Gly Thr Ile Val Ser His Gly
                100                 105                 110

Met Asp Val Trp Gly Gln Gly Thr Thr Val Thr Val Ser Ser
             115                 120                 125

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ser Val Leu Thr Gln Pro Ala Ser Val Ser Gly Ser Pro Gly Gln
 1               5                  10                  15

Ser Ile Thr Ile Ser Cys Thr Gly Thr Ser Asn Asp Ile Gly Ala Tyr
                 20                  25                  30

Asn Tyr Val Ser Trp Tyr Gln Gln His Pro Gly Lys Ala Pro Lys Leu
                 35                  40                  45

Met Ile Tyr Asp Val Asn Arg Pro Ser Gly Val Pro Asp Arg Phe
             50                  55                  60

Ser Gly Ser Lys Ser Gly Asn Met Ala Ser Leu Thr Ile Ser Gly Leu
 65                  70                  75                  80

Gln Ala Glu Asp Asp Ala Asp Tyr Tyr Cys Ser Ser Tyr Thr Ser Ser
```

```
                    85                  90                  95
Ser Thr Leu Val Val Phe Gly Gly Gly Thr Lys Leu Thr Val Leu
                100                 105                 110

<210> SEQ ID NO 17
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Gly Val Val Gln Pro Gly Arg
1               5                   10                  15

Ser Leu Arg Leu Ser Cys Thr Asn Ser Gly Phe Ser Phe Ser Gly Tyr
                20                  25                  30

Ala Met His Trp Val Arg Gln Ala Pro Gly Lys Gly Leu Glu Trp Val
            35                  40                  45

Ala Val Ile Ser Phe Asp Gly Ser His Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu His Met Asn Ser Val Arg Ala Glu Asp Thr Ala Val Tyr Tyr Cys
                85                  90                  95

Ala Ser Gly Gly Asn His Tyr Gly Ser Gly Thr Ile Val Ser His Gly
                100                 105                 110

Met Asp Val Arg Gly Gln Gly Thr Thr Val Thr Val Ser Ser
            115                 120                 125

<210> SEQ ID NO 18
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Ser
                20                  25                  30

Asn Trp Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Leu Thr Val Leu
                100                 105                 110

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 19

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Asp Gly Gly Ser Tyr Phe Asp Tyr Trp Gly Gln Gly
            100                 105                 110

Thr Leu Val Thr Val Ser Ser
        115

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Val Thr Val Leu
            100                 105                 110

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Leu Asn
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
            50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
            115

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Tyr Gly
                85                  90                  95

Ser Thr His Trp Val Phe Gly Gly Gly Thr Lys Leu Thr Val Leu
            100                 105                 110

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Arg Gln Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

```
Val Thr Val Ser Ser
        115

<210> SEQ ID NO 24
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Gly Arg
                85                  90                  95

Lys Val His Trp Val Phe Gly Gly Gly Thr Lys Leu Thr Val Leu
            100                 105                 110

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Thr Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 26
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 26

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Arg
                85                  90                  95

Thr Thr His Trp Val Phe Gly Gly Gly Thr Lys Leu Thr Val Leu
            100                 105                 110

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Arg Pro Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

```
Ile Phe Glu Asp Asn Gln Arg Pro Ser Gly Ile Pro Asp Arg Phe Ser
 50                  55                  60

Ala Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Phe His
                 85                  90                  95

Ser Glu His Trp Val Phe Gly Gly Gly Thr Lys Leu Thr Val Leu
                100                 105                 110

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Ser Ala Thr Tyr
             20                  25                  30

Gly Met His Trp Val Arg Gln Ala Pro Gly Lys Gly Leu Glu Trp Val
         35                  40                  45

Ala Val Ile Ser His Asp Gly Ser Lys Lys Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Val Gln Leu Ser Ser Leu Arg Pro Glu Asp Thr Ala Val Tyr Tyr Cys
                 85                  90                  95

Ala Thr Ser Leu Tyr Ser Ser Met Asp Leu Trp Gly Gln Gly Thr Thr
                100                 105                 110

Val Thr Val Ser Ser
            115

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Ser Val Val Thr Gln Pro Pro Ser Val Ser Ala Ala Pro Gly Gln
 1               5                  10                  15

Lys Val Thr Ile Ser Cys Ser Gly Ser Asn Ser Asn Ile Gly Lys Asn
             20                  25                  30

Tyr Val Ser Trp Phe Gln Gln Val Pro Gly Thr Ala Pro Lys Leu Leu
         35                  40                  45

Ile Phe Glu Asp Asn Gln Arg Pro Ser Gly Ile Pro Asp Arg Phe Ser
 50                  55                  60

Ala Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Ser
                 85                  90                  95

Asp Thr His Trp Val Phe Gly Gly Gly Thr Lys Leu Thr Val Leu
                100                 105                 110
```

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Phe His
                20                  25                  30

Gly Met His Trp Val Arg Gln Ala Pro Gly Lys Gly Leu Glu Trp Val
            35                  40                  45

Ala Val Ile Ser His Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
                20                  25                  30

Tyr Val Ser Trp Phe Gln Gln Val Pro Gly Thr Ala Pro Lys Leu Leu
            35                  40                  45

Ile Phe Glu Asp Asn Gln Arg Pro Ser Gly Ile Pro Asp Arg Phe Ser
        50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Gly
                85                  90                  95

Asp Val His Trp Val Phe Gly Gly Gly Thr Lys Leu Thr Val Leu
            100                 105                 110

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Gln Ser Gly Gly Gly Val Val Gln Pro Gly Arg

```
                1               5                   10                  15
Ser Leu Arg Leu Ser Cys Ala Ala Ser Gly Phe Thr Ser Arg His Pro
                20                  25                  30

Gly Met His Trp Val Arg Gln Ala Pro Gly Lys Gly Leu Glu Trp Val
            35                  40                  45

Ala Val Ile Ser His Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
                100                 105                 110

Val Thr Val Ser Ser
            115
```

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Tyr Arg
                85                  90                  95

Gly Pro His Trp Val Phe Gly Gly Gly Thr Lys Leu Thr Val Leu
                100                 105                 110
```

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Arg His Pro
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Phe
```

```
                65                  70                  75                  80
Val Gln Leu Ser Ser Leu Arg Pro Glu Asp Thr Ala Val Tyr Tyr Cys
                    85                  90                  95

Ala Thr Ser Leu Tyr Ser Ser Met Asp Leu Trp Gly Gln Gly Thr Thr
                100                 105                 110

Val Thr Val Ser Ser
        115

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
                20                  25                  30

Tyr Val Ser Trp Phe Gln Gln Val Pro Gly Thr Ala Pro Lys Leu Leu
            35                  40                  45

Ile Phe Glu Asp Asn Gln Arg Pro Ser Gly Ile Pro Asp Arg Phe Ser
50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Tyr Arg
                85                  90                  95

Gly Pro His Trp Val Phe Gly Gly Gly Thr Lys Leu Thr Val Leu
            100                 105                 110

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Arg Ala Pro
                20                  25                  30

Gly Met His Trp Val Arg Gln Ala Pro Gly Lys Gly Leu Glu Trp Val
            35                  40                  45

Ala Val Ile Ser His Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
                100                 105                 110

Val Thr Val Ser Ser
        115
```

```
<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp His Asn
                85                  90                  95

Gly Glu His Trp Val Phe Gly Gly Gly Thr Lys Leu Thr Val Leu
            100                 105                 110

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Arg His Pro
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Ser Val Val Thr Gln Pro Pro Ser Val Ser Ala Ala Pro Gly Gln
1               5                   10                  15
```

```
Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
 50                  55                  60

Ala Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Lys Phe
                 85                  90                  95

Gly Val His Trp Val Phe Gly Gly Gly Thr Lys Leu Thr Val Leu
            100                 105                 110
```

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Ser Arg Lys Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Val Gln Leu Ser Ser Leu Arg Pro Glu Asp Thr Ala Val Tyr Tyr Cys
                 85                  90                  95

Ala Thr Ser Leu Tyr Ser Ser Met Asp Leu Trp Gly Gln Gly Thr Thr
            100                 105                 110

Val Thr Val Ser Ser
        115
```

<210> SEQ ID NO 42
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Gln Ser Val Val Thr Gln Pro Pro Ser Val Ser Ala Ala Pro Gly Gln
 1               5                  10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
 50                  55                  60

Ala Ser Lys Ser Gly Thr Ser Ala Ser Leu Ala Ile Ser Gly Leu Gln
 65                  70                  75                  80
```

Ser Glu Asp Glu Ala Asp Tyr Tyr Cys Ala Ala Trp Asp Ser Pro
            85                  90                  95

Thr Ile His Trp Val Phe Gly Gly Gly Thr Lys Leu Thr Val Leu
        100                 105                 110

<210> SEQ ID NO 43
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Gln Ser Gly Gly Val Val Gln Pro Gly Arg
1               5                   10                  15

Ser Leu Arg Leu Ser Cys Ala Ala Ser Gly Phe Thr Ser His Asn Lys
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
            85                  90                  95

Ala Thr Ser Leu Tyr Ser Ser Met Asp Leu Trp Gly Gln Gly Thr Thr
        100                 105                 110

Val Thr Val Ser Ser
        115

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Ser Val Val Thr Gln Pro Pro Ser Val Ser Ala Ala Pro Gly Gln
1               5                   10                  15

Lys Val Thr Ile Ser Cys Ser Gly Ser Asn Phe Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Phe Ala
            85                  90                  95

Gly Val His Trp Val Phe Gly Gly Gly Thr Lys Leu Thr Val Leu
        100                 105                 110

<210> SEQ ID NO 45
<211> LENGTH: 117
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 45

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Tyr Lys Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Ser Ser Leu Tyr Ser Ser Met Asp Leu Trp Gly Gln Gly Thr Thr
            100                 105                 110

Val Thr Val Ser Ser
        115

<210> SEQ ID NO 46
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Phe
                85                  90                  95

Ser Glu His Trp Val Phe Gly Gly Gly Thr Lys Leu Thr Val Leu
            100                 105                 110

<210> SEQ ID NO 47
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Arg Ala Pro
            20                  25                  30
```

Gly Met His Trp Val Arg Gln Ala Pro Gly Lys Gly Leu Glu Trp Val
            35                  40                  45

Ala Val Ile Ser His Asp Gly Ser Lys Lys Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Val Gln Leu Ser Ser Leu Arg Pro Glu Asp Thr Ala Val Tyr Tyr Cys
                 85                  90                  95

Ala Thr Ser Leu Tyr Ser Ser Met Asp Leu Trp Gly Gln Gly Thr Thr
                100                 105                 110

Val Thr Val Ser Ser
            115

<210> SEQ ID NO 48
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Ser Val Val Thr Gln Pro Pro Ser Val Ser Ala Ala Pro Gly Gln
 1               5                  10                  15

Lys Val Thr Ile Ser Cys Ser Gly Ser Asn Ser Asn Ile Gly Lys Asn
             20                  25                  30

Tyr Val Ser Trp Phe Gln Gln Val Pro Gly Thr Ala Pro Lys Leu Leu
         35                  40                  45

Ile Phe Glu Asp Asn Gln Arg Pro Ser Gly Ile Pro Asp Arg Phe Ser
 50                  55                  60

Ala Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Gln Asn
                 85                  90                  95

Gly Val His Trp Val Phe Gly Gly Gly Thr Lys Leu Thr Val Leu
                100                 105                 110

<210> SEQ ID NO 49
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Ser Arg Ser Pro
             20                  25                  30

Gly Met His Trp Val Arg Gln Ala Pro Gly Lys Gly Leu Glu Trp Val
         35                  40                  45

Ala Val Ile Ser His Asp Gly Ser Lys Lys Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Val Gln Leu Ser Ser Leu Arg Pro Glu Asp Thr Ala Val Tyr Tyr Cys
                 85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 50
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Leu Arg
                85                  90                  95

Gly Val His Trp Val Phe Gly Gly Gly Thr Lys Leu Thr Val Leu
            100                 105                 110

<210> SEQ ID NO 51
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Arg His His
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 52
<211> LENGTH: 111
<212> TYPE: PRT
<213> ORGANISM: Artificial Sequence
<220> FEATURE:

<223> OTHER INFORMATION: Description of Artificial Sequence: Synthetic
       polypeptide

<400> SEQUENCE: 52

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Arg His
                85                  90                  95

Gly Thr His Trp Val Phe Gly Gly Gly Thr Lys Leu Thr Val Leu
            100                 105                 110

<210> SEQ ID NO 53
<211> LENGTH: 117
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 53

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Arg Asn Pro
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 54

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu

```
                35                  40                  45
Ile Phe Glu Asp Asn Gln Arg Pro Ser Gly Ile Pro Asp Arg Phe Ser
 50                  55                  60
Ala Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Thr
                 85                  90                  95
Gly Val His Trp Val Phe Gly Gly Gly Thr Lys Leu Thr Val Leu
            100                 105                 110

<210> SEQ ID NO 55
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Gln Ser Gly Gly Gly Val Val Gln Pro Gly Arg
 1               5                  10                  15
Ser Leu Arg Leu Ser Cys Ala Ala Ser Gly Phe Thr Arg Thr Tyr
             20                  25                  30
Gly Met His Trp Val Arg Gln Ala Pro Gly Lys Gly Leu Glu Trp Val
         35                  40                  45
Ala Val Ile Ser His Asp Gly Ser Lys Lys Tyr Tyr Ala Asp Ser Val
 50                  55                  60
Lys Gly Arg Phe Thr Ile Ser Arg Asp Asn Ser Lys Asn Thr Leu Phe
 65                  70                  75                  80
Val Gln Leu Ser Ser Leu Arg Pro Glu Asp Thr Ala Val Tyr Tyr Cys
                 85                  90                  95
Ala Thr Ser Leu Tyr Ser Ser Met Asp Leu Trp Gly Gln Gly Thr Thr
            100                 105                 110
Val Thr Val Ser Ser
        115

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Ser Val Val Thr Gln Pro Pro Ser Val Ser Ala Ala Pro Gly Gln
 1               5                  10                  15
Lys Val Thr Ile Ser Cys Ser Gly Ser Asn Ser Asn Ile Gly Lys Asn
             20                  25                  30
Tyr Val Ser Trp Phe Gln Gln Val Pro Gly Thr Ala Pro Lys Leu Leu
         35                  40                  45
Ile Phe Glu Asp Asn Gln Arg Pro Ser Gly Ile Pro Asp Arg Phe Ser
 50                  55                  60
Ala Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Leu Pro
                 85                  90                  95
Thr Asp His Trp Val Phe Gly Gly Gly Thr Lys Leu Thr Val Leu
```

<210> SEQ ID NO 57
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Arg Gln Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Tyr Ser
                85                  90                  95

Gly Val His Trp Val Phe Gly Gly Gly Thr Lys Leu Thr Val Leu
            100                 105                 110

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Pro Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
            115

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Asn Pro
                85                  90                  95

Arg Asp His Trp Val Phe Gly Gly Gly Thr Lys Leu Thr Val Leu
            100                 105                 110

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Lys Pro
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60
```

```
Lys Gly Arg Phe Thr Ile Ser Arg Asp Asn Ser Lys Asn Thr Leu Phe
 65                  70                  75                  80

Val Gln Leu Ser Ser Leu Arg Pro Glu Asp Thr Ala Val Tyr Tyr Cys
                 85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ser Val Val Thr Gln Pro Pro Ser Val Ser Ala Ala Pro Gly Gln
 1               5                  10                  15

Lys Val Thr Ile Ser Cys Ser Gly Ser Asn Ser Asn Ile Gly Lys Asn
                20                  25                  30

Tyr Val Ser Trp Phe Gln Gln Val Pro Gly Thr Ala Pro Lys Leu Leu
            35                  40                  45

Ile Phe Glu Asp Asn Gln Arg Pro Ser Gly Ile Pro Asp Arg Phe Ser
 50                  55                  60

Ala Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Leu Arg
                 85                  90                  95

Gly Val His Trp Val Phe Gly Gly Gly Thr Lys Leu Thr Val Leu
            100                 105                 110

<210> SEQ ID NO 63
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Ser Lys Lys Tyr
                20                  25                  30

Gly Met His Trp Val Arg Gln Ala Pro Gly Lys Gly Leu Glu Trp Val
            35                  40                  45

Ala Val Ile Ser His Asp Gly Ser Lys Lys Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Val Gln Leu Ser Ser Leu Arg Pro Glu Asp Thr Ala Val Tyr Tyr Cys
                 85                  90                  95

Ala Thr Ser Leu Tyr Ser Ser Met Asp Leu Trp Gly Gln Gly Thr Thr
            100                 105                 110

Val Thr Val Ser Ser
        115
```

<210> SEQ ID NO 64
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Leu Gly
                85                  90                  95

Gly Asp His Trp Val Phe Gly Gly Gly Thr Lys Leu Thr Val Leu
            100                 105                 110

<210> SEQ ID NO 65
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Thr Leu Pro
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 66
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Ala
                85                  90                  95

Gly Val His Trp Val Phe Gly Gly Gly Thr Lys Leu Thr Val Leu
            100                 105                 110

<210> SEQ ID NO 67
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Lys Met Pro
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 68
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
50                  55                  60
```

Ala Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Glu His
                 85                  90                  95

Gly Val His Trp Val Phe Gly Gly Gly Thr Lys Leu Thr Val Leu
            100                 105                 110

<210> SEQ ID NO 69
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Asn Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Ala Ser Leu Tyr Ser Ser Met Asp Leu Trp Gly Gln Gly Thr Thr
            100                 105                 110

Val Thr Val Ser Ser
        115

<210> SEQ ID NO 70
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Ala His Trp Val Phe Gly Gly Gly Thr Lys Leu Thr Val Leu
            100                 105                 110

<210> SEQ ID NO 71
<211> LENGTH: 117

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Asn Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Met Val Ser Ser Met Asp Leu Trp Gly Gln Gly Thr Thr
            100                 105                 110

Val Thr Val Ser Ser
        115

<210> SEQ ID NO 72
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Thr His Trp Val Phe Gly Gly Thr Lys Leu Thr Val Leu
            100                 105                 110

<210> SEQ ID NO 73
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Asn Tyr
```

```
                20                  25                  30
Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Met Arg Ser Ser Met Asp Leu Trp Gly Gln Gly Thr Thr
            100                 105                 110

Val Thr Val Ser Ser
        115

<210> SEQ ID NO 74
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Ala His Trp Val Phe Gly Gly Gly Thr Lys Leu Thr Val Leu
            100                 105                 110

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Phe Thr Ser Ser Asn Tyr Gly Met His
1               5                   10

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Val Ile Ser His Asp Gly Ser Lys Lys Tyr Tyr Ala Asp Ser Val Lys
1               5                   10                  15
```

Gly

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Leu Tyr Ser Ser Met Asp Leu
1               5

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Gly Ser Asn Ser Asn Ile Gly Lys Asn Tyr Val Ser
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Asp Asn Gln Arg Pro Ser
1               5

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Ala Trp Asp Asp Ser Leu Asn Ala His Trp Val
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Phe Ser Phe Ser Gly Tyr Ala Met His
1               5                   10

<210> SEQ ID NO 82
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 82

Val Ile Ser Phe Asp Gly Ser His Lys Tyr Tyr Ala Asp Ser Val Lys
1               5                   10                  15
Gly

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Gly Asn Tyr Tyr Gly Ser Gly Thr Ile Val Ser His Gly Leu Asp
1               5                   10                  15
Phe

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ala Ser Gln Ser Ile Ser Ser Trp Leu Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Ala Ser Ser Leu Glu Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln His Tyr Asn Ser Tyr Pro Tyr Thr
1               5

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Gly Phe Ser Phe Ser Gly Tyr Ala Met His
1               5                   10

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Ile Ser Phe Asp Gly Ser His Lys Tyr Tyr Ala Asp Ser Val Lys
1               5                   10                  15

Gly

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gly Asn Tyr Tyr Gly Ser Gly Thr Ile Val Ser His Gly Met Asp
1               5                   10                  15

Val

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Gly Asp Ser Leu Arg Ser Tyr Tyr Ala Ser
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Lys Asn Asn Arg Pro Ser
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asn Ser Arg Asp Ser Ser Gly Asn His
1               5

<210> SEQ ID NO 93
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Phe Ser Phe Ser Gly Tyr Thr Met His
1               5                   10

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Val Ile Ser Phe Asp Gly Ser His Lys Tyr Tyr Ala Asp Ser Val Lys
1               5                   10                  15

Gly

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Lys Met His Tyr Gly Ser Gly Ala Tyr His Phe Asp Leu
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ala Ser Gln Ser Ile Ser Asn Tyr Leu Asn
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Ala Ser Ser Leu Gln Ser
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 98

Gln Gln Ser Tyr Ser Ser Pro Phe Thr
1               5

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Phe Ser Phe Ser Gly Tyr Ala Met His
1               5                   10

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Val Ile Ser Phe Asp Gly Ser His Lys Tyr Tyr Ala Asp Ser Val Lys
1               5                   10                  15

Gly

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Asn Tyr Tyr Gly Ser Gly Thr Ile Val Ser His Gly Met Asp
1               5                   10                  15

Val

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Gly Thr Ser Ser Asp Val Gly Gly Tyr Asn Tyr Val Ser
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Val Ser Asn Arg Pro Ser
1               5
```

```
<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ser Tyr Thr Ser Ser Ser Thr Leu Val Val
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Phe Ser Phe Ser Gly Tyr Ala Met His
1               5                   10

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Val Ile Ser Phe Asp Gly Ser His Lys Tyr Tyr Ala Asp Ser Val Lys
1               5                   10                  15

Gly

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Gly Asn Tyr Tyr Gly Ser Gly Thr Ile Val Ser His Gly Met Asp
1               5                   10                  15

Val

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Thr Gly Thr Ser Ser Asn Val Gly Gly Tyr Asn His Val Ser
1               5                   10

<210> SEQ ID NO 109
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 109

Asp Val Asn Lys Arg Pro Ser
1               5

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Ser Tyr Thr Thr Ser Ser Thr Tyr Val
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Phe Ser Phe Ser Gly Tyr Ala Met His
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Val Ile Ser Phe Asp Gly Ser His Lys Tyr Tyr Ala Asp Ser Val Lys
1               5                   10                  15

Gly

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gly Asn Tyr Tyr Gly Ser Gly Thr Ile Val Ser His Gly Met Asp
1               5                   10                  15

Val

<210> SEQ ID NO 114
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114
```

```
Thr Gly Thr Ser Ser Asp Val Gly Gly Tyr Lys Tyr Val Ser
1               5                   10
```

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Asp Val Ser Lys Arg Pro Ser
1               5
```

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

```
Asn Ser Tyr Thr Ser Ser Arg Ile Tyr Val
1               5                   10
```

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Gly Phe Ser Phe Ser Gly Tyr Ala Met His
1               5                   10
```

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Val Ile Ser Phe Asp Gly Ser His Lys Tyr Tyr Ala Asp Ser Val Lys
1               5                   10                  15

Gly
```

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Gly Gly Asn Tyr Tyr Gly Ser Gly Thr Ile Val Ser His Gly Met Asp
1               5                   10                  15

Val
```

```
<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Gly Thr Ser Asn Asp Ile Gly Ala Tyr Asn Tyr Val Ser
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Val Asn Asn Arg Pro Ser
1               5

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Ser Tyr Thr Ser Ser Ser Thr Leu Val Val
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Phe Ser Phe Ser Gly Tyr Ala Met His
1               5                   10

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Val Ile Ser Phe Asp Gly Ser His Lys Tyr Tyr Ala Asp Ser Val Lys
1               5                   10                  15

Gly

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 125

Gly Gly Asn His Tyr Gly Ser Gly Thr Ile Val Ser His Gly Met Asp
1               5                   10                  15
Val

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Gly Thr Ser Ser Asp Ile Gly Gly Ser Asn Trp Val Ser
1               5                   10

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Val Ser Lys Arg Pro Ser
1               5

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Ser Tyr Thr Ser Ser Ser Thr Tyr Val
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Phe Thr Phe Ser Ser Tyr Trp Met Ser
1               5                   10

<210> SEQ ID NO 130
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Phe Ile Arg Ser Lys Ala Tyr Gly Gly Thr Thr Glu Tyr Ala Ala Ser
1               5                   10                  15
Val Lys Gly

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Gly Gly Ser Tyr Phe Asp Tyr
1               5

<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Thr Gly Thr Ser Ser Asp Val Gly Gly Tyr Asn Tyr Val Ser
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Val Ser Lys Arg Pro Ser
1               5

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Ser Tyr Thr Ser Ser Ser Thr Tyr Val
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Phe Thr Ser Ser Leu Asn Gly Met His
1               5                   10

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Val Ile Ser His Asp Gly Ser Lys Lys Tyr Tyr Ala Asp Ser Val Lys
1               5                   10                  15
Gly

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Leu Tyr Ser Ser Met Asp Leu
1               5

<210> SEQ ID NO 138
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Gly Ser Asn Ser Asn Ile Gly Lys Asn Tyr Val Ser
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Glu Asp Asn Gln Arg Pro Ser
1               5

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ala Trp Asp Asp Tyr Gly Ser Thr His Trp Val
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Phe Thr Ser Arg Gln Tyr Gly Met His
1               5                   10

```
<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Val Ile Ser His Asp Gly Ser Lys Lys Tyr Tyr Ala Asp Ser Val Lys
1               5                   10                  15

Gly

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Leu Tyr Ser Ser Met Asp Leu
1               5

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Gly Ser Asn Ser Asn Ile Gly Lys Asn Tyr Val Ser
1               5                   10

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Glu Asp Asn Gln Arg Pro Ser
1               5

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Ala Trp Asp Asp Gly Arg Lys Val His Trp Val
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 147

Gly Phe Thr Ser Ser Thr Tyr Gly Met His
1               5                   10

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Val Ile Ser His Asp Gly Ser Lys Lys Tyr Tyr Ala Asp Ser Val Lys
1               5                   10                  15

Gly

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Leu Tyr Ser Ser Met Asp Leu
1               5

<210> SEQ ID NO 150
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ser Gly Ser Asn Ser Asn Ile Gly Lys Asn Tyr Val Ser
1               5                   10

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Glu Asp Asn Gln Arg Pro Ser
1               5

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Ala Trp Asp Asp Ser Arg Thr Thr His Trp Val
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Phe Thr Ser Arg Pro Tyr Gly Met His
1               5                   10

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Val Ile Ser His Asp Gly Ser Lys Lys Tyr Tyr Ala Asp Ser Val Lys
1               5                   10                  15

Gly

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Leu Tyr Ser Ser Met Asp Leu
1               5

<210> SEQ ID NO 156
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ser Gly Ser Asn Ser Asn Ile Gly Lys Asn Tyr Val Ser
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Asp Asn Gln Arg Pro Ser
1               5

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Ala Trp Asp Asp Phe His Ser Glu His Trp Val
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Phe Thr Ser Ala Thr Tyr Gly Met His
1               5                   10

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Val Ile Ser His Asp Gly Ser Lys Lys Tyr Tyr Ala Asp Ser Val Lys
1               5                   10                  15

Gly

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Leu Tyr Ser Ser Met Asp Leu
1               5

<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Gly Ser Asn Ser Asn Ile Gly Lys Asn Tyr Val Ser
1               5                   10

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Asp Asn Gln Arg Pro Ser
1               5

```
<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ala Ala Trp Asp Asp Ser Ser Asp Thr His Trp Val
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Phe Thr Ser Ser Phe His Gly Met His
1               5                   10

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Val Ile Ser His Asp Gly Ser Lys Lys Tyr Tyr Ala Asp Ser Val Lys
1               5                   10                  15

Gly

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Leu Tyr Ser Ser Met Asp Leu
1               5

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ser Gly Ser Asn Ser Asn Ile Gly Lys Asn Tyr Val Ser
1               5                   10

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 169

Glu Asp Asn Gln Arg Pro Ser
1               5

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Ala Trp Asp Asp Ser Gly Asp Val His Trp Val
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Phe Thr Ser Arg His Pro Gly Met His
1               5                   10

<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Val Ile Ser His Asp Gly Ser Lys Lys Tyr Tyr Ala Asp Ser Val Lys
1               5                   10                  15

Gly

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Leu Tyr Ser Ser Met Asp Leu
1               5

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Gly Ser Asn Ser Asn Ile Gly Lys Asn Tyr Val Ser
1               5                   10

```
<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Glu Asp Asn Gln Arg Pro Ser
1               5

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Ala Trp Asp Asp Tyr Arg Gly Pro His Trp Val
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Phe Thr Ser Arg His Pro Gly Met His
1               5                   10

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Val Ile Ser His Asp Gly Ser Lys Lys Tyr Tyr Ala Asp Ser Val Lys
1               5                   10                  15

Gly

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Leu Tyr Ser Ser Met Asp Leu
1               5

<210> SEQ ID NO 180
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 180

Ser Gly Ser Asn Ser Asn Ile Gly Lys Asn Tyr Val Ser
1               5                   10

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Glu Asp Asn Gln Arg Pro Ser
1               5

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ala Ala Trp Asp Asp Tyr Arg Gly Pro His Trp Val
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Phe Thr Ser Arg Ala Pro Gly Met His
1               5                   10

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Val Ile Ser His Asp Gly Ser Lys Lys Tyr Tyr Ala Asp Ser Val Lys
1               5                   10                  15

Gly

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Leu Tyr Ser Ser Met Asp Leu
1               5
```

```
<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Gly Ser Asn Ser Asn Ile Gly Lys Asn Tyr Val Ser
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Glu Asp Asn Gln Arg Pro Ser
1               5

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Ala Trp Asp Asp His Asn Gly Glu His Trp Val
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Phe Thr Ser Arg His Pro Gly Met His
1               5                   10

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Val Ile Ser His Asp Gly Ser Lys Lys Tyr Tyr Ala Asp Ser Val Lys
1               5                   10                  15

Gly

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 191

Ser Leu Tyr Ser Ser Met Asp Leu
1               5

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Gly Ser Asn Ser Asn Ile Gly Lys Asn Tyr Val Ser
1               5                   10

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Glu Asp Asn Gln Arg Pro Ser
1               5

<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Ala Trp Asp Asp Lys Phe Gly Val His Trp Val
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Phe Thr Ser Arg Lys Tyr Gly Met His
1               5                   10

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Val Ile Ser His Asp Gly Ser Lys Lys Tyr Tyr Ala Asp Ser Val Lys
1               5                   10                  15
Gly
```

```
<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Leu Tyr Ser Ser Met Asp Leu
1               5

<210> SEQ ID NO 198
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Gly Ser Asn Ser Asn Ile Gly Lys Asn Tyr Val Ser
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Glu Asp Asn Gln Arg Pro Ser
1               5

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Ala Trp Asp Asp Ser Pro Thr Ile His Trp Val
1               5                   10

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Phe Thr Ser His Asn Lys Gly Met His
1               5                   10

<210> SEQ ID NO 202
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202
```

```
Val Ile Ser His Asp Gly Ser Lys Lys Tyr Tyr Ala Asp Ser Val Lys
1               5                   10                  15

Gly

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Leu Tyr Ser Ser Met Asp Leu
1               5

<210> SEQ ID NO 204
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Gly Ser Asn Phe Asn Ile Gly Lys Asn Tyr Val Ser
1               5                   10

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Glu Asp Asn Gln Arg Pro Ser
1               5

<210> SEQ ID NO 206
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ala Ala Trp Asp Asp Phe Ala Gly Val His Trp Val
1               5                   10

<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Phe Thr Ser Tyr Lys Tyr Gly Met His
1               5                   10

<210> SEQ ID NO 208
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Val Ile Ser His Asp Gly Ser Lys Lys Tyr Tyr Ala Asp Ser Val Lys
1               5                   10                  15

Gly

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Leu Tyr Ser Ser Met Asp Leu
1               5

<210> SEQ ID NO 210
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ser Gly Ser Asn Ser Asn Ile Gly Lys Asn Tyr Val Ser
1               5                   10

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Glu Asp Asn Gln Arg Pro Ser
1               5

<210> SEQ ID NO 212
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Ala Trp Asp Asp Ser Phe Ser Glu His Trp Val
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213
```

```
Gly Phe Thr Ser Arg Ala Pro Gly Met His
1               5                   10

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Val Ile Ser His Asp Gly Ser Lys Lys Tyr Tyr Ala Asp Ser Val Lys
1               5                   10                  15

Gly

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Leu Tyr Ser Ser Met Asp Leu
1               5

<210> SEQ ID NO 216
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Gly Ser Asn Ser Asn Ile Gly Lys Asn Tyr Val Ser
1               5                   10

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Glu Asp Asn Gln Arg Pro Ser
1               5

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ala Ala Trp Asp Asp Gln Asn Gly Val His Trp Val
1               5                   10

<210> SEQ ID NO 219
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Phe Thr Ser Arg Ser Pro Gly Met His
1               5                   10

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Val Ile Ser His Asp Gly Ser Lys Lys Tyr Tyr Ala Asp Ser Val Lys
1               5                   10                  15

Gly

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ser Leu Tyr Ser Ser Met Asp Leu
1               5

<210> SEQ ID NO 222
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ser Gly Ser Asn Ser Asn Ile Gly Lys Asn Tyr Val Ser
1               5                   10

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Glu Asp Asn Gln Arg Pro Ser
1               5

<210> SEQ ID NO 224
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224
```

```
Ala Ala Trp Asp Asp Leu Arg Gly Val His Trp Val
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Phe Thr Ser Arg His His Gly Met His
1               5                   10

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Val Ile Ser His Asp Gly Ser Lys Lys Tyr Tyr Ala Asp Ser Val Lys
1               5                   10                  15

Gly

<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ser Leu Tyr Ser Ser Met Asp Leu
1               5

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ser Gly Ser Asn Ser Asn Ile Gly Lys Asn Tyr Val Ser
1               5                   10

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Glu Asp Asn Gln Arg Pro Ser
1               5

<210> SEQ ID NO 230
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Ala Trp Asp Asp Arg His Gly Thr His Trp Val
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gly Phe Thr Ser Arg Asn Pro Gly Met His
1               5                   10

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Val Ile Ser His Asp Gly Ser Lys Lys Tyr Tyr Ala Asp Ser Val Lys
1               5                   10                  15
Gly

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Leu Tyr Ser Ser Met Asp Leu
1               5

<210> SEQ ID NO 234
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Gly Ser Asn Ser Asn Ile Gly Lys Asn Tyr Val Ser
1               5                   10

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235
```

```
Glu Asp Asn Gln Arg Pro Ser
1               5
```

<210> SEQ ID NO 236
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

```
Ala Ala Trp Asp Asp Ser Thr Gly Val His Trp Val
1               5                   10
```

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

```
Gly Phe Thr Ser Arg Thr Tyr Gly Met His
1               5                   10
```

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

```
Val Ile Ser His Asp Gly Ser Lys Lys Tyr Tyr Ala Asp Ser Val Lys
1               5                   10                  15

Gly
```

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

```
Ser Leu Tyr Ser Ser Met Asp Leu
1               5
```

<210> SEQ ID NO 240
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

```
Ser Gly Ser Asn Ser Asn Ile Gly Lys Asn Tyr Val Ser
1               5                   10
```

<210> SEQ ID NO 241
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Glu Asp Asn Gln Arg Pro Ser
1               5

<210> SEQ ID NO 242
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Ala Trp Asp Asp Leu Pro Thr Asp His Trp Val
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Phe Thr Ser Arg Gln Tyr Gly Met His
1               5                   10

<210> SEQ ID NO 244
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Val Ile Ser His Asp Gly Ser Lys Lys Tyr Tyr Ala Asp Ser Val Lys
1               5                   10                  15

Gly

<210> SEQ ID NO 245
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Leu Tyr Ser Ser Met Asp Leu
1               5

<210> SEQ ID NO 246
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246
```

```
Ser Gly Ser Asn Ser Asn Ile Gly Lys Asn Tyr Val Ser
1               5                   10

<210> SEQ ID NO 247
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Glu Asp Asn Gln Arg Pro Ser
1               5

<210> SEQ ID NO 248
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Ala Trp Asp Asp Tyr Ser Gly Val His Trp Val
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Phe Thr Ser Ser Pro Tyr Gly Met His
1               5                   10

<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Val Ile Ser His Asp Gly Ser Lys Lys Tyr Tyr Ala Asp Ser Val Lys
1               5                   10                  15

Gly

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ser Leu Tyr Ser Ser Met Asp Leu
1               5

<210> SEQ ID NO 252
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ser Gly Ser Asn Ser Asn Ile Gly Lys Asn Tyr Val Ser
1               5                   10

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Glu Asp Asn Gln Arg Pro Ser
1               5

<210> SEQ ID NO 254
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ala Ala Trp Asp Asp Asn Pro Arg Asp His Trp Val
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gly Phe Thr Ser Ser Lys Pro Gly Met His
1               5                   10

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Val Ile Ser His Asp Gly Ser Lys Lys Tyr Tyr Ala Asp Ser Val Lys
1               5                   10                  15
Gly

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257
```

```
Ser Leu Tyr Ser Ser Met Asp Leu
1               5

<210> SEQ ID NO 258
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ser Gly Ser Asn Ser Asn Ile Gly Lys Asn Tyr Val Ser
1               5                   10

<210> SEQ ID NO 259
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Glu Asp Asn Gln Arg Pro Ser
1               5

<210> SEQ ID NO 260
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ala Ala Trp Asp Asp Leu Arg Gly Val His Trp Val
1               5                   10

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gly Phe Thr Ser Lys Lys Tyr Gly Met His
1               5                   10

<210> SEQ ID NO 262
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Val Ile Ser His Asp Gly Ser Lys Lys Tyr Tyr Ala Asp Ser Val Lys
1               5                   10                  15

Gly

<210> SEQ ID NO 263
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Leu Tyr Ser Ser Met Asp Leu
1               5

<210> SEQ ID NO 264
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ser Gly Ser Asn Ser Asn Ile Gly Lys Asn Tyr Val Ser
1               5                   10

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Glu Asp Asn Gln Arg Pro Ser
1               5

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ala Ala Trp Asp Asp Leu Gly Gly Asp His Trp Val
1               5                   10

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Phe Thr Ser Thr Leu Pro Gly Met His
1               5                   10

<210> SEQ ID NO 268
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Val Ile Ser His Asp Gly Ser Lys Lys Tyr Tyr Ala Asp Ser Val Lys
```

Gly

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ser Leu Tyr Ser Ser Met Asp Leu
1               5

<210> SEQ ID NO 270
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ser Gly Ser Asn Ser Asn Ile Gly Lys Asn Tyr Val Ser
1               5                   10

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Glu Asp Asn Gln Arg Pro Ser
1               5

<210> SEQ ID NO 272
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ala Ala Trp Asp Asp Ser Ala Gly Val His Trp Val
1               5                   10

<210> SEQ ID NO 273
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gly Phe Thr Ser Lys Met Pro Gly Met His
1               5                   10

<210> SEQ ID NO 274
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 274

Val Ile Ser His Asp Gly Ser Lys Lys Tyr Tyr Ala Asp Ser Val Lys
1               5                   10                  15
Gly

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Ser Leu Tyr Ser Ser Met Asp Leu
1               5

<210> SEQ ID NO 276
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ser Gly Ser Asn Ser Asn Ile Gly Lys Asn Tyr Val Ser
1               5                   10

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Glu Asp Asn Gln Arg Pro Ser
1               5

<210> SEQ ID NO 278
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ala Ala Trp Asp Asp Glu His Gly Val His Trp Val
1               5                   10

<210> SEQ ID NO 279
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Phe Thr Ser Ser Asn Tyr Gly Met His
```

```
1               5                   10

<210> SEQ ID NO 280
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Val Ile Ser His Asp Gly Ser Lys Lys Tyr Tyr Ala Asp Ser Val Lys
1               5                   10                  15

Gly

<210> SEQ ID NO 281
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ser Leu Tyr Ser Ser Met Asp Leu
1               5

<210> SEQ ID NO 282
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ser Gly Ser Asn Ser Asn Ile Gly Lys Asn Tyr Val Ser
1               5                   10

<210> SEQ ID NO 283
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Glu Asp Asn Gln Arg Pro Ser
1               5

<210> SEQ ID NO 284
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ala Ala Trp Asp Asp Ser Leu Ser Ala His Trp Val
1               5                   10

<210> SEQ ID NO 285
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 285

Gly Phe Thr Ser Ser Asn Tyr Gly Met His
1               5                   10

<210> SEQ ID NO 286
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Val Ile Ser His Asp Gly Ser Lys Lys Tyr Tyr Ala Asp Ser Val Lys
1               5                   10                  15

Gly

<210> SEQ ID NO 287
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ser Met Val Ser Ser Met Asp Leu
1               5

<210> SEQ ID NO 288
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ser Gly Ser Asn Ser Asn Ile Gly Lys Asn Tyr Val Ser
1               5                   10

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Glu Asp Asn Gln Arg Pro Ser
1               5

<210> SEQ ID NO 290
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Ala Trp Asp Asp Ser Leu Ser Thr His Trp Val
```

```
              1               5                  10

<210> SEQ ID NO 291
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gly Phe Thr Ser Ser Asn Tyr Gly Met His
1               5                  10

<210> SEQ ID NO 292
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Val Ile Ser His Asp Gly Ser Lys Lys Tyr Tyr Ala Asp Ser Val Lys
1               5                  10                  15

Gly

<210> SEQ ID NO 293
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ser Met Arg Ser Ser Met Asp Leu
1               5

<210> SEQ ID NO 294
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ser Gly Ser Asn Ser Asn Ile Gly Lys Asn Tyr Val Ser
1               5                  10

<210> SEQ ID NO 295
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Glu Asp Asn Gln Arg Pro Ser
1               5

<210> SEQ ID NO 296
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 296

Ala Ala Trp Asp Asp Ser Leu Ser Ala His Trp Val
1               5                  10

<210> SEQ ID NO 297
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Ser Ser Asn Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Leu Ser Ser Leu Arg Pro Glu Asp Thr Ala Val Tyr Tyr Cys
                85                  90                  95

Ala Thr Ser Leu Tyr Ser Ser Met Asp Leu Trp Gly Gln Gly Thr Thr
            100                 105                 110

Val Thr Val Ser Ser
        115

<210> SEQ ID NO 298
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Lys Asn
            20                  25                  30

Tyr Val Ser Trp Phe Gln Gln Val Pro Gly Thr Ala Pro Lys Leu Leu
        35                  40                  45

Ile Phe Glu Asp Asn Gln Arg Pro Ser Gly Ile Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Ala His Trp Val Phe Gly Gly Gly Thr Lys Leu Thr Val Leu
            100                 105                 110

<210> SEQ ID NO 299
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Phe Thr Ser Ser Asn Tyr Gly Met His
1               5                   10

<210> SEQ ID NO 300
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Val Ile Ser His Asp Gly Ser Lys Lys Tyr Tyr Ala Asp Ser Val Lys
1               5                   10                  15

Gly

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Ser Leu Tyr Ser Ser Met Asp Leu
1               5

<210> SEQ ID NO 302
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ser Gly Ser Asn Ser Asn Ile Gly Lys Asn Tyr Val Ser
1               5                   10

<210> SEQ ID NO 303
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Glu Asp Asn Gln Arg Pro Ser
1               5

<210> SEQ ID NO 304
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304
```

```
Ala Ala Trp Asp Asp Ser Leu Ser Ala His Trp Val
1               5                   10
```

```
<210> SEQ ID NO 305
<211> LENGTH: 188
<212> TYPE: PRT
<213> ORGANISM: Homo sapiens

<400> SEQUENCE: 305

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

```
<210> SEQ ID NO 306
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Cys Pro Ser Cys Pro
1               5
```

```
<210> SEQ ID NO 307
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Cys Pro Pro Cys Pro
1               5
```

```
<210> SEQ ID NO 308
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Any amino acid

<400> SEQUENCE: 308

Phe Thr Ser Xaa Xaa Xaa Gly Met His
1               5

<210> SEQ ID NO 309
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(7)
<223> OTHER INFORMATION: Any amino acid

<400> SEQUENCE: 309

Trp Asp Asp Xaa Xaa Xaa Xaa His Trp Val
1               5                   10

<210> SEQ ID NO 310
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
cgcggcccag ccggccatgg cagaggtgca                                    30

<210> SEQ ID NO 311
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
ccaggccccc gaggcccagg acggtcagct                                    30

<210> SEQ ID NO 312
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(18)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (23)..(24)
<223> OTHER INFORMATION: a, c, t, g, unknown or other
```

```
<400> SEQUENCE: 312
gacccaatgc atgccmnnmn nmnnggaggt gaat                           34

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ggcatgcatt gggtccgcca                                           20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gtcatcccat gctgcacagt                                           20

<210> SEQ ID NO 315
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other

<400> SEQUENCE: 315
gcagcatggg atgacnnknn knnknnkcat tgggtgt                        37

<210> SEQ ID NO 316
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tgtcgcacag taatacacag ccgtgtcctc                                30

<210> SEQ ID NO 317
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other

<400> SEQUENCE: 317
tattactgtg cgacannknn knnknnknnk atggacctct                      40

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
tccatgagct tcctgatgct                                            20
```